US011260035B2

(12) United States Patent
Horn

(10) Patent No.: US 11,260,035 B2
(45) Date of Patent: *Mar. 1, 2022

(54) TOPICAL COMPOSITIONS AND METHODS OF USE THEREOF

(71) Applicant: PS Therapies Ltd, Bridgetown (BB)

(72) Inventor: Gerald Horn, Deerfield, IL (US)

(73) Assignee: PS Therapies Ltd, Bridgetown (BB)

( * ) Notice: Subject to any disclaimer, the term of this patent is extended or adjusted under 35 U.S.C. 154(b) by 8 days.

This patent is subject to a terminal disclaimer.

(21) Appl. No.: 16/668,398

(22) Filed: Oct. 30, 2019

(65) Prior Publication Data

US 2020/0061002 A1 Feb. 27, 2020

Related U.S. Application Data

(63) Continuation-in-part of application No. 16/412,943, filed on May 15, 2019, which is a continuation-in-part of application No. 16/372,625, filed on Apr. 2, 2019, which is a continuation-in-part of application No. 16/137,738, filed on Sep. 21, 2018, which is a continuation of application No. 15/730,837, filed on Oct. 12, 2017.

(60) Provisional application No. 62/563,154, filed on Sep. 26, 2017, provisional application No. 62/535,380, filed on Jul. 21, 2017, provisional application No. 62/519,011, filed on Jun. 13, 2017, provisional application No. 62/452,045, filed on Jan. 30, 2017, provisional application No. 62/428,031, filed on Nov. 30, 2016, provisional application No. 62/407,271, filed on Oct. 12, 2016.

(51) Int. Cl.

| A61K 31/167 | (2006.01) |
|---|---|
| A61K 9/00 | (2006.01) |
| A61K 31/05 | (2006.01) |
| A61K 31/4164 | (2006.01) |
| A61K 36/61 | (2006.01) |
| A61K 36/534 | (2006.01) |
| A61K 31/60 | (2006.01) |

(52) U.S. Cl.
CPC .......... *A61K 31/167* (2013.01); *A61K 9/0014* (2013.01); *A61K 31/05* (2013.01); *A61K 31/4164* (2013.01); *A61K 31/60* (2013.01); *A61K 36/534* (2013.01); *A61K 36/61* (2013.01)

(58) Field of Classification Search
CPC ...... A61K 31/167; A61K 9/0014; A61K 9/06; A61P 23/02
See application file for complete search history.

(56) References Cited

U.S. PATENT DOCUMENTS

| 5,961,997 A * | 10/1999 | Swinehart ................ A61K 8/34 |
| | | 424/401 |
| 6,511,949 B1 | 1/2003 | Nitta et al. |
| 6,528,048 B1 | 3/2003 | Koike et al. |
| 6,569,903 B2 | 5/2003 | Honma et al. |
| 8,067,038 B2 | 11/2011 | Arita et al. |
| RE43,583 E | 8/2012 | Arita et al. |
| 8,597,629 B1 | 12/2013 | Horn |
| 8,754,029 B2 | 6/2014 | Matsumura et al. |
| 8,933,006 B1 | 1/2015 | Horn |
| 9,034,843 B2 | 5/2015 | Matsumura et al. |
| 9,034,931 B2 | 5/2015 | Furumiya et al. |
| 9,050,369 B2 | 6/2015 | Nakata et al. |
| 9,173,945 B2 | 11/2015 | Matsumura et al. |
| 9,278,062 B2 | 3/2016 | Akagi et al. |
| 9,320,802 B2 | 4/2016 | Furumiya et al. |
| 9,345,779 B2 | 5/2016 | Nakata et al. |
| 9,427,473 B2 | 8/2016 | Komurasaki et al. |
| 2008/0312583 A1* | 12/2008 | Oronsky ............... A61K 9/0009 |
| | | 604/46 |
| 2010/0310642 A1 | 12/2010 | Mitra et al. |
| 2012/0269760 A1 | 10/2012 | Akagi et al. |
| 2013/0244971 A1 | 9/2013 | Ketelson et al. |
| 2013/0244978 A1 | 9/2013 | Matsumura et al. |
| 2014/0377210 A1 | 12/2014 | Horn |
| 2014/0378401 A1 | 12/2014 | Horn |
| 2017/0049789 A1* | 2/2017 | Bhalani .................. A61P 17/00 |
| 2017/0105934 A1 | 4/2017 | Mizutare et al. |

OTHER PUBLICATIONS

Belmonte et al., "Cold Thermoreceptors, Unexpected Players in Tear Production and Ocular Dryness Sensations", IOVS, May 2011, vol. 52, No. 6, p. 3888-3892.
Hirata et al., "Cold-Sensitive Corneal Afferents Respond to a Variety of Ocular Stimuli Central to Tear Production: Implications for Dry Eye Disease", IOVS, Aug. 2010, vol. 51, No. 8, p. 3969-3976.
Kovacs et al., "Abnormal activity of corneal cold thermoreceptors underlies the unpleasant sensations in dry eye disease", Pain Journal, 157 (2016) 399-417.
Kurose et al., "Corneal dry-responsive neurons in the spinal trigeminal nucleus respond to innocuous cooling in the rat", J Neurophysiol • doi:10.1152/jn.00889.2012 • www.jn.org.
Parra et al., "Tear fluid hyperosmolality increases nerve impulse activity of cold thermoreceptor endings of the cornea", Pain Journal, 155 (2014) 1481-1491.
Robbins et al., "Menthol Activation of Corneal Cool Cells Induces TRPM8-Mediated Lacrimation but Not Nociceptive Responses in Rodents", IOVS, Oct. 2012, vol. 53, No. 11, p. 7034-7042.

* cited by examiner

Primary Examiner — Michael B. Pallay
(74) Attorney, Agent, or Firm — Wood, Phillips, Katz, Clark & Mortimer

(57) ABSTRACT

The invention is directed to a topical composition comprising one or more topical active ingredients, one or more nonionic surfactants and one or more viscosity enhancers. The invention is further directed to a method of treating topical conditions comprising applying a composition of the present invention to a subject in need thereof.

2 Claims, 5 Drawing Sheets

TOPICAL COMPOSITIONS AND METHODS OF USE THEREOF

FIELD OF THE INVENTION

The invention is directed to a topical composition comprising one or more topical active ingredients, one or more nonionic surfactants and one or more viscosity enhancers. The invention is further directed to a method of treating topical conditions comprising applying a composition of the present invention to a subject in need thereof.

BACKGROUND OF THE INVENTION

Artificial Tears

The eye produces tears that are spread across the eye while blinking. The unique components of tears combined with the blinking process create a tear film that is made up of a mucous layer, an aqueous layer and a lipid layer. This tear film undergoes significant forces that can compromise the integrity of the film including: 1) evaporation, 2) spreading along the ocular surface, which is driven by high shear blinks, 3) draining, which is aided by blink powered lacrimal pumping and 4) low shear flow along the lid tear menisci. To maintain the tear film the film is continually replenished with new tear film components upon each blink, which is triggered by tear breakup and corneal surface nerve excitation. This unique system creates a barrier between the environment and the surface of the eye and removes any irritants that may enter the eye. Further, tears have critical components derived from the blood plasma that are filtered to nourish the ocular surface, reduce infection risk and promote healing of ocular surface tissues. A healthy tear film is necessary for optimal vision just as an unhealthy tear film results in degradation of visual quality and or acuity. There are several events that can cause a reduction in the quantity or quality of tears including intra- or extraocular surgery affecting the ocular surface, dry eye syndrome, dry eye following eye surgery, ocular surface abnormalities from medication and or preservative toxicity, and contact lens solution and or contact lens use.

The tear film is the single most important optical surface. Disturbances that affect the quality and duration of that film on the cornea can dramatically alter quality of vision. These disturbances include reduced volume as measured by Schirmer's test, reduced tear breakup time and reduced tear prism (i.e. the measure of the meniscus along the lower lid where tears flow). Unfortunately, the true measures of a healthy tear film: the thickness and or volume of each layer, the composition within each layer, and the resulting flow properties and stabilization of the tear film are not easily measured. Tear abnormalities manifest as a large range of tear deficiencies from composition abnormalities of one or more of the mucous, aqueous and lipid layers to volume abnormalities including reduction in the thickness and or volume of one or more of these layers and combinations thereof.

Dry eye is a generic term for any abnormality in tear layer thickness or tear layer composition. Dry eye is a common affliction that is caused by the failure of the eye to produce either an adequate amount or maintain a proper balance of tear components in the mucous, aqueous or lipid layers. In either instance, the tear film that normally covers the eye becomes unstable (i.e. no longer covers the entire eye evenly and for a sufficient period.) A sufficient period is typically about eight seconds. Tear film instability causes tears to bead up leaving surface coverage dry spots while failing to remove irritants. These dry spots and irritants cause many of the conditions associated with dry eye such as burning, stinging, itching and tired eyes. Dry eye symptoms can be exacerbated by activities that extend the time between eye blinks such as prolonged computer use and reading. Even mild tear film degradation can reduce the tear break up time ("TBUT") leading to excessive blinking. Blinking may achieve brief moments of complete even tear film coverage where vision is optimized. However, this relief is sporadic and short-lived, and the tear film may become degraded altogether making even frequent blinking ineffective.

Dry eye often occurs following any incisional or ablative procedure that cuts corneal nerves, by reducing the neurologic trigger for tear secretion, or disrupting the external surface creating abnormal spreading and elevated dry spots (dellen). Procedures include: corneal or scleral eye surgery including but not limited to cataract incisions; corneal transplant surgery; glaucoma surgery filtering blebs; and any incisional or ablative corneal surgery. Dry eye following eye surgery can lead to increased pain to the patient, increased infection risk, reduced vision and increased sensitivity to topical medications and preservatives. This increased sensitivity may exacerbate ocular surface disease, have similar symptomatology to dry eye, and result in prolonged epithelial healing times.

Current artificial tear compositions designed to reduce or alleviate dry eye contain polymers that act to mimic the mucous, aqueous and or lipid layers of the tear film to maintain the stability of the film and prevent rapid evaporation. High viscosity artificial tear compositions maintain a longer lasting tear film. However, these compositions cause viscous drag on the eye lids while blinking creating an uncomfortable "sticky" sensation, may be difficult to apply and create crust on the eye lids. These high viscosity compositions also result in blurred vision, typically for several minutes or longer. Low viscosity compositions do not maintain a long-lasting tear film, in part, due to a quicker loss of these aqueous solutions to evaporation and draining aided by blink powered lacrimal pumping.

Current artificial tear compositions for treating dry eye are deficient for many reasons including: i) they maintain a stable tear film for only a short period of time, typically 15 minutes or less after which tear properties return to baseline; ii) higher viscosity formulations only last modestly longer (about 25 minutes or less) and they cause blurred vision for a relatively long period of time (as long as 12 minutes for Refresh® Celluvisc (400 cps), frequently requiring frantic blinking until it thins out enough and stabilizes; iii) they either do not provide an evaporative shield to reduce drying or they have a synthetic and or oily feeling from added lipids or lipid-like substances that do not stabilize the aqueous layer; iv) they do not provide a protective coating over the conjunctiva of the lids and or sufficiently dissolve lipid inspissation within Meibomian glands, both hallmarks of dry eye characterized by such Meibomian gland inspissation and dysfunction ("MGD"); v) they do not provide a physiologically enhanced environment for epithelial cell healing and maintain integrity; vi) they do not prevent, reduce, or help dissolve protein, cholesterol, or dried mucous that may deposit on contact lens surfaces, the corneal epithelium, or the conjunctiva of the lid and irritate or otherwise degrade these cell membranes; vii) they do not significantly promote tear secretion or provide prolonged exposure to and retention of existing tears (prescription drugs such as Restasis® or Xiidra® attempt to increase tear secretion but cause only marginal increases); and viii) they result in higher osmolality and wetting angle making tear spread more difficult and uneven.

Efforts to create evaporative shielding to retain the aqueous tear layer, such as addition of lipids or phospholipids are compromised not only by the synthetic oily unnatural sensation that results, but also by the poor aqueous layer stabilization and very short duration of the instilled drop or prolonged blur of a more viscous slightly longer lasting artificial tear. While the goal is retention of the artificial tear in the cul de sac, which allows each blink to pull more of the artificial tear across the cornea, there is tremendous lacrimal duct drainage via capillary attraction limiting this benefit with conventional tear formulations. The longest lasting artificial tears on the market use high concentrations of viscosity enhancing agents. Celluvisc® (Celluvisc is a registered trademark of Allergan, Inc.), which uses high viscosity carboxymethyl cellulose ("CMC") 1%—about 350 centipoise ("cps") viscosity, and Refresh Liquigel® (Refresh Liquigel is a registered trademark of Allergan, Inc.), which uses a blend of 0.35% high viscosity CMC and 0.65% low viscosity CMC—about 70 cps, are two such compositions. These high viscosity artificial tear compositions are long lasting but cause significantly blurred vision lasting up to 10 minutes or longer.

Artificial tear compositions have made progress. This progression has been based on improving difficult to measure TBUT, duration of added wetting, and degree and duration of blur relative to viscosity. The first generation of artificial tears was a simple saline solution with the addition of other electrolytes and certain minerals still found in eye drops today, such as Theratears® (Theratears is a registered trademark of Advanced Vision Research, Inc.). A second generation was developed by adding natural and synthetic polymers, particularly polyvinyl alcohols and cellulose derivative viscosity agents. The most natural feeling and therefore popular formulation from the second generation is Refresh® tears (Refresh is a registered trademark of Allergan Pharmaceuticals, Inc.). A third generation was developed by adding hyaluronic acid (hyaluronates). The third generation promotes slower lacrimal duct drainage and greater retention on the eye by providing non-Newtonian flow properties. However, the third generation has only moderate tear layer stabilization and retention. The third generation also decreases the duration of blur and stabilizes the tear film. However, third generation formulations are oilier and their unnatural, 'moisture-lacking' sensation makes them less popular than many products on the market today from the second generation. Further, the third generation has very little demonstrated therapeutic clinical differentiation from the second generation. A fourth generation was developed consisting of lipid-based oil-in-water ("O/W") emulsions. The O/W emulsions of the fourth generation reduces tear film evaporation, stabilizes the lipid layer and prolongs duration. These formulations require the addition of nonionic or cationic surfactants for stabilization. However, these formulations do not promote increased spreading, provide any useful adjunctive aqueous layer stabilizers across the eye, or retard high shear blink lacrimal pumping leading to minimally enhanced retention. These formulations may be limited by the low concentrations of surfactants in conventional artificial tears due to their known toxicity at 1.0% or greater. Additionally, as with the third generation, the fourth-generation artificial tear has minimal therapeutic detectable clinical benefit and a synthetic and less comfortable quality.

Drug Vehicles

Ophthalmic drug efficacy is severely limited by non-compliance. Compliance is adversely affected by the reduced comfort, irritation, and transient quality of vision loss, which lasts minutes to tens of minutes, that is common to many drugs. In particular, these adverse effects are caused by suspensions commonly used for highly lipophilic drugs or the requirement of very high topical concentrations for highly hydrophilic drugs.

The fundamental challenges of ophthalmic delivery vehicles are to improve comfort; minimize visual blur on instillation; increase drug solubility; increase drug residence time and permeation through the cornea to achieve greater intraocular delivery; reduce systemic drug absorption; and cause minimal local adverse effect. Unfortunately, these objectives are not met by current ophthalmic formulations.

Current artificial tear vehicles may be used for drug solubilization, but do not confer increased drug residence time or offer other efficacy benefits. More viscous artificial tears use high concentrations of viscosity enhancing agents, such as Celluvisc® (Celluvisc is a registered trademark of Allergan, Inc.), high viscosity carboxymethyl cellulose (CMC) 1%—about 350 centipoise (cps) viscosity, and Refresh Liquigel® (Refresh Liquigel is a registered trademark of Allergan, Inc.), a blend of 0.35% high viscosity CMC and 0.65% low viscosity CMC—about 70 cps, but these formulations have prolonged visual blur that may last for 10 minutes or longer, greatly reducing compliance. These artificial tear vehicles also do not leach drug slowly but rather release a lot to drainage.

Gelling agents have been used with some success in increasing drug residence time and improving drug solubility. By definition such agents are instilled as liquid and then almost immediately triggered to a gel phase, where drug residence time is increased and drug release time extended. Timoptic XE® gel (gellan gum; Timoptic XE is a registered trademark of Merck & Co, Inc.), AzaSite® (Azasite is a registered trademark of Insite Vision, Inc.) (polycarbophil, poloxamer), and Besivance® (Besivance is a registered trademark of Bausch & Lomb, Inc.), (polycarbophil, poloxamer), 0.3% alginate Keltrol®) (Keltrol is a registered trademark of CP Kelco U.S., Inc.) are examples of such agents, where polycarbophil-poloxamer gels are commercially known as Durasite® (Durasite is a registered trademark of Insite Vision, Inc.).

However, most gelling agents: 1) increase blur on instillation; 2) cause lid and lash encrusted gel residue; 3) cause irritation/stinging on instillation; and 4) allow substantial active drug to be released systemically and may have systemic side effects. For drugs with minimal systemic side effects, or intended for only acute use of a few days, these issues are somewhat mitigated; but for drugs with higher systemic effect profiles, particularly lipophilic drugs, and more particularly as chronic use drugs, these issues can seriously affect compliance.

Gelling agents experience a phase transition to a highly viscous state, typically achieving 500-1000 cps or more after their transition. Ionic, pH, and thermal triggers are typically used. However, the high shear force of each blink breaks up such phase modified films into discrete particles easily drained into the nasolacrimal duct to the nasal turbinates where residual drug may readily enter systemic circulation. Many gelling agents combine poloxamers of various molecular weights with viscosity enhancers or other gelling agents to create the desired phase transition from liquid on instillation to gel. Typically for those formulations using poloxamer without a second gelling agent, poloxamer concentrations of 15% or greater are needed to achieve gel-transition temperatures at body temperature (37° C.).

Patel (Int. J. of Pharm. Chem. Sci., Vol. 1, October-December 2012) describes the use of poloxamer and a viscosity enhancing agent—a low molecular weight, low viscosity hydroxypropylmethyl cellulose (HPMC E50LV) 1.5% with brimonidine and demonstrates on testing concentrations of poloxamer with the HPMC from 1% to 19%, no clinically useful gelling capacity in vitro below 15%. Given the dilution of tear film, this typically requires about 21% poloxamer to achieve phase transition to gel on ophthalmic instillation. For example, Qian (Drug Dev. And Industrial Pharmacy, 2010, 36(1): 1340-1347) describes an in-situ gelling system for methazolamide, a carbonic anhydrase inhibitor (glaucoma), using 21% poloxamer 407 and 10% poloxamer 188 to achieve a preferred phase transition to gel. High viscosity gels have been described with similar limitations to in situ gels, specifically trading off the most egregious noncompliance factors of lid and lash residue and viscous lid drag for lesser amounts of both and with less but still substantially prolonged vision blur.

Use of low viscosity agents reverses the predicament. Other compositions attempt to optimize compliance with formulations that have low viscosity agents such that comfort is good, vision is good and surface residue is absent. However, in such formulations, tear dilution is almost immediate, and drug residence time is severely limited versus in situ gels or viscous liquid gels. Therefore, formulations either improve compliance or enhance efficacy but not both. This is often seen with vehicles for dry eye. Refresh Liqui-gel® at 70 cps and Celluvisc® at 300 cps are such examples where vision blur is noted.

Topical Compositions

Current topical compositions including analgesics, hemorrhoid treatments, acne treatments, anti-wrinkle compositions and anti-scar compositions all suffer from similar deficiencies regarding epidermal penetration. For example, antibiotic ointments used to treat acne including erythromycin or clindamycin are normally co-administered with oral antibiotics due to poor epidermal penetration. Similarly, mupirocin used to treat cellulitis is also co-adminstered with oral antibiotics due to poor topical efficacy.

Thus, there is a need in the art for a topical composition that can
   increase residency time, absorbency, safety or efficacy of the drug on the surface of the skin.

SUMMARY OF THE INVENTION

Artificial Tears

In certain embodiments, the present invention is directed to artificial tear compositions comprising a means for inducing tears and a means for sequestering tears.

In a preferred embodiment, the means for inducing tears is selected from a pH from about 5 to about 6, a terpenoid and an osmolarity of from about 350 to about 550 milliosmoles.

In another preferred embodiment, the means for sequestering tears comprises from about 1.5% to about 5.9% w/v total volume of one or more nonionic surfactants and one or more viscosity enhancers, wherein the one or more viscosity enhancers provides a viscosity of from about 50 to about 10,000 centipoise at 0 shear to 1 second.

In more preferred embodiment, the one or more nonionic surfactants are selected from the group consisting of polysorbates, poloxamers, polyoxyl castor oils, cyclodextrins (alpha, beta or gamma) and combinations thereof.

In another more preferred embodiment, the one or more viscosity enhancers are selected from the group consisting of cellulose derivatives, carbomers, gums, and hyaluronic acids, dextrans, polyvinyl alcohol, polyacrylic acids, povidone, polyethylene glycols, propylene glycol, chitosans and combinations thereof, even more preferably the one or more viscosity enhancers are selected from the group consisting of cellulose derivatives, carbomers, polyvinyl alcohol, polyethylene glycols and combinations thereof.

In another embodiment, the artificial tear compositions of the present invention further comprise a polyol, preferably selected from the group consisting of mannitol, xylitol, sorbitol, isosorbide, erythritol, glycerol, maltitol and a combination thereof.

In another embodiment, the artificial tear compositions of the present invention further comprise one or more electrolytes, preferably selected from the group consisting of magnesium ions, sodium chloride, potassium chloride and a combination thereof.

In another embodiment, the artificial tear compositions of the present invention further comprise one or more lipids, preferably omega 3 fatty acids.

In another preferred embodiment, the present invention is directed to artificial tear compositions comprising one or more nonionic surfactants, preferably at a concentration from about 1.25% to about 10.0% w/v, one or more viscosity enhancers and a means of inducing tearing including via nociception, preferably selected from the group consisting of a pH below 6.0; an osmolarity of about 250 mosm less, an osmolarity of 350 mosm or more; an osmolarity of 400 mosm or more; an osmolarity of 450 mosm or more; from about 0.05 to about 4.0 mM menthol and a combination thereof, preferably resulting in induced tearing and prolonged sequestration.

In another preferred embodiment, the present invention is directed to artificial tear compositions comprising from about 1.5% to about 5.9% w/v total concentration of one or more nonionic surfactants, one or more viscosity enhancers, a means of inducing tearing selected from the group consisting of a pH below 6.0; an osmolarity of 350 mosm or more; menthol, and a combination thereof.

In another preferred embodiment, the present invention is directed to artificial tear compositions comprising at least 1.0% w/v total concentration of one or more nonionic surfactants, preferably from about 1.0% to about 10.0% w/v, more preferably from about 1.5% to about 5.9% w/v one or more viscosity enhancers and menthol.

In another preferred embodiment, the present invention is directed to artificial tear compositions comprising:
   one or more nonionic surfactants selected from the group consisting of poloxamers, polysorbates, cyclodextrins, alkylaryl polyethers, polyoxyethyleneglycol alkyl ethers, tyloxapol, and polyoxyls at a total concentration from about 1.25% to about 7.0% w/v, preferably selected from the group consisting of about 0.01% to about 4.0% w/v of a polysorbate, from about 0.01% to about 3.0% w/v of one or more poloxamers, from about 0.01% to about 1.0% w/v of a polyoxyl and from about 0.01% to about 5.0% w/v hydroxypropyl-gamma-cyclodextrin;
   a viscosity enhancer selected from the group consisting of cellulose derivatives, carbomers, gums, dextrans, polyvinyl alcohol, polyacrylic acids, povidone, polyethylene glycol, propylene glycol, chitosans, hyaluronates, hyaluronic acids and combinations thereof; from about 0.01% to about 3.0% w/v of an electrolyte selected from the group consisting of sodium chloride, potassium chloride, magnesium ions and combinations thereof, preferably the electrolyte is selected from about 0.01% to about 0.25% w/v magnesium ions, from about 0.10% to about 2.0% w/v sodium chloride, from about 0.1% to about 0.5% w/v potassium chloride and combinations thereof;

a means of inducing tearing selected from the group consisting of a pH below 6.0; an osmolarity of 350 mosm or more; menthol, and a combination thereof; and optionally, about 0.1% w/v sorbate, preferably, wherein the concentration of the viscosity enhancer provides a composition with a viscosity from about 0.1 to about 1,000 centipoise (cps), and preferably, wherein a low shear viscosity is from about 1 to about 1000 cps and a final high shear viscosity is about 30 cps or less.

In another preferred embodiment, the present invention is directed to artificial tear compositions comprising:

one or more nonionic surfactants selected from the group consisting of poloxamers, polysorbates, cyclodextrins, alkylaryl polyethers, polyoxyethyleneglycol alkyl ethers, tyloxapol, and polyoxyls at a total concentration from about 1.25% to about 7.0% w/v, preferably the one or more nonionic surfactants are selected from the group consisting of from about 0.01% to about 4.0% w/v of a polysorbate, from about 0.01% to about 3.0% w/v of one or more poloxamers, from about 0.01% to about 1.0% w/v of a polyoxyl and optionally, from about 0.01% to about 5.0% w/v hydroxypropyl-gamma-cyclodextrin;

optionally, from about 0.1% to about 0.75% w/v sodium chloride;

from about 0.01 mM to about 0.50 mM menthol;

optionally, from about 0.1% to about 4% w/v of a polyol, preferably the polyol is mannitol or glycerol at a concentration from about 1.0% to about 2.5% w/v;

a viscosity agent selected from the group consisting of cellulose derivatives, carbomers, gums, dextrans, polyvinyl alcohol, polyacrylic acids, povidone, polyethylene glycol, propylene glycol, chitosans, hyaluronates, hyaluronic acids and combinations thereof, preferably wherein the composition has a viscosity from about 1 to about 1,000 centipoise; and optionally, from about 0.01% to about 0.25% w/v magnesium ions.

In a preferred embodiment, the present invention is directed to artificial tear compositions comprising:

from about 2.0% to about 4.0% w/v of one or more nonionic surfactants selected from the group consisting of polysorbates, poloxamers, polyoxyl castor oils and combinations thereof;

from about 0.5% to about 2.0% w/v of a viscosity enhancer selected from the group consisting of carboxymethyl cellulose and carbomer 940;

from about 1.0% to about 5.0% w/v mannitol;

from about 0.5% to about 1.0% w/v of a polyethylene glycol selected from polyethylene glycol 400, polyethylene glycol 6000, polyethylene glycol 10000, polyethylene glycol 20000 and a combination thereof;

from about 0.1% to about 2.0% w/v sodium chloride;

from about 0.1% to about 0.12% w/v sorbate;

from about 3.0 to about 10.0 millimolar citrate buffer, wherein w/v denotes weight by total volume of the composition and wherein the composition has a pH from about 5.0 to about 7.4, preferably from about 5.0 to about 6.0.

In another preferred embodiment, the present invention is further directed to methods of treating dry eye comprising administering a composition of the present invention to a subject in need thereof.

In another preferred embodiment, the present invention is further directed to methods of treating ocular surface defects, deficiencies and disease selected from the group consisting of superficial punctate keratitis, epithelial abrasions, post-surgical ocular surface abnormality such as post glaucoma shunt, post cataract, post refractive surgery, dry eye syndrome, keratoconjunctivitis sicca, dry eye following incisional or ablative surgery such as corneal/glaucoma surgery, cataract incisions, corneal transplant, glaucoma surgery filtering blebs, ocular surface abnormalities caused by medication, preservatives, contact lens solution and contact lens use or methods of treating endophthalmitis.

In another preferred embodiment, the present invention is further directed to methods of treating eye pain comprising administering a composition of the present invention to a subject in need thereof.

In another preferred embodiment, the present invention is further directed to methods of enhancing wound healing following corneal surgery comprising administering a composition of the present invention to a subject in need thereof.

In another preferred embodiment, the present invention is further directed to methods of treating Meibomian gland dysfunction comprising administering a composition of the present invention to a subject in need thereof.

In another preferred embodiment, the present invention is further directed to an artificial tear composition comprising one or more nonionic surfactants, one or more viscosity enhancers, a polyol, one or more electrolytes and menthol.

In another preferred embodiment, the one or more nonionic surfactants are polysorbate 80, poloxamer 407, poloxamer 188 and polyoxyl castor oil.

In another preferred embodiment, the one or more viscosity enhancers are selected from cellulose derivatives.

In another preferred embodiment, the polyol is mannitol.

In another preferred embodiment, the one or more electrolytes are magnesium chloride and sodium chloride.

In another preferred embodiment, the one or more nonionic surfactants are polysorbate 80, poloxamer 407, poloxamer 188, polyoxyl castor oil and hydroxypropyl-gamma-cyclodextrin.

In another preferred embodiment, the artificial tear compositions of the present invention further comprise a polyethylene glycol.

In another preferred embodiment, the polyethylene glycol is polyethylene glycol 400.

In another preferred embodiment, the artificial tear compositions of the present invention further comprise ascorbic acid or d-alpha tocopherol.

In another preferred embodiment, the artificial tear compositions of the present invention further comprise sorbate.

In another preferred embodiment, the total concentration of the one or more nonionic surfactants is at least 1.0% w/v, preferably from about 1.0% w/v to about 10.0% w/v and more preferably from about 1.5% w/v to about 5.9% w/v.

In another preferred embodiment, the cellulose derivative is at a concentration that provides a viscosity equivalent to hydroxypropylmethyl cellulose at a concentration from about 0.01% to about 2.5% w/v, more preferably from about 0.01% to about 1.5% w/v or high molecular weight carboxymethyl cellulose at a concentration from about 0.01% to about 1.5% w/v, wherein "high molecular weight" is at 3,500 cps or more.

In another preferred embodiment, the menthol is at a concentration from about 0.01 to about 4.0 millimolar, more preferably from about 0.01 to about 0.40 millimolar or from about 0.2 to about 2.5 millimolar or from about 0.2 to about 1.6 millimolar.

In another preferred embodiment, the present invention is further directed to an artificial tear composition comprising from about 0.5% to about 1.5% w/v polysorbate 80, preferably, from about 1.00% to about 1.50% w/v polysorbate 80, from about 0.5% to about 1.5% w/v poloxamer 407, preferably from about 0.7% to about 1.00% w/v poloxamer 407, from about 0.20% to about 1.00% w/v poloxamer 188, from about 0.01% to about 0.50% w/v polyoxyl castor oil, preferably from about 0.01% to about 0.30% w/v polyoxyl castor oil, from about 0.1% to about 2.0% w/v carboxymethyl cellulose, preferably from about 0.1% to about 1.5% w/v carboxymethyl cellulose and from about 0.01 to about 0.50 millimolar menthol, preferably from about 0.01 to about 0.40 millimolar menthol and optionally, from about 0.1% about 1.5% w/v polyethylene glycol 400, preferably about 0.50% w/v polyethylene glycol 400, from about 0.5% to about 1.5% mannitol, preferably about 0.75% or about 1.00% w/v mannitol, about 0.10% w/v magnesium chloride, about 0.35% to about 0.45% w/v sodium chloride and from about 3 to about 4 millimolar of a buffer selected from phosphate and citrate.

In another preferred embodiment, the artificial tear compositions of the present invention further comprise from about 0.1% to about 0.15% w/v sorbate, preferably from about 0.11% to about 0.12% w/v sorbate.

In another preferred embodiment, the artificial tear compositions of the present invention further comprise greater than 0.1% w/v sorbate, preferably from 0.11% to about 10.0% w/v.

In another preferred embodiment, the artificial tear compositions of the present invention further comprise from about 0.25% to about 5.5% w/v hydroxypropyl-gamma-cyclodextrin, preferably from about 1.5% to about 2.0% w/v.

In another preferred embodiment, the artificial tear compositions of the present invention further comprise from about 1 to about 200 international units of d-alpha tocopherol, preferably from about 30 to about 50 international units.

In another preferred embodiment, the artificial tear compositions of the present invention have a pH from about 5.7 to about 8.0, preferably from about 5.7 to about 6.5.

In another preferred embodiment, the present invention is further directed to an artificial tear composition comprising from about 0.5% to about 1.5% w/v polysorbate 80, preferably, from about 1.00% to about 1.50% w/v polysorbate 80, from about 0.5% to about 1.5% w/v poloxamer 407, preferably from about 0.7% to about 1.00% w/v poloxamer 407, from about 0.20% to about 1.00% w/v poloxamer 188, from about 0.01% to about 0.50% w/v polyoxyl castor oil, preferably from about 0.01% to about 0.30% w/v polyoxyl castor oil, from about 0.1% to about 2.0% w/v hydroxypropylmethyl cellulose, preferably from about 0.1% to about 1.2% w/v hydroxypropylmethyl cellulose, from about 0.1% about 1.5% w/v polyethylene glycol 400, preferably about 0.50% w/v polyethylene glycol 400, from about 0.5% to about 1.5% mannitol, preferably about 0.75% or about 1.00% w/v mannitol, about 0.10% w/v magnesium chloride and about 0.35% to about 0.45% w/v sodium chloride, from about 0.1% to about 0.11% w/v sorbate, from about 1.5% to about 2.5% w/v hydroxypropyl-gamma-cyclodextrin, from about 10 to about 200 international units of d-alpha tocopherol and wherein the composition has a pH from about 5.7 to about 8.0.

Drug Vehicles

In one embodiment, all artificial tear compositions of the present invention are capable of being used as drug vehicles.

In another preferred embodiment, the present invention is directed to an ophthalmological drug composition comprising a means to sequester tears and an ophthalmological drug, preferably selected from the group consisting of trehalose, cyclosporine (cyclosporine is the active ingredient in Restasis® available from and a registered trademark of Allergan, Inc. and Cequa® available from and a registered trademark of Sun Pharma Global FZE), lifitegrast (lifitegrast is the active ingredient in Xiidra® available from and a registered trademark of SARcode Bioscience Inc.), diquafosol (diquafosol is the active ingredient in Diquas® available from and a registered trademark of Santen Pharmaceutical Co., Ltd), a C-terminal 25 amino acid fragment of lacritin (known as Lacripep® available from and a registered trademark of TearSolutions, LLC), lacritin, KPI-121 (KPI-121 is the active ingredient in Inveltys™ available from Kala Pharmaceuticals), tivanisiran (tivanisiran is the active ingredient in Sylentis® available from and a registered trademark of Sylentis, S.A.U.), omega 3 fatty acids, an antibiotic, a steroid anti-inflammatory, a nonsteroidal anti-inflammatory, a glaucoma drug, a prostaglandin, a muscarinic receptor agonist, a miotic agent, drugs known to cause dry eye such as topical antihistamines and alpha 2 agonists (brimonidine), and a combination thereof.

In another preferred embodiment, the present invention is further directed to an ophthalmological drug vehicle composition comprising an ophthalmological drug and one or more nonionic surfactants and at least one excipient selected from a viscosity enhancer, a polyol and an electrolyte, preferably the ophthalmological drug is selected from the group consisting of diquafosol, cyclosporine, a prostaglandin, an antibiotic, a muscarinic receptor agonist, a non-steroidal anti-inflammatory, a steroidal anti-inflammatory, GLC. acetylsalicylic acid, salicylic acid and a combination thereof.

In another embodiment, the compositions of the present invention are capable of solubilizing or encapsulating an ophthalmological drug and providing a prolonged exposure to the surface of the eye. This prolong exposure may allow the drug to be both longer acting and increase the penetration of the drug into the eye. Ophthalmological drugs suitable for use in the present invention include, but are not limited to, diquafosol, cyclosporine, a prostaglandin, an antibiotic, a non-steroidal anti-inflammatory, a steroidal anti-inflammatory or a combination thereof.

In another preferred embodiment, the present invention is directed to an ophthalmological drug delivery means, preferably selected from the group consisting of contact lenses, punctum plugs and pellets, coated or infused with the compositions of the present invention.

In another embodiment, ophthalmological drug compositions of the present invention include standard dropper bottles, multi-dose preservative free bottles and unit dose delivery.

In another preferred embodiment, the present invention is further directed to methods of increasing drug residency time on the surface of the eye comprising the steps of:

suspending or dissolving an ophthalmological drug in a composition of the present invention to create an ophthalmological drug composition; and instilling the ophthalmological drug composition in the eye of a subject in need thereof.

In a preferred embodiment, the active agent for the treatment of dry eye achieves greater efficacy via residence time and permeation; and greater efficacy via vehicle sequestration of induced tearing.

In another preferred embodiment, the present invention is further directed to methods of reducing ocular infections comprising instilling the composition of claim 1 into the eye of a subject in need thereof.

In another preferred embodiment, the present invention is further directed to methods of treating dry age-related macular degeneration, wet age-related macular degeneration or diabetes comprising administering to a subject in need thereof an ophthalmological drug vehicle of the present invention.

In another preferred embodiment, the present invention is further directed to a topical drug vehicle composition comprising a topical drug and one or more nonionic surfactants and at least one excipient selected from a viscosity enhancer, a polyol and an electrolyte, preferably the ophthalmological drug is selected from the group consisting of cyclosporine, a prostaglandin, an antibiotic, a non-steroidal anti-inflammatory, a steroidal anti-inflammatory, GLC and a combination thereof.

Lidocaine Gel Compositions

In one embodiment, the present invention is directed to a topical ophthalmological lidocaine gel composition comprising lidocaine or a salt thereof and magnesium chloride.

In a preferred embodiment, the present invention is directed to a topical ophthalmological lidocaine gel composition comprising lidocaine or a salt thereof, magnesium chloride, a nonionic surfactant, a polyethylene glycol, mannitol, a viscosity enhancer and sodium chloride.

In another preferred embodiment, the present invention is directed to a topical ophthalmological lidocaine gel composition comprising:
from about 3% to about 4% w/v lidocaine hydrochloride;
from about 3% to about 4% w/v polysorbate 80;
from about 0.25% to about 2.5% w/v of a polyethylene glycol having a molecular weight of from about 400 to about 20,000 Daltons;
from about 0.25% to about 1.5% w/v mannitol; and
from about 0.05% to about 0.2% w/v magnesium chloride.

In another preferred embodiment, the present invention is directed to a topical ophthalmological lidocaine gel composition comprising:
about 3.5% w/v lidocaine hydrochloride;
about 3.5% w/v polysorbate 80;
from about 0.75% to about 1.50% w/v of a polyethylene glycol having a molecular weight of from about 400 to about 20,000 Daltons;
about 0.75% w/v mannitol;
about 0.1% w/v magnesium chloride;
from about 0.9% to about 1.25% w/v sodium chloride;
about 3 millimolar citrate buffer;
from about 1.25% to about 1.50% w/v carboxymethyl cellulose; and
about 0.1% w/v sorbate.

In another embodiment, the present invention is directed to a method of inducing local anesthesia in an eye of a patient comprising topically applying compositions of the present invention to the eye of the patient.

Topical Compositions

In one embodiment, the present invention is directed to a topical composition comprising one or more topical active ingredients, one or more nonionic surfactants and one or more viscosity enhancers.

In another embodiment, the present invention is directed to a method of reducing or eliminating pain comprising applying a composition of the present invention to a subject in need thereof.

In another embodiment, the present invention is directed to a method of treating hemorrhoids comprising applying a composition of the present invention to a subject in need thereof.

In another embodiment, the present invention is directed to a method of reducing or eliminating acne comprising applying a composition of the present invention to a subject in need thereof.

In another embodiment, the present invention is directed to a method of reducing or eliminating wrinkles comprising applying a composition of the present invention to a subject in need thereof.

In another embodiment, the present invention is directed to a method of reducing or eliminating scars comprising applying a composition of the present invention to a subject in need thereof.

DETAILED DESCRIPTION OF THE INVENTION

Discoveries of the Invention

Artificial Tears

Figure 1:
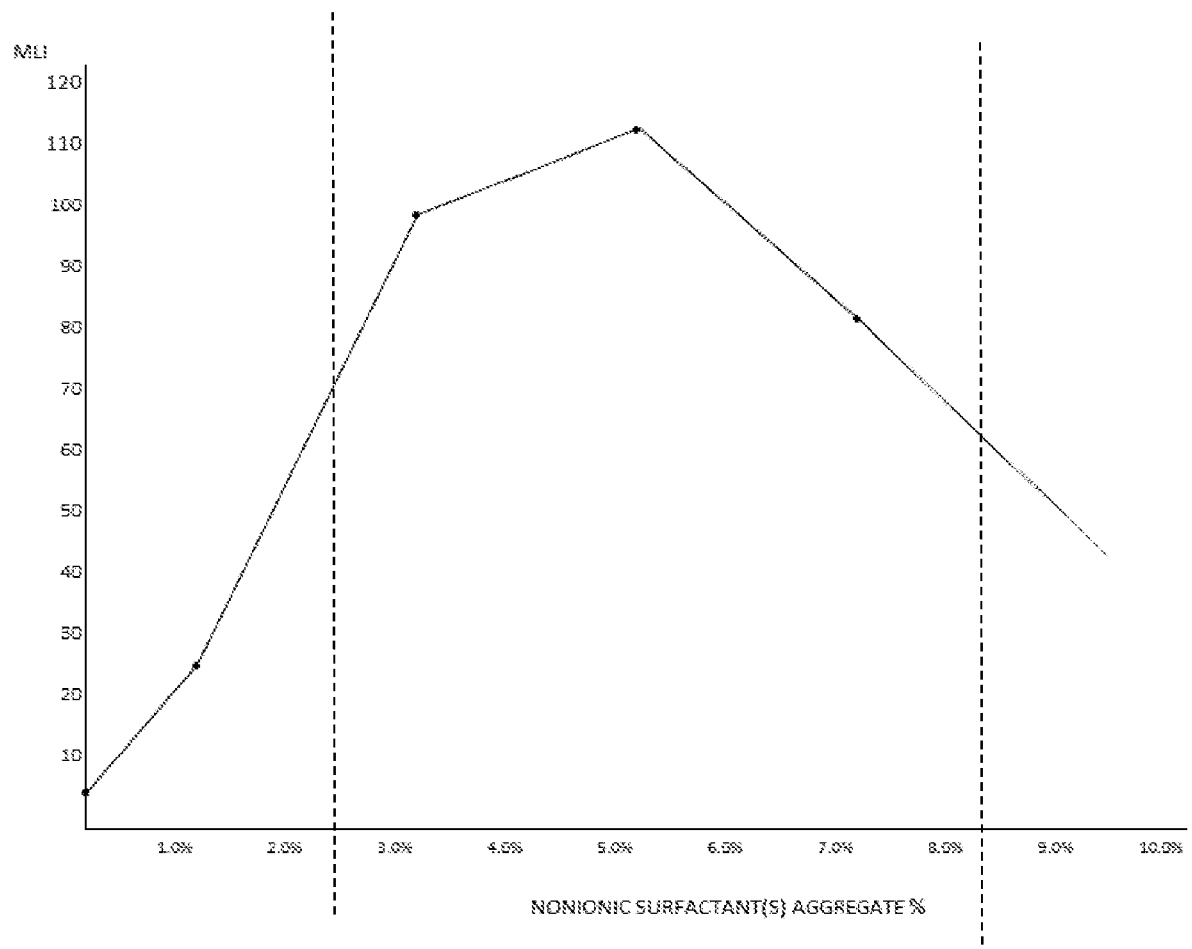
FIG. 1. Graph of Moisture-Lock™ Index versus nonionic surfactant concentration. Moisture-Lock is a trademark owned by PS Therapies, Ltd.

The present invention is directed to the surprising discovery that artificial tears can be formulated to cover a sufficient surface area of the eye to create an evaporative tear shield that can stabilize the aqueous and lipid layers of the tear film without the addition of lipids. Particularly surprising is the discovery that total concentration of nonionic surfactants may be increased in the presence of the compositions of the present invention to well above 1.0% w/v, which has been demonstrated as toxic in prior art ophthalmological preparations. Even more surprising is that compositions of the present invention with total nonionic surfactant concentrations up to 7.0% w/v may be routinely instilled in the eye without toxicity. Further, compositions of the present invention surprisingly cause an evaporative tear shield to form and can be formulated to induce natural tearing that is maintained under this evaporative tear shield. The discovery of such compositions is novel because present artificial tears that include lipids do not create an evaporative tear shield and leave an oily, unnatural feeling. Further, the artificial tear compositions of the present invention stabilize the lipid layer of the tear film as well as stabilize and spread the aqueous layer. Components of all three layers of the tear film are critical to successful tear function. Finally, the shape of the nano-micelles formed by the artificial tear compositions of the present invention provides an improved barrier to evaporation by covering a substantial portion of the surface of the eye. These nano-micelles may be from about 12 to about 20 nanometers in diameter, from about 12 to about 14 nanometers in diameter, from about 15 to about 20 nanometers in diameter or about 19 nanometers in diameter.

In detail, the presence of the nano-micelle layer, created using nonionic surfactants at a particular concentration range, consists of a nonpolar and a polar surface. This dual surface allows compositions of the present invention to not only stabilizes the natural lipid and aqueous layers of the tear film, but also create an evaporative barrier. The nano-micelle layer finds its preferred lowest energy level when against any hydrophobic surface by spreading along that interface. Hydrophobic surfaces of the eye include both the original tear lipid layer and the air-tear interface. Perhaps most important is the effect provided by these specific interactions. Specifically, the 1) nonpolar seal, 2) polar and nonpolar stabilization of lipid and aqueous layers, 3) improved spreadability per blink, and 4) greater tear film prism provided by the compositions of the present invention create what is called the Moisture-Lock™ effect. The Moisture-Lock™ effect can be quantified somewhat with tear volume analysis via Schirmer's strip measurement or phenol thread. However, these tests are notoriously difficult to use accurately due to the many environmental variables including reflex tearing that can compromise these measurements. A more accurate representation of the effect is a qualitative measure of the duration of added wetting felt. This has been found to be particularly sensitive to the particular combination of nonionic surfactant component(s) of the present invention, and more particularly to the total concentration of nonionic surfactants. Further, the viscosity of the composition and additional excipients play an important role in the present invention for a range of conditions that require these variables to be customized. However, analyzing the Moisture-Lock™ effect with these variables fixed produces a well-defined range where the Moisture-Lock™ effect occurs. See Example 1 below.

The Moisture-Lock™ effect results from any natural secretion of tear components and particularly aqueous components being sealed under the nano-micelle layer created by compositions of the present invention. Such sequestration creates prolonged contact of critical aqueous factors resulting in great therapeutic and comfort benefits, much like found with blood serum eye drop application. It has been discovered that a mild to extreme degree of the Moisture-Lock™ effect may be triggered by creating even slight tearing, such as by adjusting pH or osmolarity, which then becomes amplified by the tear sequestration property of the present invention.

Equally important, the concentration ranges and unique combinations of particular nonionic surfactants utilized in the present artificial tear compositions dissolve lipids that would otherwise plug Meibomian ducts. Meibomian ducts are responsible for secreting components of the natural tear that reduce tear evaporation. This clinical condition, known as Meibomian gland dysfunction, plagues not only many dry eye patients, but is a common affliction of glaucoma patients and others that must continually use eye drops.

Artificial tear compositions of the present invention also, stimulate secretion of the aqueous component of the natural tear. The evaporative shield created then prevents evaporation of this natural aqueous layer in what is felt by the patient as the Moisture-Lock™ effect. The net effect of the stimulation of the natural tear, in combination with the ability to sequester it, may provide greater additional exposure of the eyes to natural tear elements than that provided by prescription medications such as Restasis® and Xiidra® (Restasis is a registered trademark of Allergan, Inc. and Xiidra is a registered trademark of SARcode Bioscience Inc.). In clinical studies, Restasis® and Xiidra® have each been found to only marginally enhance tear production with mixed clinical results in treatment of dry eye (i.e. 50% or less benefit requiring many months and often not or only marginally clinically significant over conventional artificial tears).

Compositions of the present invention provide an extensive shield that seals in natural tear production via the discovered means of tear sequestration. Even the slightest trigger of natural tearing, which may be induced by pH adjustment, osmolarity adjustment, or addition of components such as menthol, may create an amplified benefit of the present invention by exposing the eye to greater volumes of natural tears. This tear volume exposure is greater than that provided by Restasis® or Xiidra®, which increase tear volume by natural tear secretion only. Further, these topical medications are prescription in nature and extremely costly at as much as $300 per month. However, the present invention discovers novel means of combining generally regarded as safe ingredients to formulate an artificial tear composition with truly surprising and unexpected results over these prior art formulations.

Artificial tears are traditionally an external source of lubrication for the eye. However, the present artificial tear compositions further seal in natural tears for prolonged contact and wetting of the surface of the eye exposing the eye to growth factors, lysozymes, and other tear constituents that help heal and protect the eye. Not wishing to be held to a particular theory, the protective shield provided by the present artificial tear compositions decrease tear wetting angle with formation of large tightly packed nano-micellar structures sealing the entire surface area and providing the unexpected result of a Moisture-Lock™ effect. This effect has not been possible with any previous generation of artificial tear. The Moisture-Lock™ effect is equivalent to triggering natural tear synthesis for prolonged periods of time and possibly more substantial than plugging the punctal duct. Punctal duct plugging sequesters any tears a dry eye patient releases with reduced frequency and or less effectively than compositions of the present invention. Further, compositions of the present invention nominally trigger, sequester, and restrict tear drainage in the eye with only zero to tens of seconds of visual blur even for the most extreme viscosities, which are only necessary for the most extreme therapeutic needs. This is in stark contrast to prior art formulations, which for example at 400 centipoise requires ten or more minutes of visual blur to stabilize.

In a preferred embodiment, the present invention is directed to artificial tear compositions comprising one or more nonionic surfactants and an electrolyte such that the compositions achieve desired fluid flow and non-Newtonian (nonlinear vs. lid shear) viscosity properties that are dramatically affected by electrolyte concentration and optimized by electrolyte concentrations that are preferably hypo-osmolar.

In another preferred embodiment, the present invention is further directed to an artificial tear composition capable of increasing duration of the artificial tear composition on the eye and stabilizing the natural aqueous and lipid layers. Preferably, the composition further increases duration of exposure of the eye to the stabilized natural aqueous layer including growth factors, antimicrobial factors, and other proteins and nutritional elements.

The benefits incurred from this prolonged exposure to the aqueous layer is currently possible only by spinning down blood and storing blood plasma or platelet rich plasma followed by topical instillation to the eye. The benefits from this prolonged exposure to the natural aqueous layer may be partially assessed by measure of the tear breakup time. However, tear breakup time is an antiquated means to quantify tear function and has less clinical relevance than the actual amount and duration of exposure of the corneal epithelium to the nutritional rich aqueous layer. Commercially, the leading market dominating formulations (Allergan® Refresh® product line) demonstrate the most refreshing sensation of added moisture rather than a synthetic oily feeling. For the present invention, a 'Moisture-Lock™ Index' described in Example 1 below better correlates with extent and duration of this important sensation for an artificial tear to be most tolerated and desired.

In another preferred embodiment, the present invention is further directed to a method of treating dry eye comprising administering a composition of the present invention to an eye of a subject in need thereof, wherein administration provides sequestration of a tear layer under a nonionic surfactant layer and preferably, wherein the nonionic surfactant layer allows the retention of the aqueous layer via the hydrophobic outer layer aligning with the hydrophobic lipid layer or air. This layer is impervious to water permeation and provides a hydrophilic opposing surface. This opposing surface stabilizes the aqueous layer, and results in the aqueous constituents of normal and induced tears, as well as the therapeutic constituents of the present invention such as the polyol and the electrolytes to maintain prolonged contact with the eye.

A further advantage of the present invention is the surprising discovery that addition of viscosity enhancers, particularly cellulose derivatives, carbomers, gums, dextrans, polyvinyl alcohol, polyacrylic acids, povidone, polyethylene glycol, propylene glycol, chitosans, and hyaluronates and hyaluronic acids, provides a low shear non-Newtonian high viscosity between blinks and high shear low viscosity during blinks. The low shear viscosity between blinks helps spread the present artificial tear compositions over the eye and the high shear viscosity during blinks prevents the break up and drainage of the evaporative shield. Thus, the ability to change in viscosity helps amplify the Moisture-Lock™ effect by strongly retarding tear evaporation and drainage. Further, the addition of particular viscosity agents of the present invention provides a viscosity of 300-400 centipoise ("cps") on instillation, yet within 60 seconds no longer result in visual blur. Further, these viscosity agents provide a differential of about 70 cps between blinks (low shear conditions) and below 30 cps, preferably below 20 cps, during each blink (high shear conditions.) This is about ten times quicker than the vision recovery of similarly viscous conventional drops such as Refresh Celluvisc®.

A still further discovery of the present invention is inclusion of a polyol and electrolytes that may protect the surface of the eye and facilitate healing. These additional excipients may also reduce effects of preservative toxicity from other prescribed drops such as antibiotics, steroids, nonsteroidals and or glaucoma drops. The present invention discovers that concentrations of polyols above about 0.5% w/v and, particularly, above about 1.25% w/v are preferred.

In summary, surprising discoveries of the compositions of the present invention include:

i) creation of a nano-micellar layer with sufficient surface coverage to provide a substantial evaporative shield by utilizing nonionic surfactant concentrations above the critical micellar concentration of $10^{-3}$ M to $10^{-4}$ M from about 1.5% to about 7.0% w/v and preferably less than about 5.5% w/v;

ii) dissolution of lipids and or lipid deposits on the surface of the eye or contact lens by adding a polyoxyl at greater than about 0.005% w/v but less than about 0.20% w/v, and more preferably from about 0.01% to about 0.10% w/v, and most preferably adding polyoxyl castor oils;

iii) provision of a composition that has high viscosity on instillation that quickly equilibrates to normal tear viscosity and then fluctuates between normal and high viscosities between and during blinks, respectively, by adding particular viscosity agents thus reducing vision blur and prolonging the duration of the composition on the eye; and iv) provision of additional benefits including possible improvement in nerve regeneration and epithelial healing by adding a polyol and magnesium ions in the form of salts.

Prior to the present invention, nonionic surfactants were used at very low concentrations in artificial tears or as storage/soaking solutions for contact lenses. It was thought that the use of nonionic surfactants at the concentration ranges of the present invention was too toxic for topical application. It is a discovery of the present invention that the inclusion of the unique combination of nonionic surfactants at a total concentration from about 1.25% to about 7.0% w/v, preferably from about 1.5% to about 6.0% w/v, from about 2.8% to about 5.9% w/v, from about 2.0% to about 4.0% w/v, and from about 3.0% to about 3.5% w/v, a polyol at a concentration of about 0.5% w/v or greater, and a viscosity agent providing a viscosity of 10 cps or greater, prevents toxicity.

Several over-the-counter ("OTC") drops provide an external source of lipid components of the natural tear. These drops include: Soothe® XP (Soothe is manufactured by, available from and a registered trademark of Bausch & Lomb Incorporated) and Retaine® (Retaine is manufactured by, available from and a registered trademark of OcuSoft, Inc.), which each contains light mineral oil and mineral oil; Systane Balance® (Systane Balance is manufactured by, available from and a registered trademark of Alcon, Inc.), which contains propylene glycol; and Refresh Optive® Advanced (Refresh Optive is manufactured by, available from and a registered trademark of Allergan, Inc.), which contains carboxymethyl cellulose sodium, glycerin and polysorbate 80.

These OTC tear formulations have the disadvantage of: 1) minimal nonionic surfactant stabilization of the natural lipid layer, 2) minimal reduction of wetting angle to enhance spreading of the aqueous layer, 3) insufficient nonionic surfactant for the discovered advantages of improved nano-micelle geometries and 4) required surface area coverage for evaporative shield protection.

It has been surprisingly discovered that the compositions of the present invention create a "welling of tears" for prolonged periods of time, reflected in creation of a large tear prism thickness along the lower lid margins. Without wishing to be held to a particular theory, it is believed natural and, in some compositions, induced tearing remains sequestered under a low evaporative nanomicellar robust shield creating an increased thickness of the aqueous layer and stabilized lipid layer. The sensation is further enhanced in most compositions of the present invention by the nonlinear (non-Newtonian) viscosity with increased interblink thickness and very low wetting angle, so that tears tend not to cross the hydrophobic air interface or run down the cheeks despite the larger tear prism along the lid margins. Where conventional tears may produce some additional comfort and lubrication for 10-20 minutes, the disclosed invention results in a novel sensation for an hour or longer. This novel sensation is the feeling of trapped tears, resulting from the lining of both lids flooding with moisture to the extent of an overflow onto the lid margin for as long as 60 minutes. As a result, a unique phenomenon of prolonged trapping of tears, with great therapeutic potential consequence and an extremely refreshing sensation for a dry eye patient of a "welling of tears" is produced. This phenomenon, herein hereafter referred to as the Moisture-Lock™ effect and is measured by the Moisture-Lock™ index.

It is believed that the total nonionic surfactant concentration range creates a micellar layer that becomes sufficiently packed to dramatically cover the ocular surface and spread at an extremely low wetting angle acting like a lipid and aqueous stabilizer. This layer also spreads along the air or lipid hydrophobic interface aligning the nonpolar ends to create a robust non-evaporative surface. It is surprisingly discovered that at a critical concentration above the critical micellar concentration ("CMC") of the added nonionic surfactant(s) there is therein created a concentration micelle trigger ("CMT"), which triggers confluence or near confluence along the ocular surface and reduced evaporation without needing the addition of lipids that give a synthetic oily feeling. Further, this CMT is surprisingly discovered to occur in a range which is about 15 to 600 times above each of the CMCs of the nonionic surfactant(s) resulting in the discovered non-evaporative shield and the resultant Moisture-Lock™ effect. This effect is maintained to a peak within this range and at an upper concentration limit ("CUL") begins to have surface toxicity as well as reduced effect. This reduced effect is possibly a result of a change in the geometric configuration of the micellar layer(s).

It is believed the micellar layer at or above the CMT provides a concentration range with the CUL as its upper limit within which a coating/shield effect results with two or more of several observed novel properties:

i) creation of an evaporative shield causing reduced evaporation of the tear layer and less sensitivity to humidity, tear volume, or the tear breakup time, (tear breakup time is determined by tear chemistry driven beading vs. time and is a difficult variable to measure accurately because it is influenced by irritation and other factors);

ii) providing extremely low surface tension for most immediate coverage of the corneal surface and any dellen (i.e. irregular topography along the corneal epithelium that creates dry spots);

iii) a non-Newtonian fluid flow resulting in substantial stasis between blinks and easy flow during blinks primarily along the high shear vertical component of that blink, such that lacrimal drainage is minimized and tear film coverage along the corneal surface is optimized with recycling on each blink until the lid cul de sac depot of novel tear fill becomes slowly depleted;

iv) no blur at lower viscosities and only slight blur for about 15 seconds or less even at viscosities as high as 400 cps, whereas conventional tear products (Liqui-gel® 150 cps, Celluvisc® 400 cps) result in blurred vision for about a 10 to 20-minute range, respectively, thus providing benefits above and beyond very viscous tear substitutes of conventional tear formulations with the comfort and vision of very minimally viscous conventional tears;

v) sequestration, meaning an apparent "trapping" of produced tears under the non-evaporative shield unlike that found in conventional tears that results in a "welling up" effect along the lid margins for tens of minutes, and under conditions of added viscosity agent with enhanced nonlinear non-Newtonian shear effect of as much as an hour or longer, with provision of prolonged contact of human tear constituents with the corneal epithelium;

vi) sequestration as in v above of induced natural tears, particularly in preferred embodiments where low pH, altered osmolarity, or addition of excipients such as menthol result in such induction and long duration retention;

vii) added comfort, epithelial protection, and enhanced milieu for regenerative epithelial surface integrity by the addition of excipients in the form of a polyol and or magnesium ions;

viii) a coating that once placed on a contact lens before insertion provides a long-lasting coating effect that reduces deposits on the contact lens surface and enhances vision on instillation and facilitates improved comfort when instilled during wear, particularly at least 16 hours after instillation of the contact, thus reducing epitheliopathy, with minimal tear dispersion surprisingly discovered for at least 24 seconds compared to a normal tear breakup at 8 seconds;

ix) protection from saponification, as occurs in Meibomian gland dysfunction, reducing the accumulation of lipid deposits that stick to the palpebral conjunctiva and are difficult to remove, as well as irritating moieties within the tear film, including but not limited to cholesterol esters, preservatives from other drops that may be concomitantly prescribed or required for treatment of other conditions—such as particularly antibiotics, nonsteroidals, steroidals, and glaucoma topical medications; and x) a cumulative effect from the combination of two or more of noted features above that improves comfort and health of the corneal surface, allowing growth factors from tears to provide prolonged beneficial protection and healing benefits for a variety of external surface related physiologic stresses and disease states.

Not wishing to be held to a particular theory, it is believed that most nonionic surfactants available for ophthalmic use including, but not limited to, polysorbate 20, 60, and 80; tyloxapol, poloxamer 188 and 407; polyoxyl 30 and 40 castor oil; cyclodextrins including hydroxypropyl-gamma-cyclodextrin, gamma cyclodextrin, Brij® 35, 78, 98, and 700 (polyoxyethyleneglycol alkyl ethers; Brij is a registered trademark of Uniqema Americas LLC); Span®20, 40, 60, and 80 (sorbitan monolaurate, sorbitan monopalmitate, sorbitan monostearate, and sorbitan monooleate; Span is a registered trademark of Uniqema Americas Inc.), or combinations thereof in the concentration range of about 1.5% to about 5.5% w/v and where the critical micellar threshold ranges from about $1\times10^{-3}$ M to $1\times10^{-4}$M, have been discovered to result in important characteristics such as:

i) lowest energy geometries via layering due to the juxtaposition of hydrophobic surfaces upon instillation onto the eye—from closest to furthest from the ocular surface being epithelium, lipid layer and air interface;

ii) lowest energy geometries via layering due to juxtaposition to one or more hydrophobic surfaces upon instillation onto the eye to which they may be exposed including: corneal and conjunctival epithelium, natural lipid tear film layer and air interface, or similarly become so densely packed as to effectively function as a protective shield, or coating;

iii) sufficient density within the preferred concentration range that when layered or densely packed on top of the aqueous layer it retards evaporation significantly; iv) smoothing out of the lipid layer to retain a smoother more uniform surface and dissolving Meibomian gland lipids to further increase its thickness;

v) superior spreadability due to the low surface tension and wetting angle and coating of the epithelial surfaces with each high shear blink, particularly dellen (elevated regions of corneal topography tear film may not coat evenly or at all);

vi) providing one or more nonionic surfactants whereby each of the above functions may be facilitated by different surfactants, and where the concentration range of about 1.5% to about 5.5% w/v represents the aggregate summation of individual surfactant concentrations; and vii) where polyoxyls and particularly polyoxyl castor oils may preferentially solubilize Meibomian gland secretions.

A further surprising discovery of the present invention is the prolonged Moisture-Lock™ effect of even mild hyperosmolarity, such as provided by increasing concentrations of the electrolyte to about 0.20% w/v or above. In particular, sodium chloride is preferred for this purpose. It is believed the very gentle but slight irritation created by a hyperosmolar tear triggers an initial increase in tearing, which becomes "locked" under the micellar layer. This tear secretion is then further sealed by non-Newtonian flow properties providing valuable inotropic growth factors and other nutrients and physiologic components to the surface of the eye. These non-Newtonian flow properties provide sealing by limiting lacrimal drainage via increased viscosity at the low shear between blinks while improving visual acuity by the low viscosity triggered at the high shear during a blink.

An additional surprising finding is the novel discovery that a polyol, particularly mannitol, and or magnesium ions, and particularly the combination provide protection of the corneal surface from epitheliopathy, including but not limited to the effects of preservatives and or antioxidants.

An additional unexpected finding is that the addition of an antioxidant adds increased duration of effect. This discovery is surprising in light of the long-held tenet that tear formulation antioxidants, particularly EDTA, cause epithelial toxicity.

Variations in the a) concentration, particularly of viscosity agent(s), b) epithelial protective excipients such as polyols such as mannitol and c) addition of electrolytes particularly magnesium ions and NaCl provide a means to titrate duration of wetting effect (i.e. Moisture-Lock™ effect), degree of initial blur (i.e. from about 0 to 15 seconds), and a range of other effects including protective and therapeutic effects. This variability of compositions of the present invention allow treatment of a range of conditions.

Certain conditions, such as meibomian gland dysfunction ("MGD") may benefit from lid massage and oil expression techniques, such as a cotton ball roll along the lid margins. These conditions may also benefit from the robust nonionic surfactant surface layer created in the CMT range for the total nonionic surfactant concentration (i.e. from about 1.5% to about 5.9% w/v, more preferably from about 2.5% to about 4.0% w/v). Where increased concentrations of particular nonionic surfactants such as polyoxyls, preferably polyoxyl castor oils, and most preferably polyoxyl 30 or 40 castor oil at a concentration from about 0.001% to about 2.0% w/v, and more preferably from about 0.010% to about 1.0% w/v may further enhance such formulations for treatment of MGD. It is additionally discovered that addition of a polyethylene glycol oil enhances the stability of the composition.

The present invention combines a high degree of mucoadhesiveness and temperature sensitive alteration in rheological properties between and during blink. These rheological properties allow for physiologic blinking without blur, and after equilibration, within about 15 to 60 seconds depending on the embodiment selected, creates a thin tear film of about 5-10 μm. It has been surprising that the present invention:

a) creates prolonged wetting and hydration typically of about one hour or longer;
b) creates minimal blur on instillation of tens of seconds, typically 30 seconds or less (See Table 2 above);
c) produces no crusting of lids or lashes, only a prolonged wetting action felt along lid margins;
d) allows comfortable instillations at very low (less than 4) or high (greater than 7) pH;
e) provides prolonged tear sequestration and exposure to induced (Moisture-Lock' effect) and natural tears via the robust hydrophobic barrier of the nonionic surfactant layer (See Table 13 and FIGS. 1 and 2); and
f) provides potential for equal or greater incremental tear exposure to the ocular surface than current generation prescription dry eye products Restasis® and or Xiidra®, which demonstrate only marginal incremental increase in tear secretion.

Excipients of the present invention that may reduce epithelial toxicity include one or more of polyols and electrolytes, where it is surprisingly discovered that the combination of nonionic surfactants of the present invention is further enhanced by from about 0.10% to about 2.00% w/v NaCl, more preferably from about 0.20 to about 2.00% w/v, and most preferably from about 0.25% to about 2.00% w/v. Normal isotonic solutions would typically require 0.90% w/v NaCl. A second electrolyte in preferred embodiments is magnesium ions. In a more preferred embodiment, the source of magnesium ions is $MgCl_2$. In an even more preferred embodiment, the $MgCl_2$ is at a concentration from about 0.01% to about 0.25% w/v, more preferably from about 0.05% to about 0.15% w/v, and most preferably from about 0.075% to about 0.125% w/v. The polyol is preferably mannitol and more preferably mannitol is at a concentration from about 0.25% to about 4.0% w/v, even more preferably from about 0.75% to about 4.0% w/v, more preferably from about 1.5% to about 4.0% w/v. Not to be held to a particular theory, it is believed these excipients, alone or in combination, enhance epithelial healing, recovery of injured neuronal components, reduce pain, promote quicker epithelial surface smoothing and health, and reduce or eliminate superficial punctate keratopathy. Superficial punctate keratopathy is a common ocular surface abnormality from exposure to irritants. These irritants are particularly preservatives found in most eye drops including antibiotics, steroids, nonsteroidals, and glaucoma drugs. Accounting for toxicity after cataract surgery due to these irritants and for those on medications for chronic eye diseases, such as glaucoma, the compositions of the present invention may considerably alleviate associated symptoms.

The present invention benefits from a total surfactant concentration of at least 1.0% w/v, preferably from about 1.0% to about 10% w/v, more preferably from about 1.0% to about 5.9% w/v, even more preferably from about 1.5% to about 5.9% w/v, even more preferably from about 2.5% to about 5.5% w/v, and most preferably from about 3.0% to about 5.0% w/v, where the nonionic surfactant or nonionic surfactants each have a critical micellar concentration (the concentration at which micelle formation occurs and surface tension is no longer reduced) in the range of $10^{-3}$ to $10^{-4}$M. The nonionic surfactant may consist of one or more of cyclodextrins (where hydroxy propyl gamma cyclodextrin, gamma cyclodextrin, and beta cyclodextrin are most preferred); polyoxyl sorbates, including all Tween® sorbates (polysorbates; Tween is a registered trademark of Uniqema Americas, LLC), including Tween® 80, 60, 40, or 20; other polyoxyls (most preferred being polyoxyl castor oils and polyoxyl stearates); alkyl aryl polyethers (most preferred being tyloxapols); alkyl ethers including all Brij® alkyl ethers (most preferred being Brij® 35, 78, 98, and 700; Span® 20, 40, 60, and 80 (sorbitan monolaurate, sorbitan monopalmitate, sorbitan monostearate, and sorbitan monooleate) and tocopherols (Vitamin E).

The non-Newtonian viscosity component is increasingly important proportional to the clinical need for treatment of a dry eye or dry eye related condition. The non-Newtonian viscosity component is especially important in the absence of an inserted device including contact lenses and punctum plugs. The non-Newtonian viscosity component provides reduced tear drainage between blinks when the viscosity is at more than about 30 cps, preferably from about 35 to about 50 cps, and most preferably from about 70 to about 400 cps between blinks; and during each blink less than about 30 cps, preferably less than about 25 cps, and most preferably about 20 cps or less. In a preferred embodiment, the non-linear shear viscosity ratio is from about 5:1 to about 10:1 interblink to blink viscosity. Surprisingly the combination of nonionic surfactant in the preferred range and viscosity agents at low (less than about 20 cps or up to about 500 cps) creates a surprising equilibration of vision at high viscosity and improved flow properties. Commercial high viscosity tear formulations such as Refresh Celluvisc®, also at 400 cps have been shown in numerous studies to require 10-15 minutes to equilibrate to normal vision, over ten times longer than the surprising discovery of preferred nonionic surfactant(s) and viscosity agents between 10 cps and 500 cps of the present invention. Viscosity agents for preferred embodiments of the present invention including, but not limited to, cellulose derivatives such as HPMC, HPC, HPEC and CMC; Carbopol® compounds such as Carbopol® 90 and 940; hyaluronates; and gums such as guar and locust gums.

It is a surprising discovery of the present invention that application of preferred embodiments, particularly formulations utilizing polysorbates, poloxamers, polyoxyls or cyclodextrins alone or in combination with each other and or other nonionic surfactants have properties of optimized tear film moisture retention. See FIG. 1. Even more unexpected, use of viscosity agents, particularly cellulose agents and or their derivatives, and more particularly hydroxypropyl methyl cellulose or carboxymethyl cellulose or carbomer 940 dramatically enhance tear film moisture retention and even at resting low shear viscosities in their packaged delivery bottle or unit dose tube as high as 200-400 cps have only transient blur of a few seconds to under 30 seconds. This tear film moisture retention is known herein as Moisture Lock™. It is still more surprising that storing of soft contact lenses, including but not limited to those consisting of silicone and or hydrogel polymers, in blister packs, or other packaging that retains a liquid, with compositions of the present invention results in a substantial adherence of the composition to the contact lens surface reducing deposits. Once these contacts that were stored in the compositions of the present invention are placed on the eye of the subject the composition greatly increases tear break up times while reducing tear dispersion. This adherence creates a strongly bonded non-evaporative coating that stabilizes the tear film, increases comfort and provides an optional dry eye therapy even for contact lens intolerant subjects.

Artificial tear compositions 36-57 of Table 2 and 58-89 of Table 3 offer superior wetting and Moisture-Lock™ effect over artificial tear compositions 1-35 of Table 2. This superior effectiveness is hypothesized to be caused by the unique combination and concentrations of nonionic surfactants. Further, the addition of a polyol and magnesium ions to compositions 36-57 is hypothesized to further enhance wetting and Moisture-Lock™ effect over those compositions that do not contain a polyol and magnesium ions.

There clearly appears to be surprising effects within the combinations, concentrations and ratios of the invention. Particularly nonionic surfactant ranges and combinations, in relation to viscosity, electrolytes and protective excipients such as a polyol and magnesium ions provide surprising effects. Particularly surprising is the relation of electrolytes to final viscosity, blur or lack thereof, and comfort. Preferred embodiments result in increased tear film stability, prolonged Moisture-Lock™ effect and welling up of the aqueous layer from many tens of minutes to up to one hour with a single drop. Relative to the viscosity there is reduced time of blurred vision when compared to current artificial tears and more prolonged and clinically improved effect for a great variety of conditions.

Ophthalmological Drug Vehicles

A further surprising discovery of the present invention is that ophthalmological drugs added to the present invention increase duration of the drugs on the surface of the eye, increase permeation across the cornea, and reduce systemic absorption, creating an ideal platform vehicle for drug delivery while reducing dry eye symptoms and irritation that might otherwise occur for many such active agents such as non-steroidals, antibiotics, and glaucoma drugs. This drug vehicle may be particularly useful for enhancing the therapeutic duration and benefits of cyclosporine-A currently found in Restasis®. These compositions may be capable of formulating up to 0.09% and from about 0.05% to about 0.09% cyclosporine-A without the need to create an emulsion. In a preferred embodiment, the cyclosporine-A drug vehicles of the present invention may not contain emulsifiers. The cyclosporine-A drug vehicle of the present invention provides from about 12 to about 20 nanometer diameter nano-micelles. Further, the cyclosporine-A drug vehicle of the present invention delivers suffusion of tears for up to 60 minutes.

A further surprising discovery of the present invention is the suppression of preservative toxicity effect resulting from one or more of preservatives in the presence of the present invention, particularly therapeutic excipients such as a polyol and or magnesium ions. This discovery is surprising in light of the long-held tenet that tear formulation preservatives cause epithelial toxicity and is potentially of great importance as many chronic use ophthalmic drugs, such as for glaucoma, or inflammation are compromised by the accrued effect of induced epithelial toxicity often limiting their duration of use.

A further surprising discovery of the present invention is the sustained release of a drug. The peak concentration of the drug can be increased about 50% in duration, (e.g. from 2 to 4 hours).

Topical Compositions and Drug Vehicles

It is further discovered that compositions of the present invention may be used in topical compositions such as anesthetic gels, as an anti-adhesion for prevention of scarring, in implantable devices, in time-release impregnated bandages, in parenterals, in inhalers, in sprays, in topical lotions, in topical gels, in topical liquids, in anti-aging skin products such as day and night product and under eye products, in sunscreens, in body wash, in therapeutic shampoos, in antiperspirant, for stretch marks, in shaving creams, as a blade glide coating, in OTC lidocaine compositions, in OTC cortisone compositions, in analgesic compounds such as Ben-Gay®, in treating hemorrhoids, for treating acne, in collagen-based products, in retinal-based products, for treating dry skin, for treating dermatitis, psoriasis, for reducing or eliminating scars or port wine stains, for enhancing hair growth, as a non-irritating hair dye and for facial wasting disease.

It is unexpected that the ophthalmological compositions of the present invention could be used for prevention, treatment and minimization or eradication of aging and other imperfections in the skin. However, the administration and use of a nanomicellar nonionic surfactant composition with a physiologically based pH, as disclosed herein, has the benefit of providing a cleansing, mildly exfoliating and reparative moisturizing effect on facial tissue. The effect can deliver, based on a prescribed treatment regimen, visible improvement in the areas of managing fine to moderate wrinkling, lightening and size reduction of sun, age and/or liver spots on the skin.

The long-term moisturizing effect that penetrates the top skin layers can also provide long term hydration for the skin which maintains skin tone and texture. Further contemplated are eliminating of common blemishes, reducing skin thickness (supporting use on scar removal over time), improving dry skin as well as elasticity and collagen. Further contemplated as a use for the compositions of the present invention is maintenance of normal pore size as well as the increase in hydration, which can also increase the tightness of the facial skin, thus improving the overall smoothness.

The compositions of the present invention may comprise droplets, and these droplets may comprise an aqueous phase, at least one oil, a mix of four or more nonionic surfactants, at a specific concentration range, in a topically applied lotion or other compatible and pharmaceutically accepted forms. In mild cases, this base composition may be used as the sole treatment method for the skin. However, in more severe cases, the highly compatible base formula can be combined with any of the known active drug substances, such as Botox®, retinoids, and any other proven topical treatment. Specifically, the specific nonionic nanoparticles enhance permeation into the top layers of the skin, which enhances efficacy.

Within the liquid cleanser category, the least irritating cleanser will contain non-ionic/silicone-based surfactants combined with moisturizers, as they will cause the least disruption to the moisture skin barrier and the normal skin flora. While this describes cleanser qualities, these same benefits, plus some new findings, indicate that use after cleansing provides benefit to a patient's skin conditions and, when used as directed, can effectively manage a host of dermatologic conditions that would otherwise negatively affect self-esteem and social acceptance. It is a discovery of the present invention that most issues surrounding aging skin can be effectively managed by the nonionic surfactant alone or when combined with a specific active drug treatment used on the skin.

Definitions

As used herein, the term "composition" is intended to encompass a product comprising the specified ingredients in the specified amounts, as well as any product which results, directly or indirectly, from a combination of the specified ingredients in the specified amounts.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "subject" refers but is not limited to a person or other animal.

Throughout the application, the singular forms "a," "an," and "the" include plural reference unless the context clearly dictates otherwise.

As used herein the term "polyol" refers to compounds with multiple hydroxyl functional groups available for organic reactions such as monomeric polyols such as glycerin, pentaerythritol, ethylene glycol and sucrose. Further, polyols may refer to polymeric polyols including glycerin, pentaerythritol, ethylene glycol and sucrose reacted with propylene oxide or ethylene oxide.

As used herein the phrase "means for inducing tears" includes any means by which production of natural tears may be induced in the subject to which the compositions of the present invention are applied. Preferably, tears may be induced by modifying the pH of the composition to a range from about 5.0 to about 6.0, modifying the osmolarity of the composition to a range from about 350 to about 550 milliosmoles and or including a terpenoid, such as menthol.

As used herein the phrase "means for sequestering tears" includes any means by which natural tears induced by the compositions of the invention and the artificial tears compositions of the invention may be sequestered on the eye. Preferably, a combination of particular concentrations and types of nonionic surfactants and particular concentrations and types of viscosity enhancers are used as the means for sequestering tears.

Ingredients of the Invention

Nonionic surfactants that can be used in accordance with the present invention include, but are not limited to, poloxamers, polysorbates, cyclodextrins, alkylaryl polyethers, polyoxyethyleneglycol alkyl ethers, tyloxapol, and polyoxyls. Poloxamers are nonionic triblock copolymers composed of a central hydrophobic chain of polyoxypropylene (poly (propylene oxide)) flanked by two hydrophilic chains of polyoxyethylene (poly(ethylene oxide)). Polysorbates are oily liquids derived from ethoxylated sorbitan esterified with fatty acids. Cyclodextrins are composed of 5 or more α-D-glucopyranoside units linked together at position 1 and 4. Polyoxyls are a mixture of mono- and diesters of stearate and polyoxyethylene diols. Preferred embodiments include but are not limited to poloxamers-poloxamer 188 and poloxamer 407; polysorbates-polysorbate 20, polysorbate 60, polysorbate 80, tyloxapol, Brij® 35, Brij® 78, Brij® 98 and Brij® 700, Span® 20, Span® 40, Span® 60, Span® 80; cyclodextrins-2-HP-cyclodextrin, ionically charged (e.g.

anionic) beta-cyclodextrins with or without a butyrated salt (Captisol®; (sulfobutylether β-cyclodextrin, Captisol is a registered trademark of Cydex Pharmaceuticals), hydroxypropyl-gamma-cyclodextrin, gamma cyclodextrin; and polyoxyls-polyoxyl 40 stearate, polyoxyl 30 castor oil, polyoxyl 35 castor oil, and polyoxyl 40 hydrogenated castor oil; or combinations thereof. Polyols are not included in the term "nonionic surfactants." Total nonionic surfactant concentrations of the present invention are from about 1.0% to about 7.0% w/v, preferably, 1.5% to about 7.0% w/v, preferably from about 1.5% to about 6.0% w/v, more preferably from about 1.5% to about 5.9% w/v, more preferably from about 1.5% to about 5.5% w/v, more preferably above about 2.0% w/v and less than 6.0% w/v, from about 2% to about 4% w/v, more preferably from about 2.5% to less than about 5.9% w/v, more preferably from about 2.5% to about 5.5% w/v, more preferably from about 2.5% to about 3.5% w/v, more preferably from about 2.8% to about 5.9% w/v, more preferably from about 3% to about 5% w/v, more preferably from about 3% to about 3.5% w/v.

In preferred embodiments, the one or more nonionic surfactants include a polysorbate, such as polysorbate 80.

In more preferred embodiments the amount of polysorbate is from about 0.01% to about 4.0% w/v, preferably from about 0.5% to about 3.5% w/v, preferably about 0.5%, 1%, 1.5%, 2%, 2.5%, 2.75%, 3% and 3.5% w/v.

In other preferred embodiments, the one or more nonionic surfactants include a poloxamer such as poloxamer 188 and or poloxamer 407, a polyoxyl such as a polyoxyl castor oil including polyoxyl 35 castor oil or polyoxyl 40 hydrogenated castor oil, a cyclodextrin, such as hydroxypropyl-gamma-cyclodextrin and tyloxapol.

In other preferred embodiments the one or more nonionic surfactants include from about 0.01% to about 3.5% w/v poloxamer 407, preferably, from about 0.2% to about 3.5% w/v, preferably, about 0.1%, 0.2%, 0.7%, 1%, 3% and 3.5% w/v.

In other preferred embodiments the one or more nonionic surfactants include from about 0.01% to about 3% w/v poloxamer 188, preferably, from about 0.1% w/v to about 1% w/v, preferably about 0.01%, 0.1%, 0.2%, 0.4%, 0.5% and 0.75% w/v.

In other preferred embodiments the one or more nonionic surfactants include from about 0.001% to about 2.0% w/v polyoxyl castor oil, preferably, from about 0.005% to about 0.25% w/v, preferably, from about 0.01% w/v to about 1% w/v, preferably, from about 0.01% to about 0.1% w/v, preferably, from about 0.15% to about 0.25% w/v, preferably about 0.001%, 0.01%, 0.1%, 0.15%, 0.25%, 0.5% and 1% w/v.

In other more preferred embodiments, the one or more nonionic surfactants include from about 0.01% to about 5% w/v hydroxypropyl-gamma-cyclodextrin, preferably from about 0.5% to about 5% w/v, preferably, from about 1.5% to about 3.0% w/v, preferably, about 0.25%, 0.5%, 0.7%, 0.75%, 1%, 1.5%, 2%, 2.5%, 3%, 3.5%, 4% and 5% w/v.

In other preferred embodiments, the addition of 0.005% to 4.0% w/v tyloxapol or from about 1.75% to about 3.00% w/v sorbitol may be added in combination or as a replacement for the one or more nonionic surfactants such that the total surfactant concentration does not exceed 7% w/v;

In other preferred embodiments, the one or more nonionic surfactants may include polyoxyl 35 castor oil at an amount from about 0.25% to about 5.00% w/v; preferably from about 0.15% to about 0.25% w/v.

Figure 3:
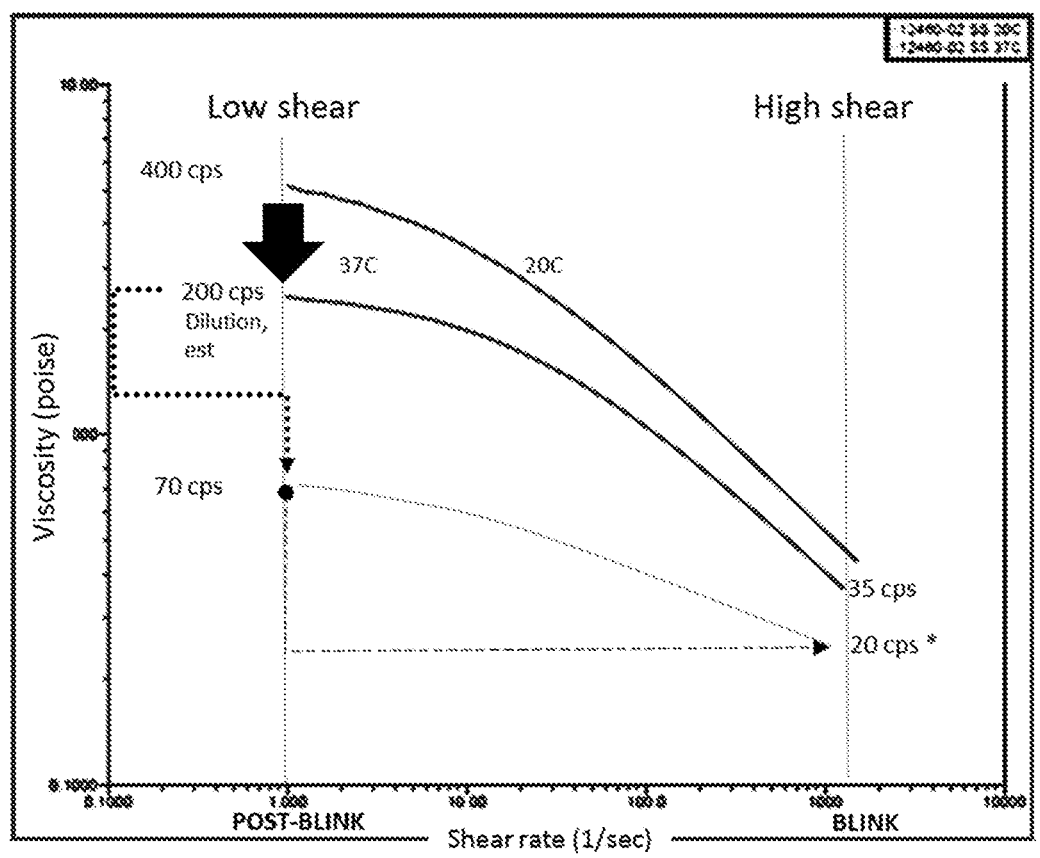
FIG. 3. Shear rate of a composition containing 5.0% w/v poloxamer 407 and 0.75% w/v high molecular weight carboxymethyl cellulose.

Viscosity enhancers that can be used in accordance with the present invention are non-Newtonian viscosity enhancers, which include, but are not limited to cellulose derivatives, carbomers (Carbopol®), gums, and hyaluronic acids (hyaluronates), dextrans, polyvinyl alcohol, polyacrylic acids, povidone, polyethylene glycol, propylene glycol and chitosans; where for cellulose derivatives particularly preferred are one or more of carboxymethyl cellulose ("CMC") high molecular weight blend, CMC low molecular weight blend, CMC moderate molecular weight blend, methylcellulose, methyl cellulose 4000, hydroxymethyl cellulose, hydroxypropyl cellulose ("HPC"), hydroxypropylmethyl cellulose high molecular weight blend ("HPMC"), hydroxyl propyl methyl cellulose 2906, carboxypropylmethyl cellulose high molecular weight blend ("CPMC"), hydroxyethyl cellulose, or hydroxyethyl cellulose and hyaluronic acid, such that the concentrations cumulatively do not create a phase transition to an in situ gel. The non-Newtonian properties afforded to compositions of the invention by viscosity enhancers of this type can be seen in FIG. 3, which demonstrates the during blink and between blink difference in viscosity. This viscosity can be modified to target specific clinical treatments. Specific viscosities and viscosity enhancers may achieve an intrablink (high shear rate) viscosity of about 30 cps or less, more preferably about 25 cps or less, and most preferably about 20 cps or less. Specific clinical treatments may use the following interblink (low shear rate) viscosities:

i. contact lens use: about 1 to about 5 cps;
    ii. artificial tears mild—moderate dry eye: about 5 cps to about 100 cps;
    iii. artificial tears moderate—severe dry eye: about 100 cps to about 250 cps; and
    iv. artificial tears severe dry eye: about 250 to about 5000 cps.

In preferred embodiments, the viscosity enhancing excipient is selected from the group consisting of CMC low molecular weight blend, CMC moderate molecular weight blend, CPMC, HPC, HPMC and carbomer 940 or a combination thereof.

In more preferred embodiments the amount of CMC is from about 0.05% to about 1.75% w/v including 0.05%, 0.10% w/v, 0.20% w/v, 0.25% w/v, 0.3% w/v, 0.4% w/v, 0.5% w/v, 0.55% w/v, 0.62% w/v, 0.65% w/v, 0.75% w/v, 1.0% w/v, 1.25% w/v, 1.35% w/v, 1.38% w/v, 1.40% w/v and 1.45% w/v.

In other more preferred embodiments, the amount of HPC is from about 0.10% to about 1.75% w/v including 1.0% w/v, 1.25% w/v, 1.40% w/v, 1.50% w/v or 1.75% w/v.

In other more preferred embodiments the amount of HPMC is based on the molecular weight of Methocell® (Dow-Corning) from about 0.10% to about 1.75% w/v, preferably from about 0.1% to about 1.5% w/v, from about 0.5% to about 1.25% w/v, from about 0.65% to about 1.0% w/v, from about 1% to about 1.35% w/v, from about 1.25% to about 1.35% w/v, from about 1.35% to about 1.5% w/v, from about 1.35% to about 1.45% w/v, preferably about 0.10% w/v, 0.20% w/v, 0.25% w/v, 0.3% w/v, 0.4% w/v, 0.5% w/v, 0.55% w/v, 0.62% w/v, 0.65% w/v, 0.75% w/v, 0.85% w/v, 1.0% w/v, 1.25% w/v, 1.3% w/v, 1.35% w/v, 1.38% w/v, 1.40% w/v, 1.45% w/v and 1.48% w/v.

In more preferred embodiments the amount of carbomer 940 is from about 0.01% to about 2.0% w/v, preferably from about 0.8% to about 1.3% w/v and more preferably at about 0.01%, 0.8% 0.9%, 1.1%, 1.2% or 1.3% w/v.

In certain embodiments polyvinyl alcohol ("PVA") may be used as a viscosity enhancer in compositions of the present invention. Preferably, PVA is at a concentration of about 0.5% w/v.

In other embodiments, the present invention further comprises glycerin in an amount from about 0.05% to about 2.0% w/v; preferably from about 0.1% to about 0.4% w/v.

Polyols suitable for use in the present invention include, but are not limited to, mannitol, glycerol, erythritol, lactitol, xylitol, sorbitol, isosorbide, and maltitol. In a more preferred embodiment, the polyol is mannitol. In another more preferred embodiment, the polyol is at a concentration from about 0.1% to about 4% w/v, from about 0.25% to about 5.5% w/v, from about 0.25% to about 4.0% w/v, from about 0.25% to about 2.5% w/v, from about 1% to about 4% w/v, from about 1% to about 2.5% w/v, from about 1.5% to about 3.0% w/v, from about 1.5% to about 2.5% w/v, from about 2% to about 2.5% w/v and about 1% and 2.5% w/v.

Electrolytes suitable for use in the present invention include, but are not limited to, magnesium ions, sodium chloride ("NaCl"), potassium chloride ("KCl") and a combination thereof. In a more preferred embodiment, the magnesium ions are derived from magnesium chloride. In another more preferred embodiment, the total electrolyte concentration is at a concentration from about 0.01% to about 2.0% w/v. In a more preferred embodiment the magnesium ions are at a concentration from about 0.01% to about 0.25% w/v as $MgCl_2$, preferably about 0.05% to about 0.15% w/v and from about 0.075% to about 0.125% w/v, and the NaCl is at a concentration from about 0.01% to about 2.0% w/v, preferably, from about 0.1% to about 2.0% w/v from about 0.2% to about 2.0% w/v, from about 0.25% to about 2.0% w/v, and more preferably about 0.01%, 0.2%, 0.25%, 0.3%, 0.35%, 0.37%, 0.4%, 0.5%, 0.62%, 0.7%, 0.75%, 1.0%, 1.25%, 1.5%, 1.75%, and 2.0% w/v, and the KCl is at a concentration from about 0.1% to about 0.5% w/v.

Preservatives suitable for use in the present invention include, but are not limited to, benzalkonium chloride ("BAK"), sorbate, methylparaben, polypropylparaben, chlorobutanol, thimerosal, phenylmercuric acetate, perborate, phenylmercuric nitrate and combinations thereof. In a preferred embodiment, the preservative is BAK, sorbate or a combination thereof. In a preferred embodiment, the preservative is at a concentration from about 0.005% to about 0.15% w/v. In a more preferred embodiment BAK is at a concentration from about 0.005% to about 0.02% w/v and sorbate is at a concentration from about 0.015% to about 0.15% w/v.

Antioxidants suitable for use in the present invention include, but are not limited to, citrate, EDTA, sodium metabisulfite, sodium thiosulfate, acetylcysteine, butylated hydroxyanisole and butylated hydroxytoluene and a combination thereof. In a preferred embodiment, the preservative is at a concentration from about 0.05% to about 0.2% w/v.

In certain embodiments, a terpenoid may be used in compositions of the present invention. In a preferred embodiment, a terpenoid includes, but is not limited to, citral, WS-12, icilin and menthol.

In certain embodiments menthol may be used in compositions of the present invention. Preferably, menthol is at a concentration from about 0.01 to about 4.00 mM, from about 0.01 to about 2.0 mM, from about 0.025 to about 0.07 mM, from about 0.07 to about 0.3 mM, from about 0.07 to about 0.1 mM, from about 0.1 to about 0.40 mM, from about 0.1 to about 0.2 mM, from about 0.15 to about 0.25 mM, from about 0.25 to about 2.0 mM and about 0.01, 0.07, 0.1, 0.14, 0.15, 0.2, 0.27, 0.30, 0.32, 0.34, 0.36, 0.37, 0.38, 0.40, 0.42, 0.44, 0.46, 0.48, 0.5, 0.6, 0.65, 0.7, 0.75, 0.8, 0.85, 1.0, 1.2, 1.5, 1.6, 1.75, 2.0 or 4.0 mM.

Buffers and pH adjustors that can be used in accordance with the present invention include, but are not limited to, acetate buffers, carbonate buffers, citrate buffers, phosphate buffers and borate buffers. In a preferred embodiment, the buffers and pH adjustors are at a concentration from about 1 to about 100 millimolar, more preferably from about 3 to about 10 millimolar and most preferably about 3, 4, 5, 5.5, 6, 6.5, 7, 7.5, 8, 8.5, 9, 9.5 or 10 millimolar It is understood that various acids or bases can be used to adjust the pH of the composition as needed. pH adjusting agents include, but are not limited to, sodium hydroxide and hydrochloric acid. Surprisingly, pH has not been found to alter comfort in the artificial tears compositions. pH of the compositions can be from 4.0 to 8.0, more preferably from about 5.0 to about 8.0 and from about 5.0 to about 6.0, and less than 6.0.

Compositions of the Invention

The present invention discovers a narrow therapeutic range of non-ionic surfactant(s) concentration(s) in a preferred embodiment requiring either a non-Newtonian viscosity excipient(s), electrolytes or other excipients that provide improved epithelial protection and healing such that with regular use or even on a single instillation both comfort and efficacy are improved. The ingredients and concentrations of the compositions represented herein are the best-known embodiments but are not intended to be all inclusive.

Artificial Tears

In certain embodiments, the present invention is directed to artificial tear compositions comprising a means for inducing tears and a means for sequestering tears.

In a preferred embodiment, the means for inducing tears is selected from a pH from about 5 to about 6, a terpenoid and an osmolarity of from about 350 to about 550 milliosmoles.

In another preferred embodiment, the means for sequestering tears comprises from about 1.5% to about 5.9% w/v total volume of one or more nonionic surfactants and one or more viscosity enhancers, wherein the one or more viscosity enhancers provides a viscosity of from about 50 to about 10,000 centipoise at 0 shear to 1 second.

In more preferred embodiment, the one or more nonionic surfactants are selected from the group consisting of polysorbates, poloxamers, polyoxyl castor oils and combinations thereof.

In another more preferred embodiment, the one or more viscosity enhancers are selected from the group consisting of cellulose derivatives, carbomers, gums, and hyaluronic acids, dextrans, polyvinyl alcohol, polyacrylic acids, povidone, polyethylene glycols, propylene glycol, chitosans and combinations thereof, even more preferably the one or more viscosity enhancers are selected from the group consisting of cellulose derivatives, carbomers, polyvinyl alcohol, polyethylene glycols and combinations thereof.

In another embodiment, the artificial tear compositions of the present invention further comprise a polyol, preferably selected from the group consisting of mannitol, xylitol, sorbitol, isosorbide, erythritol, glycerol, maltitol and a combination thereof.

In another embodiment, the artificial tear compositions of the present invention further comprise one or more electrolytes, preferably selected from the group consisting of magnesium ions, sodium chloride, potassium chloride and a combination thereof.

The present invention is further directed to an artificial tear composition comprising:
  one or more nonionic surfactants selected from the group consisting of poloxamers, polysorbates, cyclodextrins, alkylaryl polyethers, polyoxyethyleneglycol alkyl ethers, tyloxapol, and polyoxyls at a total concentration from about 1.5% to about 6.0% w/v; preferably the one or more nonionic surfactants are selected from the group consisting of from about 0.01% to about 4.0% w/v of a polysorbate, from about 0.01% to about 3.5% w/v of a poloxamer, from about 0.01% to about 2.0% w/v of a polyoxyl and from about 0.01% to about 5.0% w/v hydroxypropyl-gamma-cyclodextrin;

one or more viscosity enhancers selected from the group consisting of cellulose derivatives, carbomers, gums, dextrans, polyvinyl alcohol, polyacrylic acids, povidone, polyethylene glycol, propylene glycol, chitosans, and hyaluronates and hyaluronic acids; from about 0.01% to about 2.0% w/v of one or more electrolytes selected from the group consisting of sodium chloride, potassium chloride and magnesium ions, preferably, the one or more electrolytes is selected from about 0.01% to about 0.25% w/v magnesium ions, from about 0.10% to about 2.0% w/v sodium chloride and from about 0.1% to about 0.5% w/v potassium chloride;

optionally, from about 0.1% to about 4% w/v of a polyol, preferably the polyol is selected from 0.25% to about 4.0% w/v of mannitol or glycerol;

optionally, from about 0.01% to about 2.0% w/v of a polyethylene glycol selected from the group consisting of polyethylene glycol 400, polyethylene glycol 6000, polyethylene glycol 10000, polyethylene glycol 20000 and a combination thereof;

optionally, from about 0.01 to about 4.0 mM menthol and/or from about 0.1% to about 0.12% w/v sorbate;

optionally, from about 3 to about 10 millimolar of a citrate buffer or a phosphate buffer wherein the concentration of the viscosity enhancers provides a composition with a viscosity from about 0.1 to about 1,000 centipoise (cps), preferably wherein a low shear viscosity is from 1 to 1000 cps and a final high shear viscosity is 30 cps or less.

The present invention is further directed to an artificial tear composition comprising:

one or more nonionic surfactants selected from the group consisting of polysorbate 80, poloxamer 407, poloxamer 188, polyoxyl castor oil and hydroxypropyl-gamma-cyclodextrin at a total concentration from about 0.1% to about 1.0% w/v or from 1.0% to about 5.9% w/v, wherein the upper range provides greater tear moisture retention and therapeutic efficacy for more severe dry eye;

from about 0.1% to about 2.0% w/v hydroxypropylmethyl cellulose or a concentration of a cellulose derivative that yields a total viscosity of the composition equal to the total viscosity of the composition provided by from about 0.1% to about 1.5% w/v hydroxypropylmethyl cellulose, preferably from about 0.1% to about 1.35% w/v, including from about 0.9% to about 1.45% w/v of carboxymethyl cellulose or carbomer 940; from about 0.1% to about 2.0%% w/v sodium chloride, preferably from about 0.25% to about 1.0% w/v;

from about 0.05% to about 0.1% w/v magnesium chloride;

optionally, from about 0.25% to about 4.0% w/v mannitol, preferably from about 0.75% to about 2.5% w/v;

optionally, from about 0.1% to about 0.75% w/v polyethylene glycol 400 or polyethylene glycol 20000;

optionally, from about 4 to about 8 millimolar citrate buffer or phosphate buffer;

optionally, menthol, preferably from about 0.1 to about 1.75 millimolar, more preferably from about 1.0 to about 1.75 millimolar; and optionally, sorbate, preferably at 0.1% or 0.12% w/v, wherein optionally, the composition has a pH from about 5.0 to about 7.0.

In a preferred embodiment, the present invention is directed to artificial tear compositions comprising:

from about 2.0% to about 4.0% w/v of one or more nonionic surfactants selected from the group consisting of polysorbates, poloxamers, polyoxyl castor oils and combinations thereof;

from about 0.5% to about 2.0% w/v of a viscosity enhancer selected from the group consisting of carboxymethyl cellulose and carbomer 940;

from about 1.0% to about 5.0% w/v mannitol;

from about 0.5% to about 1.0% w/v of a polyethylene glycol selected from polyethylene glycol 400, polyethylene glycol 6000, polyethylene glycol 10000, polyethylene glycol 20000 and a combination thereof;

from about 0.1% to about 2.0% w/v sodium chloride;

from about 0.1% to about 0.12% w/v sorbate;

from about 3.0 to about 10.0 millimolar citrate buffer, wherein w/v denotes weight by total volume of the composition and wherein the composition has a pH from about 5.0 to about 7.4, preferably from about 5.0 to about 6.0.

In another embodiment artificial tear compositions of the present invention, further comprising from about 0.25 to about 4.00 millimolar menthol.

In another embodiment artificial tear compositions of the present invention, further comprising about 0.1% w/v magnesium chloride.

In another embodiment artificial tear compositions of the present invention, further comprising an excipient selected from the group consisting of about 0.1% w/v ethylenediaminetetraacetic acid, from about 0.1% to about 0.5% w/v polyvinyl alcohol and a combination thereof.

The present invention is further directed to an artificial tear composition comprising:

from about 0% to about 3.5% w/v polysorbate 80;

from about 0% to about 2.75% w/v poloxamer 407;

from about 0% to about 2.75% w/v poloxamer 188;

from about 0% to about 2.0% w/v polyoxyl castor oil;

from about 0.1% to about 2.0% w/v hydroxypropylmethyl cellulose;

from about 0% to about 2.0% w/v polyethylene glycol 400;

from about 0% to about 3.0% w/v mannitol;

from about 0% to about 0.90% w/v sodium chloride;

from about 0.04 to about 0.50 millimolar menthol;

about 4 millimolar citrate buffer; and optionally, about 0.1% w/v sorbate, wherein the composition has a pH of about 7.0 and wherein the total nonionic surfactant concentration is from about 1.5% to about 5.0% w/v.

In a more preferred embodiment, the present invention is directed to artificial tear compositions comprising:

a surfactant selected from the group consisting of about 3.50% w/v poloxamer 407 or about 0.25% w/v poloxamer 407 and 1.75% w/v sorbitol;

about 0.25% w/v polyoxyl 40 castor oil;

about 0.75% w/v of a polyethylene glycol having a molecular weight from about 400 to about 20,000 Daltons;

about 1.00% w/v mannitol;

from about 0.45% to about 0.75% sodium chloride;

from about 0.90% to about 1.20% w/v carbomer 940;
from about 0.4 to about 2.75 millimolar menthol;
about 4.00 millimolar citrate buffer;
about 0.10% w/v ethylenediaminetetraacetic acid;
about 0.10% w/v polyvinyl alcohol; and
about 0.12% w/v sorbate.

The present invention is further directed to an artificial tear composition comprising:
from about 0% to about 3.5% w/v polysorbate 80;
from about 0% to about 2.75% w/v poloxamer 407;
from about 0% to about 2.75% w/v poloxamer 188;
from about 0% to about 2.0% w/v polyoxyl castor oil;
from about 0.1% to about 2.0% w/v hydroxypropylmethyl cellulose;
from about 0% to about 2.0% w/v polyethylene glycol 400;
from about 0% to about 3.0% w/v mannitol;
from about 0% to about 0.90% w/v sodium chloride;
from about 0.04 to about 0.50 millimolar menthol;
about 4 millimolar citrate buffer; and
optionally, about 0.1% w/v sorbate,
wherein the composition has a pH of about 7.0 and wherein the total nonionic surfactant concentration is from about 1.5% to about 5.0% w/v.

The present invention is further directed to an artificial tear composition comprising:
two or more nonionic surfactants selected from the group consisting of polysorbate 80, poloxamer 407, poloxamer 188, polyoxyl castor oil and hydroxypropyl-gamma-cyclodextrin at a total concentration from about 1.5% to about 5.9% w/v;
about 1% w/v mannitol;
about 0.1% w/v hydroxypropylmethyl cellulose or a concentration of carboxymethyl cellulose that yields a total viscosity of the composition equal to the total viscosity of the composition provided by about 0.1% w/v hydroxypropylmethyl cellulose;
from about 0.1% to about 0.75% w/v sodium chloride, preferably from about 0.3% to about 0.4% w/v;
about 0.1% w/v magnesium chloride;
optionally, about 3 millimolar phosphate buffer or for pH less than 6.0 citrate buffer;
optionally, from about 0.1 to about 0.50 millimolar menthol; and
optionally, about 0.1% w/v sorbate,
wherein optionally, the composition has a pH from about 5.0 to about 7.0.

The present invention is further directed to an artificial tear composition comprising:
two or more nonionic surfactants selected from the group consisting of polysorbate 80, poloxamer 407, poloxamer 188, polyoxyl castor oil and hydroxypropyl-gamma-cyclodextrin at a total concentration from about 1.5% to about 5.9% w/v;
from about 1.0% to 2.5% w/v mannitol;
from about 0.10% to about 1.5% w/v hydroxypropylmethyl cellulose or a concentration of carboxymethyl cellulose that yields a total viscosity of the composition equal to the total viscosity of the composition provided by from about 0.1% to about 1.5% w/v hydroxypropylmethyl cellulose;
from about 0.1% to about 0.5% w/v sodium chloride, preferably from about 0.2% to about 0.4% w/v;
about 0.1% w/v magnesium chloride;
optionally, about 3 millimolar phosphate or citrate buffer;
optionally, from about 0.1 to about 0.50 millimolar menthol;
optionally, about 0.1% w/v sorbate,
wherein optionally, the composition has a pH from about 5.0 to about 7.0.

The present invention is further directed to an artificial tear composition comprising:
two or more nonionic surfactants selected from the group consisting of polysorbate 80, poloxamer 407, poloxamer 188, polyoxyl castor oil and hydroxypropyl-gamma-cyclodextrin at a total concentration from about 1.5% to about 5.9% w/v;
about 2.5% w/v mannitol;
from about 0.65% to about 1.0% w/v hydroxypropylmethyl cellulose or a concentration of carboxymethyl cellulose that yields a total viscosity of the composition equal to the total viscosity of the composition provided by from about 0.65% to about 1.0% w/v hydroxypropylmethyl cellulose;
from about 0.1% to about 0.75% w/v sodium chloride, preferably from about 0.3% to about 0.4% w/v;
about 0.1% w/v magnesium chloride;
optionally, about 3 millimolar phosphate buffer or about 4 millimolar citrate buffer;
optionally, from about 0.1 to about 0.50 millimolar menthol;
optionally, about 0.1% w/v sorbate,
wherein optionally, the composition has a pH from about 5.5 to about 7.0.

The present invention is further directed to an artificial tear composition comprising:
two or more nonionic surfactants selected from the group consisting of polysorbate 80, poloxamer 407, poloxamer 188, polyoxyl castor oil and hydroxypropyl-gamma-cyclodextrin at a total concentration from about 1.5% to about 5.9% w/v;
about 2.5% w/v mannitol;
from about 1.0% to about 1.35% w/v hydroxypropylmethyl cellulose or a concentration of carboxymethyl cellulose that yields a total viscosity of the composition equal to the total viscosity of the composition provided by from about 1.0% to about 1.35% w/v hydroxypropylmethyl cellulose;
from about 0.1% to about 0.75% w/v sodium chloride, preferably from about 0.3% to about 0.4% w/v;
about 0.1% w/v magnesium chloride;
optionally, about 3 millimolar phosphate buffer or about 4 millimolar citrate buffer;
optionally, from about 0.1 to about 0.50 millimolar menthol;
optionally, about 0.1% w/v sorbate,
wherein optionally, the composition has a pH from about 5.5 to about 7.0.

The present invention is further directed to an artificial tear composition comprising:
two or more nonionic surfactants selected from the group consisting of polysorbate 80, poloxamer 407, poloxamer 188, polyoxyl castor oil and hydroxypropyl-gamma-cyclodextrin at a total concentration from about 1.0% to about 5.9% w/v;
about 2.5% w/v mannitol;
from about 1.35% to about 1.45% w/v hydroxypropylmethyl cellulose or a concentration of carboxymethyl cellulose that yields a total viscosity of the composition equal to the total viscosity of the composition provided by from about 1.35% to about 1.45% w/v hydroxypropylmethyl cellulose;
from about 0.1% to about 0.75% w/v sodium chloride, preferably from about 0.3% to about 0.4% w/v;

about 0.1% w/v magnesium chloride;
optionally, about 3 millimolar phosphate buffer or about 4 millimolar citrate buffer;
optionally, from about 0.1 to about 0.50 millimolar menthol;
optionally, about 0.1% w/v sorbate,
wherein optionally, the composition has a pH from about 5.5 to about 7.0.

The present invention is further directed to an artificial tear composition comprising:
two or more nonionic surfactants selected from the group consisting of polysorbate 80, poloxamer 407, poloxamer 188, polyoxyl castor oil and hydroxypropyl-gamma-cyclodextrin at a total concentration from about 1.5% to about 5.9% w/v, wherein one of the two or more nonionic surfactants is from about 0.25% to about 1.0% w/v polyoxyl castor oil;
about 2.5% w/v mannitol;
from about 1.25% to about 1.35% w/v hydroxypropylmethyl cellulose or a concentration of carboxymethyl cellulose that yields a total viscosity of the composition equal to the total viscosity of the composition provided by from about 1.25% to about 1.35% w/v hydroxypropylmethyl cellulose;
from about 0.1% to about 0.75% w/v sodium chloride, preferably from about 0.3% to about 0.4% w/v;
about 0.1% w/v magnesium chloride;
optionally, about 3 millimolar phosphate or citrate buffer;
optionally, from about 0.1 to about 0.50 millimolar menthol;
optionally, about 0.1% w/v sorbate,
wherein optionally, the composition has a pH from about 5.0 to about 7.0.

The present invention is further directed to an artificial tear composition comprising:
about 2.0% w/v polysorbate 80;
about 0.2% w/v poloxamer 407;
about 0.5% w/v poloxamer 188;
about 1.0% w/v hydroxypropyl-gamma-cyclodextrin;
from about 0.5% to about 1.25% w/v hydroxypropylmethyl cellulose or a concentration of a cellulose derivative that yields a total viscosity of the composition equal to the total viscosity of the composition provided by from about 0.5% to about 1.25% w/v hydroxypropylmethyl cellulose;
from about 0.20% to about 0.75% w/v sodium chloride;
about 0.1% w/v magnesium chloride; and
about 0.025 to about 0.07 millimolar menthol.

The present invention is further directed to an artificial tear composition for severe dry eye comprising:
about 2.0% w/v polysorbate 80;
about 0.2% w/v poloxamer 407;
about 0.5% w/v poloxamer 188;
about 1.0% w/v hydroxypropyl-gamma-cyclodextrin;
from about 1.25% to about 1.35% w/v hydroxypropylmethyl cellulose or a concentration of a cellulose derivative that yields a total viscosity of the composition equal to the total viscosity of the composition provided by from about 1.25% to about 1.35% w/v hydroxypropylmethyl cellulose;
from about 0.25% to about 0.75% w/v sodium chloride;
about 0.1% w/v magnesium chloride; and
about 0.07 to about 0.1 millimolar menthol.

The present invention is further directed to an artificial tear composition for severe dry eye comprising:
about 2.0% w/v polysorbate 80;
about 0.2% w/v poloxamer 407;
about 0.5% w/v poloxamer 188;
about 1.0% w/v hydroxypropyl-gamma-cyclodextrin;
from about 1.35% to about 1.5% w/v hydroxypropylmethyl cellulose or a concentration of a cellulose derivative that yields a total viscosity of the composition equal to the total viscosity of the composition provided by from about 1.35% to about 1.5% w/v hydroxypropylmethyl cellulose;
from about 0.25% to about 0.75% w/v sodium chloride;
about 0.1% w/v magnesium chloride; and
about 0.1 to about 0.20 millimolar menthol.

The present invention is further directed to an artificial tear composition comprising:
about 3.5% w/v polysorbate 80;
about 0.7% w/v poloxamer 407;
about 1.0% w/v poloxamer 188;
about 0.01% w/v polyoxyl castor oil;
about 0.85% w/v hydroxypropylmethyl cellulose;
about 2.5% w/v mannitol;
about 0.1% w/v magnesium chloride;
about 0.25% w/v sodium chloride;
from about 0.07 to about 0.50 millimolar menthol, preferably 0.07, 0.10, 0.14 0.20 or 0.40 millimolar menthol;
optionally, about 0.1% w/v sorbate; and
about 3 millimolar phosphate buffer or about 4 millimolar citrate buffer,
wherein the composition has a pH of about 7.0.

The present invention is further directed to an artificial tear composition comprising:
about 3.5% w/v polysorbate 80;
about 0.2% w/v poloxamer 407;
about 0.2% w/v poloxamer 188;
about 0.01% w/v polyoxyl castor oil;
about 0.70% to about 0.80% w/v hydroxypropylmethyl cellulose, preferably 0.70%, 0.75% or 0.80% w/v;
about 2.5% w/v mannitol;
about 0.1% w/v magnesium chloride;
about 0.25% to about 0.35% w/v sodium chloride, preferably 0.25%, 0.30% or 0.35% w/v;
from about 0.07 to about 0.14 millimolar menthol, preferably 0.07, 0.10, or millimolar menthol;
optionally, about 0.1% w/v sorbate; and
about 3 millimolar phosphate buffer or about 4 millimolar citrate buffer,
wherein the composition has a pH of about 7.0.

The present invention is further directed to an artificial tear composition comprising:
about 2.0% w/v polysorbate 80;
about 0.2% w/v poloxamer 407;
about 0.5% w/v poloxamer 188;
about 1.0% w/v hydroxypropyl-gamma-cyclodextrin;
from about 0.5% to about 1.25% w/v hydroxypropylmethyl cellulose or a concentration of a cellulose derivative that yields a total viscosity of the composition equal to the total viscosity of the composition provided by from about 0.5% to about 1.25% w/v hydroxypropylmethyl cellulose;
from about 0.2% to about 0.75% w/v sodium chloride;
about 0.1% w/v magnesium chloride; and
about 0.025 to about 0.07 millimolar menthol.

The present invention is further directed to an artificial tear composition comprising:
about 2.0% w/v polysorbate 80;
about 0.2% w/v poloxamer 407;
about 0.5% w/v poloxamer 188;
about 1.0% w/v hydroxypropyl-gamma-cyclodextrin;

from about 1.25% to about 1.35% w/v hydroxypropylmethyl cellulose or a concentration of a cellulose derivative that yields a total viscosity of the composition equal to the total viscosity of the composition provided by from about 1.25% to about 1.35% w/v hydroxypropylmethyl cellulose;
from about 0.25% to about 0.75% w/v sodium chloride;
about 0.1% w/v magnesium chloride; and
about 0.07 to about 0.1 millimolar menthol.

The present invention is further directed to an artificial tear composition comprising:
about 3.0% w/v polysorbate;
about 0.10% w/v poloxamer 188;
about 0.01% w/v polyoxyl castor oil;
from about 0.0% to about 2.0% w/v hydroxypropylmethyl cellulose;
from about 0.5% to about 2.5% w/v mannitol;
about 0.10% w/v magnesium ions;
from about 0.0% to about 0.75% w/v NaCl; and
a buffer at a concentration from about 1 mM to about 100 mM,
wherein the composition has a pH from about 5.5 to about 8.0 and wherein the viscosity is less than or equal to 500 centipoise.

The present invention is further directed to an artificial tear composition comprising:
about 4.0% w/v Captisol®;
about 1.35% w/v HPMC;
about 0.02% w/v BAK;
about 0.10% w/v sorbate;
about 0.10% w/v EDTA;
about 3 mM Citrate buffer; and
from about 0.3% to about 0.5% w/v NaCl,
wherein the composition has a pH from about 6.0.

TABLE 1

Artificial Tear Compositions

| (% w/v) | A | B | C | D | E | F | G | H |
| --- | --- | --- | --- | --- | --- | --- | --- | --- |
| Polysorbate 80 | 3.00% | 3.00% | 3.00% | 3.00% | 2.50% | 1.50% | 1.50% | 3.00% |
| Poloxamer 407 | — | — | — | — | 0.20% | 0.20% | 0.20% | — |
| Poloxamer 188 | 0.10% | 0.10% | 0.10% | 0.10% | 0.10% | 0.10% | 0.10% | — |
| Polyoxyl castor oil | 0.01% | 0.01% | 0.01% | 0.01% | — | — | — | 0.01% |
| Hydroxypropyl-gamma-cyclodextrin | — | — | — | — | 1.00% | 2.00% | 1.00% | — |
| Mannitol | 2.50% | 2.50% | 2.50% | 2.50% | 2.50% | 2.50% | 2.50% | 2.50% |
| HPMC | 0.10% | 0.65% | 1.00% | 1.35% | 1.30% | 1.40% | 1.45% | 1.25% |
| NaCl | 0.20% | 0.75% | 0.75% | 0.75% | 0.30% | 0.40% | 0.35% | 0.30% |
| $MgCl_2$ | 0.10% | 0.10% | 0.10% | 0.10% | 0.10% | 0.10% | 0.10% | 0.10% |
| Menthol (mM) | — | — | — | — | 0.07 | 0.1 | 0.1 | — |
| Phosphate buffer or Citrate buffer (mM) | 3 | 3 | 3 | 3 | 3 | 3 | 3 | 3 |
| pH | 7.0 | 7.0 | 7.0 | 7.0 | 5.5 | 5.5 | 5.5 | — |

| (% w/v) | I | J | K | L | M | N | O | P |
| --- | --- | --- | --- | --- | --- | --- | --- | --- |
| Polysorbate 80 | 1.50% | 1.50% | 1.50% | 3.00% | 1.50% | 1.50% | 3.50% | 1.50% |
| Poloxamer 407 | 0.20% | 0.20% | 0.20% | 0.20% | 0.20% | 0.20% | 0.70% | 0.20% |
| Poloxamer 188 | 1.00% | 1.00% | 0.50% | 0.10% | 0.75% | 0.75% | 1.00% | 0.50% |
| Polyoxyl castor oil | 0.01% | 0.01% | 1.00% | 0.01% | 0.01% | 0.01% | 0.01% | 1.00% |
| Hydroxypropyl-gamma-cyclodextrin | 0.50% | 0.50% | 0.50% | 0.50% | 1.50% | 1.50% | — | 0.50% |
| Mannitol | 2.50% | 2.50% | 2.50% | 1.00% | 2.50% | 2.50% | 2.50% | 2.50% |
| HPMC | 1.25% | 1.35% | 1.35% | 0.10% | 1.35% | 1.45% | 0.85% | 1.25% |
| NaCl | 0.30% | 0.30% | 0.30% | 0.30% | 0.40% | 0.25% | 0.25% | 0.30% |
| $MgCl_2$ | 0.10% | 0.10% | 0.10% | 0.10% | 0.10% | 0.10% | 0.10% | 0.10% |
| Menthol (mM) | — | — | — | — | 0.15 | 0.15-0.25 | 0.07-0.20 | — |
| Phosphate buffer or Citrate buffer (mM) | 3 | 3 | 3 | 3 | 3 | 3 | 3 | 3 |
| pH | — | — | — | 7.0 | 5.5 | 5.5 | 7 | — |

| (% w/v) | Q | R | S | T | U | V | W |
| --- | --- | --- | --- | --- | --- | --- | --- |
| Polysorbate 80 | 1.00% | 3.00% | 1.00% | 1.50% | 1.50% | 2.00% | 3.00% |
| Poloxamer 407 | 0.20% | — | 0.20% | 0.20% | 0.20% | 0.20% | 0.20% |
| Poloxamer 188 | 0.10% | — | 0.10% | 0.10% | 0.10% | 0.50% | 0.20% |
| Polyoxyl castor oil | — | — | — | — | — | — | 0.01% |
| Hydroxypropyl-gamma-cyclodextrin | — | — | 0.50% | 1.00% | 1.00% | 1.00% | — |
| Mannitol | 1.00% | 1.00% | 1.00% | 2.50% | 2.50% | — | 1.00% |
| HPMC | 0.10% | 0.10% | 0.10% | 1.30% | 1.40% | — | 0.10% |
| NaCl | 0.40% | 0.40% | 0.40% | 0.30% | 0.30% | 0.75% | 0.30% |
| $MgCl_2$ | 0.10% | 0.10% | 0.10% | 0.10% | 0.10% | 0.10% | 0.10% |
| Menthol (mM) | — | — | — | 0.07 | 0.1 | 0.1-0.2 | — |
| Phosphate buffer or Citrate buffer (mM) | 3 | 3 | 3 | 3 | 3 | 3 | 3 |
| pH | — | — | — | 5.5 | 5.5 | — | 7.0 |

TABLE 2

More Artificial Tear Compositions

| (% w/v) | 1 | 2 | 3 | 4 | 5 | 6 | 7 | 8 | 9 |
|---|---|---|---|---|---|---|---|---|---|
| Polyoxyl 40 stearate | 4.50% | 5.00% | 5.50% | 5.00% | 5.00% | 5.00% | 5.00% | 5.00% | 5.00% |
| Poloxamer 407 | 0.20% | 0.20% | 0.20% | 0.20% | 0.20% | 0.20% | | | 0.20% |
| Poloxamer 188 | | | | 0.10% | 0.10% | 0.10% | | | 0.10% |
| Polysorbate 80 | | | | | | | | | |
| Polysorbate 20 | | | | | | | | | |
| Polyoxyl 35 castor oil | | | | | | | | | |
| CMC | 0.55% | 0.55% | 0.55% | 0.55% | | | 0.55% | | 0.25% |
| HPC | | | | | | | | | |
| HPMC | | | | | 0.40% | 0.62% | | 0.55% | 0.25% |
| Glycerin | | | | | | | | | |
| NaCl 0.25% | ✓ | ✓ | ✓ | ✓ | ✓ | ✓ | ✓ | ✓ | ✓ |
| BAK 0.01% | ✓ | ✓ | ✓ | ✓ | ✓ | ✓ | ✓ | ✓ | ✓ |
| Visual Blur (sec) | 30-60 | 30-60 | 30-60 | 30-60 | 10 | 20-30 | 30-60 | | 10 |

| (% w/v) | 10 | 11 | 12 | 13 | 14 | 15 | 16 | 17 | 18 |
|---|---|---|---|---|---|---|---|---|---|
| Polyoxyl 40 stearate | 5.00% | 5.00% | 5.00% | 5.00% | 5.00% | 5.00% | 3.70% | 3.70% | 4.75% |
| Poloxamer 407 | 0.20% | 0.20% | 0.20% | 0.20% | 0.20% | 0.20% | 0.20% | 0.20% | 0.20% |
| Poloxamer 188 | 0.10% | 0.10% | 0.10% | 0.10% | 0.10% | 0.10% | 0.10% | 0.10% | 0.10% |
| Polysorbate 80 | 1.00% | 1.00% | 1.00% | | | | 1.00% | 1.00% | 1.00% |
| Polysorbate 20 | | | | | | | | | 0.05% |
| Polyoxyl 35 castor oil | | | | | | | | | |
| CMC | 0.25% | 0.55% | | | 0.75% | 0.62% | | | |
| HPC | | | | | | | 1.25% | 1.75% | 1.40% |
| HPMC | 0.25% | | 0.55% | 0.75% | | | | | |
| Glycerin | | | | | | | | | |
| NaCl 0.25% | ✓ | ✓ | ✓ | ✓ | ✓ | ✓ | ✓ | ✓ | ✓ |
| BAK 0.01% | ✓ | ✓ | ✓ | ✓ | ✓ | ✓ | ✓ | ✓ | ✓ |
| Visual Blur (sec) | 10 | | | 30-40 | 90-180 | 60-90 | 5 | 30 | 10-20 |

| (% w/v) | 19 | 20 | 21 | 22 | 23 | 24 | 25 | 26 | 27 |
|---|---|---|---|---|---|---|---|---|---|
| Polyoxyl 40 stearate | 5.00% | 5.00% | | | 5.00% | 5.00% | 5.00% | 5.00% | 5.00% |
| Poloxamer 407 | 0.20% | 0.20% | 0.20% | | 0.20% | 0.20% | 0.20% | 0.20% | 0.20% |
| Poloxamer 188 | 0.10% | 0.10% | 0.10% | | 0.10% | 0.10% | 0.10% | 0.10% | 0.10% |
| Polysorbate 80 | | | | 5.00% | | | | | |
| Polysorbate 20 | | | | | | | | | |
| Polyoxyl 35 castor oil | | | | | | | | | |
| CMC | 0.50% | | | | 0.75% | | | | |
| HPC | | | | 1.50% | | | | | |
| HPMC | | | 0.30% | | 0.30% | 0.50% | 0.10% | 0.20% | 0.30% |
| Glycerin | | | | | | | | | |
| NaCl 0.25% | ✓ | ✓ | ✓ | ✓ | ✓ | ✓ | ✓ | ✓ | ✓ |
| BAK 0.01% | ✓ | ✓ | ✓ | ✓ | ✓ | ✓ | ✓ | ✓ | ✓ |
| Visual Blur | 45 | 2 | 5 | 20 | 30 | 15 | 3.5 | 5 | 5 |
| Wetting Effect (min) | 90 | 30 | 30 | 60 | 90 | 45 | 45 | 45 | 45 |
| Comfort (4 is best) | 3.5 | 3.5 | 3.0 | 3.5 | 3.5 | 3.5 | 3.5 | 3.5 | 3.5 |
| Visual Quality (4 is best) | 3.7 | 3.7 | 3.5 | 3.5 | 3.5 | 3.8 | 3.7 | 3.8 | 3.8 |
| Overall Performance | 2.0 | 3.0 | 3.0 | 3.0 | 3.1 | 3.1 | 3.2 | 3.2 | 3.2 |

| (% w/v) | 28 | 29 | 30 | 31 | 32 | 33 | 34 | 35 |
|---|---|---|---|---|---|---|---|---|
| Polyoxyl 40 stearate | | | 5.00% | | | 5.00% | 5.00% | 5.00% |
| Poloxamer 407 | 0.20% | 5.00% | 0.20% | 0.20% | 5.00% | 0.20% | 0.20% | 0.20% |
| Poloxamer 188 | 0.10% | | 0.10% | 0.10% | | 0.10% | 0.10% | 0.10% |
| Polysorbate 80 | | | | 1.00% | | | | |
| Polysorbate 20 | | | | | | | | |
| Polyoxyl 35 castor oil | | | | | | 0.25% | 1.00% | 1.50% |
| CMC | 0.50% | | | 0.50% | | | | |
| HPC | | 1.75% | | | 1.00% | | | |
| HPMC | | | 0.30% | | | 0.30% | 0.30% | 0.30% |
| Glycerin | | | 0.30% | | | | | |

TABLE 2-continued

More Artificial Tear Compositions

| | | | | | | | | |
|---|---|---|---|---|---|---|---|---|
| NaCl 0.25% | ✓ | ✓ | ✓ | ✓ | ✓ | ✓ | ✓ | ✓ |
| BAK 0.01% | ✓ | ✓ | ✓ | ✓ | ✓ | ✓ | ✓ | ✓ |
| Visual Blur | 45 | 40 | 7 | 15 | 20 | 0 | 1 | 1 |
| Wetting Effect (min) | 30 | 60 | 45 | 60 | 60 | 90 | 180 | 180 |
| Comfort (4 is best) | 3.0 | 3.5 | 3.7 | 3.5 | 3.5 | 4.0 | 4.0 | 4.0 |
| Visual Quality (4 is best) | 3.5 | 3.5 | 3.5 | 3.5 | 3.5 | 3.9 | 4.0 | 4.0 |
| Overall Performance | 3.2 | 3.2 | 3.5 | 3.5 | 3.5 | 3.8 | 4.0 | 4.0 |

| (% w/v) | 36 | 37 | 38 | 39 | 40 | 41 | 42 | 43 | 44 | 45 | 46 |
|---|---|---|---|---|---|---|---|---|---|---|---|
| Polysorbate 80 | 3.00% | 3.00% | 3.00% | 3.00% | 3.00% | 3.00% | 3.00% | 3.00% | 3.00% | 3.00% | 3.00% |
| Poloxamer 188 | 0.10% | 0.10% | 0.10% | 0.10% | 0.10% | 0.10% | 0.10% | 0.10% | 0.10% | 0.10% | 0.10% |
| Polyoxyl Castor oil | 0.01% | 0.01% | 0.01% | 0.01% | 0.01% | 0.01% | 0.01% | 0.01% | 0.01% | 0.01% | 0.01% |
| Mannitol | 1.00% | 1.00% | 1.00% | 1.00% | 2.50% | 2.50% | 2.50% | 2.50% | 2.50% | 2.50% | 2.50% |
| HPMC | 0.10% | 0.10% | 0.10% | 0.10% | 0.50% | 0.50% | 0.50% | 0.50% | 0.50% | 0.65% | 0.75% |
| NaCl | 0.20% | 0.25% | 0.50% | 0.75% | 0.00% | 0.20% | 0.50% | 0.50% | 0.75% | 0.20% | 0.00% |
| MgCl$_2$ | 0.10% | 0.10% | 0.10% | 0.10% | 0.10% | 0.10% | 0.10% | 0.10% | 0.10% | 0.10% | 0.10% |
| Glycerin | 0.00% | 0.00% | 0.00% | 0.00% | 0.00% | 0.00% | 0.00% | 1.00% | 0.00% | 0.00% | 0.00% |
| Phosphate buffer mM | 3.00 | 3.00 | 3.00 | 3.00 | 3.00 | 2.00 | 2.00 | 2.00 | 2.00 | 3.00 | 3.00 |
| pH | 7.00 | 7.00 | 7.00 | 7.00 | 7.00 | 7.00 | 7.00 | 7.00 | 7.00 | 7.00 | 7.00 |
| Osmolarity (mOsm) | | 284 | 369 | | | | 32 | | 39 | | 10 (d) |
| Shear Rate | | 10-1000 | 10-1000 | | | | 10-1000 | | 10-1000 | | 10-1000 |
| Viscosity (cps) | | 72 | 100 | | | | 100 | | 110 | | 147 |

| (% w/v) | 47 | 48 | 49 | 50 | 51 | 52 | 53 | 54 | 55 | 56 | 57 |
|---|---|---|---|---|---|---|---|---|---|---|---|
| Polysorbate 80 | 3.00% | 3.00% | 3.00% | 3.00% | 3.00% | 3.00% | 5.00% | 7.00% | 3.00% | 3.00% | 3.00% |
| Poloxamer 188 | 0.01% | 0.10% | 0.10% | 0.10% | 0.10% | 0.10% | 0.10% | 0.10% | 0.10% | 0.10% | 0.10% |
| Polyoxyl Castor oil | 0.01% | 0.00% | 0.0001% | 0.001% | 0.01% | 0.01% | 0.01% | 0.01% | 0.01% | 0.01% | 0.01% |
| Mannitol | 2.50% | 2.50% | 2.50% | 2.50% | 2.50% | 2.50% | 2.50% | 2.50% | 2.50% | 2.50% | 2.50% |
| HPMC | 0.75% | 1.00% | 1.00% | 1.00% | 1.00% | 1.00% | 1.00% | 1.00% | 1.35% | 1.48% | 1.48% |
| NaCl | 0.20% | 0.00% | 0.00% | 0.00% | 0.00% | 0.20% | 0.20% | 0.20% | 0.50% | 0.50% | 0.70% |
| MgCl$_2$ | 0.10% | 0.10% | 0.10% | 0.10% | 0.10% | 0.10% | 0.10% | 0.10% | 0.10% | 0.10% | 0.10% |
| Glycerin | 0.00% | 0.00% | 0.00% | 0.00% | 0.00% | 0.00% | 0.00% | 0.00% | 0.00% | 0.00% | 0.00% |
| Phosphate buffer mM | 3.00 | 3.00 | 3.00 | 3.00 | 3.00 | 3.00 | 3.00 | 3.00 | 3.00 | 3.00 | 3.00 |
| pH | 7.00 | 7.00 | 7.00 | 7.00 | 7.00 | 7.00 | 7.00 | 7.00 | 7.00 | 7.00 | 7.00 |
| Osmolarity (mOsm) | 15 (d) | 15 (d) | 12 (d) | 12 (d) | 16 (d) | | | | | | |
| Shear Rate | 10-1000 | 10-1000 | 10-1000 | 10-1000 | 10-1000 | | | | | | |
| Viscosity (cps) | 164 | 214 | 181 | 233 | 192 | | | | | | |

(d) denotes diluted ten times

AQus™ CL-Tears may represent compositions with the following ingredients and concentrations:
 3.0% polysorbate 80
 0.10% poloxamer 188
 0.01% polyoxyl castor oil
 0.50% HPMC
 0.5% to 2.5% mannitol (1.0% preferred)
 0.10% MgCl$_2$
 0.1% to 0.75% NaCl, preferably 0.2% to 0.5%
 optionally 1.0% glycerin
 2-3 mM phosphate buffer
 pH 7.0

AQus™ CL-Tears may also represent compositions with the following ingredients and concentrations:
 0.0% to 1.5% polysorbate 80
 0.10% poloxamer 188
 0.01% polyoxyl castor oil
 1.5% to 3.0% hydroxy propyl gamma cyclodextrin
 0.50% HPMC
 0% to 2.5% mannitol (1.0% preferred)
 0% to 0.10% MgCl$_2$
 0.1% to 0.75% NaCl, preferably 0.2% to 0.5%
 optionally 1.0% glycerin
 2-3 mM phosphate buffer
 pH 7.0

AQus™ CL-Tears may also represent compositions may represent composition of Table 3.

TABLE 3

AQus™ CL-Tears Compositions

| (% w/v) | 58 | 59 | 60 | 61 | 62 | 63 | 64 | 65 | 66 |
|---|---|---|---|---|---|---|---|---|---|
| Polysorbate 80 | 3.00% | 3.00% | 3.00% | 2.50% | 2.00% | 1.50% | 1.50% | 1.50% | 1.00% |
| Poloxamer 407 | — | 0.20% | 0.20% | 0.10% | 0.20% | 0.20% | 0.20% | 0.20% | 0.20% |
| Poloxamer 188 | 0.10% | 0.10% | 0.10% | 1.00% | 0.50% | 1.00% | 0.10% | 1.00% | 0.10% |
| Polyoxyl Castor oil | 0.01% | 0.01% | 0.01% | 0.01% | 0.01% | 0.01% | 0.01% | 0.01% | 0.01% |
| Hydroxypropyl-gamma-cyclodextrin | — | — | 0.50% | 0.25% | 1.00% | 0.50% | 1.50% | 1.00% | 1.50% |
| HPMC | 0.10% | 0.10% | 0.10% | 0.10% | 0.10% | — | — | 0.10% | — |
| CMC (% HPMC equivalent) | — | — | — | — | — | 0.10% | 0.10% | — | 0.10% |
| PEG 400 | — | — | — | 0.50% | 0.25% | — | — | — | — |
| Mannitol | 1.00% | 1.00% | 1.00% | 2.50% | 1.00% | — | 1.00% | 1.00% | — |
| MgCl$_2$ | 0.10% | 0.10% | 0.10% | 0.10% | 0.10% | 0.10% | 0.10% | 0.10% | 0.10% |
| NaCl* | 0.30% | 0.30% | 0.30% | 0.30% | 0.30% | 0.40% | 0.40% | 0.40% | 0.30% |
| Phosphate buffer (mM) | 3.00 | 3.00 | 3.00 | 3.00 | 3.00 | 3.00 | 3.00 | 3.00 | 3.00 |
| pH | 7.00 | 7.00 | 7.00 | 7.00 | 7.00 | 7.00 | 7.00 | 7.00 | 7.00 |
| Menthol (mM) | — | — | — | — | — | — | — | — | — |
| viscosity (cps) | 2.00 | 2.00 | 2.00 | >100 | 2.00 | 2.00 | 2.00 | 2.00 | 2.00 |

| (% w/v) | 67 | 68 | 69 | 70 | 71 | 72 | 73 | 74 | 75 |
|---|---|---|---|---|---|---|---|---|---|
| Polysorbate 80 | 1.00% | 1.00% | 1.00% | 1.00% | 1.00% | 1.00% | 0.50% | 0.50% | 1.50% |
| Poloxamer 407 | 0.20% | 0.20% | 0.20% | 1.00% | 1.00% | 1.00% | — | — | 0.20% |
| Poloxamer 188 | 0.10% | 0.50% | 1.00% | 1.00% | 1.00% | 1.00% | 0.10% | 0.10% | 0.10% |
| Polyoxyl Castor oil | 0.50% | 0.10% | 0.01% | 0.01% | 0.01% | 0.01% | 0.01% | 0.01% | 1.00% |
| Hydroxypropyl-gamma-cyclodextrin | 1.50% | 1.50% | 1.50% | — | — | — | 2.50% | 3.00% | 0.50% |
| HPMC | 0.10% | 0.10% | — | 0.10% | — | 0.10% | 0.10% | 0.10% | — |
| CMC (% HPMC equivalent) | — | — | 0.10% | — | 0.10% | — | — | — | — |
| PEG 400 | — | — | — | — | — | — | — | — | 1.00% |
| Mannitol | — | — | — | 1.00% | 1.00% | 1.00% | 1.00% | 1.00% | — |
| MgCl$_2$ | 0.10% | 0.10% | 0.10% | 0.10% | 0.10% | 0.10% | 0.10% | 0.10% | 0.10% |
| NaCl* | 0.30% | 0.30% | 0.30% | 0.30% | 0.40% | 0.40% | 0.40% | 0.40% | 0.40% |
| Phosphate buffer (mM) | 3.00 | 3.00 | 3.00 | 3.00 | 3.00 | 3.00 | 3.00 | 3.00 | 3.00 |
| pH | 7.00 | 7.00 | 7.00 | 7.00 | 7.00 | 7.00 | 7.00 | 7.00 | 7.0 |
| Menthol (mM) | 0.05 | — | — | — | — | — | — | — | — |
| viscosity (cps) | 2.00 | 2.00 | 2.00 | 2.00 | 2.00 | 2.00 | 2.00 | 2.00 | 2.00 |

| (% w/v) | 76 | 77 | 78 | 79 | 80 | 81 | 82 | 83 | 84 |
|---|---|---|---|---|---|---|---|---|---|
| Polysorbate 80 | 1.00% | 1.00% | 2.00% | 2.00% | 2.00% | 2.00% | 2.00% | 2.00% | 2.00% |
| Poloxamer 407 | 0.50% | 0.50% | 0.10% | 0.10% | 0.10% | 0.10% | 0.10% | 0.10% | 0.10% |
| Poloxamer 188 | 1.00% | 1.00% | 0.10% | 0.10% | 0.10% | 0.10% | 0.10% | 0.10% | 0.10% |
| Polyoxyl Castor oil | 0.01% | 0.01% | 0.01% | 0.01% | 0.01% | 0.01% | 0.01% | 0.01% | 0.01% |
| HPMC | 0.50% | 0.50% | 0.50% | 0.20% | 0.50% | 0.50% | 0.50% | 0.50% | 0.50% |
| PEG 400 | 0.25% | 0.25% | 0.25% | 0.20% | 0.25% | 0.25% | 0.25% | 0.25% | 0.25% |
| Mannitol | 0.25% | 0.25% | 0.25% | 0.20% | 0.25% | 1.00% | 0.25% | 0.50% | 0.50% |
| MgCl$_2$ | 0.10% | 0.10% | 0.10% | 0.10% | 0.10% | 0.10% | 0.10% | 0.10% | 0.10% |
| NaCl* | 0.30% | 0.30% | 0.25% | 0.25% | 0.25% | 0.35% | 0.25% | 0.40% | 0.40% |
| Citrate buffer (mM) | 4.00 | 4.00 | 4.00 | — | — | — | — | — | — |
| pH | 7.00 | 7.00 | 7.00 | 7.00 | 7.00 | 7.00 | 7.00 | 7.00 | 7.00 |
| Menthol (mM) | 0.04 | 0.04 | 0.02 | 0.02 | — | 0.08 | 0.08 | 0.12 | 0.13 |
| Sorbate | — | 0.1% | 0.1% | 0.1% | — | — | — | — | — |

| (% w/v) | 85 | 86 | 87 | 88 | 89 | 90 | 91 | 92 | 93 |
|---|---|---|---|---|---|---|---|---|---|
| Polysorbate 80 | 2.00% | 2.00% | 2.00% | 2.00% | 2.00% | 2.00% | 2.00% | 2.00% | 2.00% |
| Poloxamer 407 | 0.10% | 0.10% | 0.10% | 0.10% | 0.10% | 0.10% | 0.10% | 0.10% | 0.10% |
| Poloxamer 188 | 0.10% | 0.10% | 0.10% | 0.10% | 0.10% | 0.10% | 0.10% | 0.10% | 0.10% |
| Polyoxyl Castor oil | 0.01% | 0.01% | 0.01% | 0.01% | 0.01% | 0.01% | 0.01% | 0.01% | 0.01% |
| HPMC | 0.50% | 0.50% | 0.50% | 0.20% | 0.50% | 0.50% | 0.50% | 0.50% | 0.50% |
| PEG 400 | 0.25% | 0.25% | 0.25% | 0.20% | 0.25% | 0.25% | 0.25% | 0.25% | 0.25% |
| Mannitol | 0.50% | 0.50% | 0.50% | 0.20% | 0.25% | 1.00% | 0.25% | 0.50% | 0.50% |
| MgCl$_2$ | 0.10% | 0.10% | 0.10% | 0.10% | 0.10% | 0.10% | 0.10% | 0.10% | 0.10% |
| NaCl* | 0.40% | 0.40% | 0.40% | 0.25% | 0.25% | 0.25% | 0.25% | 0.40% | 0.40% |
| Citrate buffer (mM) | — | — | — | 4.00 | 4.00 | 4.00 | 4.00 | 4.00 | 4.00 |
| pH | 7.00 | 7.00 | 7.00 | 7.00 | 7.00 | 7.00 | 7.00 | 7.00 | 7.00 |
| Menthol (mM) | 0.14 | 0.15 | 0.16 | — | — | 0.08 | 0.08 | 0.12 | 0.13 |
| Sorbate | — | — | — | 0.1 | 0.1 | 0.1 | 0.1 | 0.1 | 0.1 |
| EDTA | — | — | — | 0.1 | 0.1 | 0.1 | 0.1 | 0.1 | 0.1 |

| (% w/v) | 94 | 95 | 96 |
|---|---|---|---|
| Polysorbate 80 | 2.00% | 2.00% | 2.00% |
| Poloxamer 407 | 0.10% | 0.10% | 0.10% |
| Poloxamer 188 | 0.10% | 0.10% | 0.10% |
| Polyoxyl Castor oil | 0.01% | 0.01% | 0.01% |
| HPMC | 0.50% | 0.50% | 0.50% |

TABLE 3-continued

| AQus™ CL-Tears Compositions | | | |
|---|---|---|---|
| PEG 400 | 0.25% | 0.25% | 0.25% |
| Mannitol | 0.50% | 0.50% | 0.50% |
| MgCl₂ | 0.10% | 0.10% | 0.10% |
| NaCl* | 0.40% | 0.40% | 0.40% |
| Citrate buffer (mM) | 4.00 | 4.00 | 4.00 |
| pH | 7.00 | 7.00 | 7.00 |
| Menthol (mM) | 0.14 | 0.15 | 0.16 |
| Sorbate | 0.1 | 0.1 | 0.1 |
| EDTA | 0.1 | 0.1 | 0.1 |

*NaCl may be at a concentration from 0.1% to 0.75%, preferably from 0.2% to 0.5%
"% HPMC equivalent" denotes an amount of CMC necessary to result in a final viscosity equivalent to the final viscosity achieved if the given % w/v of HPMC were used.

AQus™ Tears Plus may represent compositions of Table 4.

TABLE 4

| AQus™ Tears Plus Compositions | | | | | | | | |
|---|---|---|---|---|---|---|---|---|
| (% w/v) | 97 | 98 | 99 | 100 | 101 | 102 | 103 | 104 |
| Polysorbate 80 | 3.50% | 3.00% | 3.00% | 3.00% | 2.75% | 2.00% | 2.00% | 1.50% |
| Poloxamer 407 | 0.20% | 0.10% | 0.10% | — | 0.20% | 0.20% | 0.20% | 0.20% |
| Poloxamer 188 | 0.10% | 0.50% | 0.10% | — | 0.10% | 0.50% | 0.10% | 0.75% |
| Polyoxyl Castor oil | 0.01% | 0.01% | 0.01% | 0.01% | 0.01% | 0.01% | 0.01% | 0.01% |
| Hydroxypropyl-gamma-cyclodextrin | — | 0.25% | 0.70% | — | 0.75% | 1.00% | 1.50% | 1.50% |
| HPMC | 0.85% | 1.25% | 1.00% | 0.65% | 1.00% | 1.25% | 1.25% | 1.00% |
| CMC (% HPMC equivalent) | — | — | — | — | — | — | — | — |
| PEG 400 | — | 0.25% | — | — | — | — | — | — |
| Mannitol | 2.50% | 2.50% | 2.50% | 2.50% | 2.50% | 2.50% | 2.50% | 2.50% |
| MgCl₂ | 0.10% | 0.10% | 0.10% | 0.10% | 0.10% | 0.10% | 0.10% | 0.10% |
| NaCl* | 0.25% | 0.30% | 0.30% | 0.30% | 0.40% | 0.25% | 0.30% | 0.30% |
| Phosphate buffer (mM) | 3.00 | 3.00 | — | 3.00 | 3.00 | — | — | — |
| Citrate buffer (mM) | — | — | 3.00 | — | — | 3.00 | 3.00 | 3.00 |
| pH | 7.00 | 7.00 | 5.50 | 7.00 | 7.00 | 5.50 | 6.00 | 5.50 |
| Menthol (mM) | 0.07 | 0.12 | 0.07 | — | 0.15 | 0.17 | 0.15 | 0.15 |
| Sorbate | — | — | 0.10% | — | — | — | — | — |

| (% w/v) | 105 | 106 | 107 | 108 | 109 | 110 | 111 | 112 |
|---|---|---|---|---|---|---|---|---|
| Polysorbate 80 | 1.50% | 1.50% | 1.00% | 1.00% | 0.50% | 0.50% | 0.50% | 0.50% |
| Poloxamer 407 | 0.20% | 0.20% | 1.00% | — | — | — | — | — |
| Poloxamer 188 | 0.50% | 0.10% | 1.00% | 0.10% | 0.10% | 0.10% | 0.10% | 0.10% |
| Polyoxyl Castor oil | 0.01% | 0.01% | 0.01% | — | 0.01% | 0.01% | 0.01% | 0.01% |
| Hydroxypropyl-gamma-cyclodextrin | 1.50% | 1.50% | — | 2.00% | 3.00% | 3.00% | 3.00% | 3.00% |
| HPMC | 1.35% | — | 0.65% | 0.75% | 0.75% | — | 0.75% | 0.75% |
| CMC (% HPMC equivalent) | — | 1.00% | — | — | — | 0.75% | — | — |
| PEG 400 | — | — | — | — | — | — | — | — |
| Mannitol | 1.00% | 2.50% | 2.50% | 2.50% | 2.50% | 2.50% | 2.50% | 2.50% |
| MgCl₂ | 0.10% | 0.10% | 0.10% | 0.10% | 0.10% | 0.10% | 0.10% | 0.10% |
| NaCl* | 0.40% | 0.30% | 0.30% | 0.40% | 0.40% | 0.40% | 0.40% | 0.40% |
| Phosphate buffer (mM) | 3.00 | 3.00 | 3.00 | 3.00 | 3.00 | 3.00 | 3.00 | 3.00 |
| Citrate buffer (mM) | — | — | — | — | — | — | — | — |
| pH | 7.00 | 6.00 | 7.00 | 7.00 | 6.00 | 6.00 | 6.00 | 6.00 |
| Menthol (mM) | 0.12 | 0.10 | — | — | 0.10 | 0.10 | — | — |
| Sorbate | — | — | — | — | — | — | 0.10% | — |

| (% w/v) | 113 | 114 | 115 | 115B | 115C | 115D | 115E |
|---|---|---|---|---|---|---|---|
| Polysorbate 80 | 1.5% | 1.5% | 3.0% | 1.00% | 1.00% | 1.00% | 1.00% |
| Poloxamer 407 | 0.7% | 0.7% | 0.1% | 0.50% | 0.50% | 1.00% | 1.00% |
| Poloxamer 188 | 1.0% | 1.0% | 0.1% | 1.00% | 1.00% | 0.20% | 0.20% |
| Polyoxyl Castor oil | 0.01% | 0.01% | 0.01% | 0.01% | 0.01% | 0.01% | 0.01% |
| Hydroxypropyl-gamma-cyclodextrin | — | — | — | — | — | 1.50% | 1.50% |
| HPMC | 0.95% | 0.95% | 0.95% | 0.50% | 0.50% | 0.20% | 0.20% |
| CMC (% HPMC equivalent) | — | — | — | — | — | — | — |
| PEG 400 | 1.0% | 1.0% | 2.0% | 0.25% | 0.25% | 0.50% | 0.50% |
| Mannitol | 0.5% | 0.5% | 0.5% | 0.25% | 0.25% | 1.00% | 1.00% |
| MgCl₂ | 0.1% | 0.1% | 0.1% | 0.10% | 0.10% | 0.10% | 0.10% |
| NaCl* | 0.35% | 0.35% | 0.4% | 0.30% | 0.30% | 0.35% | 0.4% |
| Phosphate buffer (mM) | — | — | — | — | — | 3.00 | 3.00 |
| Citrate buffer (mM) | 4.00 | 4.00 | 4.00 | 4.00 | 4.00 | — | — |

TABLE 4-continued

| AQus™ Tears Plus Compositions | | | | | | | |
|---|---|---|---|---|---|---|---|
| pH | 7 | 7 | 7 | 7.00 | 7.00 | 7.0 | 7.0 |
| Menthol (mM) | 0.09 | 0.09 | 0.09 | 0.02 | 0.02 | 0.10 | 0.01 |
| Sorbate | — | 0.1% | 0.1% | — | 0.1% | — | — |

*NaCl may be at a concentration from 0.1% to 0.75%, preferably from 0.2% to 0.5%
"% HPMC equivalent" denotes an amount of CMC necessary to result in a final viscosity equivalent to the final viscosity achieved if the given % w/v of HPMC were used AQus™ Tears Advanced may represent compositions of Table 5.

TABLE 5

| AQus™ Tears Advanced Compositions | | | | | | | | |
|---|---|---|---|---|---|---|---|---|
| (% w/v) | 116 | 117 | 118 | 119 | 120 | 121 | 122 | 123 |
| Polysorbate 80 | 3.50% | 3.00% | 2.75% | 2.00% | 1.50% | 1.50% | 1.50% | 1.50% |
| Poloxamer 407 | 0.20% | 0.10% | 0.20% | 0.20% | 0.20% | 0.20% | 0.20% | 0.20% |
| Poloxamer 188 | 0.10% | 0.10% | 0.10% | 0.10% | 0.75% | 0.50% | 0.50% | 0.10% |
| Polyoxyl Castor oil | 0.01% | 0.01% | 0.01% | 0.01% | 0.01% | 0.01% | 0.01% | 0.01% |
| Hydroxypropyl-gamma-cyclodextrin | — | 0.70% | 0.75% | 1.50% | 1.50% | 1.50% | 1.50% | 2.00% |
| HPMC | 1.25% | 1.40% | 1.25% | 1.30% | 1.35% | 1.35% | 1.35% | 1.35% |
| CMC (% HPMC equivalent) | — | — | — | — | 0.25% | — | — | — |
| PEG 400 | — | — | — | 0.25% | — | — | — | — |
| Mannitol | 2.50% | 2.50% | 2.50% | 2.50% | 2.50% | 2.50% | 2.50% | 2.50% |
| MgCl$_2$ | 0.10% | 0.10% | 0.10% | 0.10% | 0.10% | 0.10% | 0.10% | 0.10% |
| NaCl* | 0.25% | 0.30% | 0.25% | 0.30% | 0.40% | 0.40% | 0.40% | 0.25% |
| Citrate Buffer (mM) | 3.00 | 3.00 | 3.00 | 3.00 | 3.00 | 3.00 | 3.00 | 3.00 |
| pH | 5.50 | 5.00 | 5.50 | 5.50 | 5.50 | 5.50 | 5.50 | 5.00 |
| Menthol (mM) | 0.15 | 0.20 | 0.15 | 0.17 | 0.15 | 0.17 | 0.15 | 0.17 |
| Sorbate | — | — | — | — | — | — | 0.10% | — |

| (% w/v) | 124 | 125 | 126 | 127 | 128 | 129 | 130 |
|---|---|---|---|---|---|---|---|
| Polysorbate 80 | 0.50% | 0.50% | 0.50% | 0.50% | 0.50% | 2.00% | 0.50% |
| Poloxamer 407 | — | — | — | — | — | 0.20% | — |
| Poloxamer 188 | — | 0.10% | 0.10% | 0.10% | 0.10% | 0.10% | 0.10% |
| Polyoxyl Castor oil | — | 0.01% | 0.01% | 0.01% | 0.01% | 0.01% | 0.01% |
| Hydroxypropyl-gamma-cyclodextrin | 3.50% | 3.50% | 4.00% | 4.00% | 4.00% | 1.50% | 4.00% |
| HPMC | 1.00% | 1.00% | 1.25% | — | 1.25% | — | 1.25% |
| CMC (% HPMC equivalent) | — | — | — | 1.25% | — | 1.30% | — |
| Mannitol | 2.50% | 2.50% | 2.50% | 2.50% | 2.50% | 2.50% | 2.50% |
| PEG 400 | — | — | — | — | — | — | — |
| MgCl$_2$ | 0.10% | 0.10% | 0.10% | 0.10% | 0.10% | 0.10% | 0.10% |
| NaCl* | 0.30% | 0.40% | 0.40% | 0.40% | 0.40% | 0.30% | 0.40% |
| Citrate Buffer (mM) | 3.00 | 3.00 | 3.00 | 3.00 | 3.00 | 3.00 | 3.00 |
| pH | 6.00 | 7.00 | 5.50 | 5.50 | 5.50 | 5.50 | 5.50 |
| Menthol (mM) | — | — | 0.10 | 0.10 | — | 0.10 | — |
| Sorbate | — | — | — | — | 0.10% | 0.10% | — |

| (% w/v) | 131B | 131C | 131D | 131E | 131F | 131G |
|---|---|---|---|---|---|---|
| Polysorbate 80 | 1.00% | 1.00% | 1.00% | 1.00% | 1.00% | 1.00% |
| Poloxamer 407 | 0.50% | 0.50% | 0.50% | 0.50% | 1.00% | 1.00% |
| Poloxamer 188 | 1.00% | 1.00% | 1.00% | 1.00% | 0.20% | 0.20% |
| Polyoxyl Castor oil | 0.01% | 0.01% | 0.5% | 0.5% | 0.01% | 0.25% |
| Hydroxypropyl-gamma-cyclodextrin | — | — | — | — | 1.50% | 1.50% |
| HPMC | 0.50% | 0.50% | 0.85% | 0.85% | 0.75% | 1.00% |
| Mannitol | 0.25% | 0.25% | 0.25% | 0.25% | 1.00% | 1.00% |
| PEG 400 | 0.25% | 0.25% | 0.25% | 0.25% | 0.50% | 0.50% |
| MgCl$_2$ | 0.10% | 0.10% | 0.10% | 0.10% | 0.10% | 0.10% |
| NaCl* | 0.30% | 0.30% | 0.30% | 0.30% | 0.35% | 0.35% |
| Phosphate Buffer (mM) | — | — | — | — | 4.00 | 4.00 |
| Citrate Buffer (mM) | 4.00 | 4.00 | 4.00 | 4.00 | — | — |
| pH | 7.00 | 7.00 | 7.00 | 7.00 | 6.0 | 6.2 |
| Menthol (mM) | 0.04 | 0.04 | 0.06 | 0.06 | 0.30 | 0.27 |
| Sorbate | — | 0.10% | — | 0.10% | 0.11% | 0.10% |

*NaCl may be at a concentration from 0.1% to 0.75%, preferably from 0.2% to 0.5%
"% HPMC equivalent" denotes an amount of CMC necessary to result in a final viscosity equivalent to the final viscosity achieved if the given % w/v of HPMC were used AQus™ Tears Advanced Plus or AQus™ Tears Extreme may represent compositions of Table 6.

TABLE 6

AQus ™ Tears Advanced Plus and AQus ™ Tears Extreme Compositions

| (% w/v) | 131 | 132 | 133 | 134 | 135 | 136 | 137 | 138 |
|---|---|---|---|---|---|---|---|---|
| Polysorbate 80 | 3.50% | 2.75% | 2.00% | 2.00% | 1.50% | 1.50% | 0.50% | 0.50% |
| Poloxamer 407 | 0.20% | 0.20% | 0.20% | 0.20% | 0.20% | 0.20% | — | — |
| Poloxamer 188 | 0.10% | 0.10% | 0.10% | 0.10% | 0.75% | 0.10% | 0.40% | 0.40% |
| Polyoxyl Castor oil | 0.01% | 0.01% | 0.01% | 0.01% | 0.01% | 0.01% | 0.01% | 0.01% |
| Hydroxypropyl-gamma-cyclodextrin | — | 0.75% | 1.50% | 1.50% | 1.50% | 2.00% | 4.50% | 4.50% |
| HPMC | 1.45% | 1.40% | 1.40% | — | 1.45% | 1.40% | 1.35% | 1.40% |
| CMC (% HPMC equivalent) | — | — | — | 1.40% | — | — | — | — |
| PEG 400 | — | — | — | — | — | 0.25% | — | — |
| Mannitol | 2.50% | 2.50% | 2.50% | 2.50% | 2.50% | 2.50% | 2.50% | 2.50% |
| MgCl$_2$ | 0.10% | 0.10% | 0.10% | 0.10% | 0.10% | 0.10% | 0.10% | 0.10% |
| NaCl* | 0.25% | 0.25% | 0.40% | 0.30% | 0.25% | 0.35% | 0.40% | 0.40% |
| Citrate Buffer (mM) | 3.00 | 3.00 | 3.00 | 3.00 | 3.00 | 3.00 | 3.00 | 3.00 |
| pH | 5.00 | 5.00 | 5.00 | 5.50 | 5.00 | 5.00 | 7.00 | 5.50 |
| Menthol (mM) | 0.15 | 0.17 | 0.25 | 0.15 | 0.25 | 0.20 | — | 0.10 |
| Sorbate | — | — | — | — | 0.10% | — | — | — |

| (% w/v) | 139 | 140 | 141 | 142 | 143 | 144 | 145 |
|---|---|---|---|---|---|---|---|
| Polysorbate 80 | 0.50% | 0.50% | 0.50% | 0.50% | 1.75% | 1.75% | 3.5% |
| Poloxamer 407 | — | — | — | — | 0.75% | 0.75% | 0.1% |
| Poloxamer 188 | 0.40% | 0.40% | 0.40% | 0.40% | 1.25% | 1.25% | 0.1% |
| Polyoxyl Castor oil | 0.01% | 0.01% | 0.01% | 0.01% | 0.01% | 0.01% | 0.01% |
| Hydroxypropyl-gamma-cyclodextrin | 5.00% | 5.00% | 5.00% | 5.00% | — | — | — |
| HPMC | 1.40% | 1.45% | — | 1.40% | 1.1% | 1.1% | 1.1% |
| CMC (% HPMC equivalent) | — | — | 1.40% | — | — | — | — |
| PEG 400 | — | — | — | — | 0.25% | 0.25% | 2.5% |
| Mannitol | 2.50% | 2.50% | 2.50% | 2.50% | 0.75% | 0.75% | 1.0% |
| MgCl$_2$ | 0.10% | 0.10% | 0.10% | 0.10% | 0.05% | 0.05% | 0.1% |
| NaCl* | 0.40% | 0.40% | 0.40% | 0.40% | 0.40% | 0.40% | 0.40% |
| Citrate Buffer (mM) | 3.00 | 3.00 | 3.00 | 3.00 | 4.00 | 4.00 | 4.00 |
| pH | 7.00 | 5.50 | 5.50 | 5.50 | 7 | 7 | 7 |
| Menthol (mM) | — | 0.15 | 0.15 | 0.15 | 0.12 | 0.12 | 0.12 |
| Sorbate | — | 0.10% | — | — | — | 0.1% | 0.1% |

| (% w/v) | 145B | 145C | 145D | 145E | 145F | 145G | 145H | 145I |
|---|---|---|---|---|---|---|---|---|
| Polysorbate 80 | 1.00% | 1.00% | 1.00% | 1.00% | 1.00% | 1.00% | 1.00% | 1.00% |
| Poloxamer 407 | 0.50% | 0.50% | 0.50% | 0.50% | 0.50% | 0.50% | 0.50% | 0.50% |
| Poloxamer 188 | 1.00% | 1.00% | 1.00% | 1.00% | 1.00% | 1.00% | 1.00% | 1.00% |
| Polyoxyl Castor oil | 0.01% | 0.01% | 0.01% | 0.01% | 0.01% | 0.01% | 0.01% | 0.01% |
| HPMC | 0.50% | 0.50% | 0.50% | 0.50% | 0.50% | 1.1% | 1.1% | 1.2% |
| Mannitol | 0.25% | 0.25% | 0.25% | 0.25% | 0.25% | 0.25% | 0.25% | 0.25% |
| PEG 400 | 0.25% | 0.25% | 0.25% | 0.25% | 0.25% | 0.25% | 0.25% | 0.25% |
| MgCl$_2$ | 0.10% | 0.10% | 0.10% | 0.10% | 0.10% | 0.10% | 0.10% | 0.10% |
| NaCl* | 0.30% | 0.30% | 0.30% | 0.30% | 0.30% | 0.30% | 0.30% | 0.30% |
| Citrate Buffer (mM) | 4.00 | 4.00 | 4.00 | 4.00 | 4.00 | 4.00 | 4.00 | 4.00 |
| pH | 7.00 | 7.00 | 7.00 | 7.00 | 7.00 | 7.00 | 7.00 | 7.00 |
| Menthol (mM) | 0.06 | 0.09 | 0.09 | 0.12 | 0.15 | 0.09 | 0.09 | 0.09 |
| Sorbate | — | — | 0.10% | — | — | — | 0.10% | — |

| (% w/v) | 145J | 145K | 145L | 145M | 145N | 145O | 145P |
|---|---|---|---|---|---|---|---|
| Polysorbate 80 | 1.00% | 1.00% | 1.00% | 1.50% | 1.50% | 1.50% | 1.00% |
| Poloxamer 407 | 0.50% | 0.50% | 0.50% | 0.70% | 0.70% | 0.70% | 1.00% |
| Poloxamer 188 | 1.00% | 1.00% | 1.00% | 1.00% | 1.00% | 1.00% | 0.20% |
| Polyoxyl Castor oil | 0.01% | 0.75% | 0.75% | 0.25% | 0.25% | 0.25% | 0.15% |
| Hydroxypropyl-gamma-cyclodextrin | — | — | — | — | — | — | 1.50% |
| HPMC | 1.2% | 1.15% | 1.15% | 1.10% | 1.10% | 1.10% | 1.00% |
| Mannitol | 0.25% | 1.75% | 1.75% | 2.50% | 2.50% | 2.50% | 1.00% |
| PEG 400 | 0.25% | 0.25% | 0.25% | — | — | — | 0.50% |
| MgCl$_2$ | 0.10% | 0.05% | 0.05% | 0.10% | 0.10% | 0.10% | 0.10% |
| NaCl* | 0.30% | 0.25% | 0.25% | 0.25% | 0.25% | 0.25% | 0.35% |
| Citrate Buffer (mM) | 4.00 | 4.00 | 4.00 | — | — | — | 4.00 |
| Phosphate Buffer (mM) | — | — | — | 3.00 | 3.00 | 3.00 | — |
| pH | 7.00 | 7.00 | 7.00 | 5.7 | 5.7 | 5.7 | 5.7 |
| Menthol (mM) | 0.09 | 0.09 | 0.09 | — | 0.20 | 0.25 | 0.30 |
| Sorbate | 0.10% | — | 0.10% | 0.10% | 0.10% | 0.10% | 0.11% |

TABLE 6-continued

AQus ™ Tears Advanced Plus and AQus ™ Tears Extreme Compositions

| (% w/v) | 145Q | 145R | 145S | 145T | 145U | 145V | 145W |
|---|---|---|---|---|---|---|---|
| Polysorbate 80 | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.25% | 0.30% |
| Hydroxypropyl-gamma-cyclodextrin | 1.50% | 1.50% | 1.50% | 1.50% | 1.50% | 1.50% | 1.50% |
| HPMC | 1.20% | 1.20% | 1.20% | 1.20% | 1.20% | 1.20% | 1.20% |
| Mannitol | 1.00% | 1.00% | 1.00% | 1.00% | 1.00% | 1.00% | 1.00% |
| PEG 400 | 0.50% | 0.50% | 0.50% | 0.50% | 0.50% | 0.50% | 0.50% |
| $MgCl_2$ | 0.10% | 0.10% | 0.10% | 0.10% | 0.10% | 0.10% | 0.10% |
| NaCl* | 0.35% | 0.35% | 0.35% | 0.35% | 0.35% | 0.35% | 0.35% |
| Phosphate Buffer (mM) | 3.00 | 4.00 | 3.00 | 4.00 | 3.00 | 4.00 | 3.00 |
| pH | 5.7 | 5.7 | 6.0 | 6.0 | 6.2 | 6.2 | 6.2 |
| Menthol (mM) | 0.27 | 0.27 | 0.27 | 0.27 | 0.27 | 0.27 | 0.27 |
| Sorbate | 0.10% | 0.10% | 0.10% | 0.10% | 0.10% | 0.10% | 0.10% |

| (% w/v) | 145X | 145Y | 145Z | 145AA | 145AB | 145AC | 145AD |
|---|---|---|---|---|---|---|---|
| Polysorbate 80 | 1.50% | 1.50% | 1.50% | 1.50% | 1.50% | 1.50% | 1.50% |
| Poloxamer 407 | 0.70% | 0.70% | 0.70% | 0.70% | 0.70% | 0.70% | 0.70% |
| Poloxamer 188 | 1.00% | 1.00% | 1.00% | 1.00% | 1.00% | 1.00% | 1.00% |
| Polyoxyl Castor oil | 0.25% | 0.25% | 0.25% | 0.25% | 0.25% | 0.25% | 0.30% |
| Hydroxypropyl-gamma-cyclodextrin | 1.50% | 1.50% | 1.50% | 1.50% | 1.50% | 1.50% | 1.50% |
| HPMC | 1.20% | 1.20% | 1.20% | 1.20% | 1.20% | 1.20% | 1.20% |
| Mannitol | 1.00% | 1.00% | 1.00% | 1.00% | 1.00% | 1.00% | 1.00% |
| PEG 400 | 0.50% | 0.50% | 0.50% | 0.50% | 0.50% | 0.50% | 0.50% |
| $MgCl_2$ | 0.10% | 0.10% | 0.10% | 0.10% | 0.10% | 0.10% | 0.10% |
| NaCl* | 0.35% | 0.35% | 0.35% | 0.35% | 0.35% | 0.35% | 0.35% |
| Phosphate Buffer (mM) | 3.00 | 4.00 | 3.00 | 4.00 | 3.00 | 4.00 | 4.00 |
| pH | 5.7 | 5.7 | 6.0 | 6.0 | 6.2 | 6.2 | 6.2 |
| Menthol (mM) | 0.27 | 0.27 | 0.27 | 0.27 | 0.27 | 0.27 | 0.27 |
| Sorbate | 0.10% | 0.10% | 0.10% | 0.10% | 0.10% | 0.10% | 0.11% |

| (% w/v) | 145AE | 145AF | 145AG | 145AH | 145AI | 145AJ | 145AK |
|---|---|---|---|---|---|---|---|
| Polysorbate 80 | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.01% | 0.25% |
| Hydroxypropyl-gamma-cyclodextrin | 1.50% | 1.50% | 1.50% | 2.50% | 1.50% | 1.50% | 1.50% |
| HPMC | — | — | 0.20% | 1.00% | 1.20% | 0.20% | 0.70% |
| Mannitol | 1.00% | 1.00% | 1.00% | 1.00% | 1.00% | 1.00% | 1.00% |
| PEG 400 | 0.50% | 0.50% | 0.50% | 1.00% | 0.50% | 0.50% | 0.50% |
| $MgCl_2$ | 0.10% | 0.10% | 0.10% | 0.10% | 0.10% | 0.10% | 0.10% |
| NaCl* | 0.35% | 0.35% | 0.35% | 0.35% | 0.35% | 0.45% | 0.45% |
| Phosphate Buffer (mM) | 4.00 | 4.00 | 4.00 | 4.00 | 3.00 | — | — |
| Citrate Buffer (mM) | — | — | — | — | — | 3.00 | 3.00 |
| pH | 6.2 | 6.2 | 6.2 | 6.2 | 6.2 | 7.0 | 7.0 |
| Menthol (mM) | 0.15 | 0.25 | 0.01 | 0.37 | 0.01 | 0.10 | 0.27 |
| Vitamin E (alpha-tocopherol) International units | — | — | — | — | 129.1 | — | 10 |
| Sorbate | 0.10% | 0.10% | 0.10% | 0.10% | 0.10% | — | 0.10% |

| (% w/v) | 145AL | 145AM | 145AN | 145AO | 145AP | 145AQ | 145AR |
|---|---|---|---|---|---|---|---|
| Polysorbate 80 | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% |
| Polyoxyl Castor oil | 0.25% | 0.25% | 0.01% | 0.25% | 0.25% | 0.25% | 0.25% |
| Hydroxypropyl-gamma-cyclodextrin | 1.50% | 1.50% | 1.50% | 1.50% | 1.50% | 1.50% | 1.50% |
| HPMC | 0.85% | 0.50% | 0.20% | 1.00% | 1.20% | 0.50% | 1.10% |
| Mannitol | 1.00% | 0.75% | 1.00% | 1.00% | 1.00% | 0.75% | 0.75% |
| PEG 400 | 0.50% | 0.50% | 0.50% | 0.50% | 0.50% | 0.50% | 0.50% |
| $MgCl_2$ | 0.10% | 0.10% | 0.10% | 0.10% | 0.10% | 0.10% | 0.10% |
| NaCl* | 0.45% | 0.35% | 0.40% | 0.35% | 0.35% | 0.35% | 0.35% |
| Phosphate Buffer (mM) | — | — | 3.00 | 4.00 | 4.00 | 4.00 | 4.00 |
| Citrate Buffer (mM) | 4.00 | 3.00 | — | — | — | 3.00 | 3.00 |
| pH | 6.5 | 7.0 | 7.0 | 6.2 | 6.2 | 7.0 | 7.0 |
| Menthol (mM) | 0.32 | 0.32 | 0.01 | 0.27 | 0.27 | 0.30 | 0.30 |
| Vitamin E (alpha-tocopherol) International units | 15 | 35 | — | — | — | — | — |
| Sorbate | 0.10% | 0.10% | — | 0.10% | 0.10% | 0.10% | 0.10% |

TABLE 6-continued

| (% w/v) | 145AS | 145AT | 145AU | 145AV | 145AW | 145AX | 145AY |
|---|---|---|---|---|---|---|---|
| Polysorbate 80 | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.25% | 0.25% |
| Hydroxypropyl-gamma-cyclodextrin | 1.50% | 1.50% | 2.00% | 2.00% | 2.00% | 2.00% | 2.00% |
| HPMC | 0.85% | 0.50% | — | — | — | — | — |
| CMC | — | — | 0.80% | 0.80% | 1.00% | 1.10% | 1.20% |
| Mannitol | 1.00% | 1.00% | 0.75% | 0.75% | 0.75% | 0.75% | 0.75% |
| PEG 400 | 0.50% | 0.50% | 0.75% | 0.75% | 0.75% | 0.75% | 0.75% |
| $MgCl_2$ | 0.10% | 0.10% | 0.10% | 0.10% | 0.10% | 0.10% | 0.10% |
| NaCl* | 0.45% | 0.45% | 0.35% | 0.35% | 0.35% | 0.35% | 0.35% |
| Citrate Buffer (mM) | 4.00 | 4.00 | 4.00 | 4.00 | 4.00 | 4.00 | 4.00 |
| pH | 6.5 | 6.5 | 7.0 | 7.0 | 7.0 | 7.0 | 7.0 |
| Menthol (mM) | 0.32 | 0.36 | 0.38 | 0.32 | 0.32 | 0.32 | 0.32 |
| Vitamin E (alpha-tocopherol) International units | 15 | 35 | 30 | — | — | — | — |
| Sorbate | 0.10% | 0.10% | 0.10% | 0.10% | 0.10% | 0.10% | 0.10% |

| (% w/v) | 145AZ | 145BA | 145BB | 145BC | 145BD |
|---|---|---|---|---|---|
| Polysorbate 80 | 1.00% | 1.00% | 1.00% | 1.00% | 1.00% |
| Poloxamer 407 | 1.00% | 1.00% | 1.00% | 1.00% | 1.00% |
| Poloxamer 188 | 0.20% | 0.20% | 0.20% | 0.20% | 0.20% |
| Polyoxyl Castor oil | 0.25% | 0.25% | 0.25% | 0.25% | 0.25% |
| Hydroxypropyl-gamma-cyclodextrin | 2.00% | 2.00% | 2.00% | 2.00% | 2.00% |
| CMC | 0.80% | 1.40% | 1.45% | 1.40% | 1.45% |
| Mannitol | 0.75% | 0.75% | 0.75% | 0.75% | 0.75% |
| PEG 400 | 0.75% | 0.75% | 0.75% | 0.75% | 0.75% |
| $MgCl_2$ | 0.10% | 0.10% | 0.10% | 0.10% | 0.10% |
| NaCl* | 0.35% | 0.35% | 0.35% | 0.35% | 0.35% |
| Citrate Buffer (mM) | 4.00 | 4.00 | 4.00 | 4.00 | 4.00 |
| pH | 7.0 | 7.0 | 7.0 | 7.0 | 7.0 |
| Menthol (mM) | 0.38 | 0.32 | 0.34 | 0.30 | 0.34 |
| Vitamin E (alpha-tocopherol) International units | 30 | — | — | — | — |
| Sorbate | 0.10% | 0.10% | 0.10% | 0.10% | 0.11% |

*NaCl may be at a concentration from 0.1% to 0.75%, preferably from 0.2% to 0.5%
"% HPMC equivalent" denotes an amount of CMC necessary to result in a final viscosity equivalent to the final viscosity achieved if the given % w/v of HPMC were used.

AQus™ Tears MGD may represent compositions of Table 7.

TABLE 7

AQus™ Tears MGD Compositions

| (% w/v) | 146 | 147 | 148 | 149 | 150 | 151 | 152 | 153 |
|---|---|---|---|---|---|---|---|---|
| Polysorbate 80 | 1.00% | 1.00% | 1.00% | 1.00% | 0.50% | 0.50% | 0.50% | 1.00% |
| Poloxamer 407 | 0.20% | 0.20% | 0.20% | 0.20% | — | — | — | 0.50% |
| Poloxamer 188 | 1.00% | 0.50% | 0.50% | 0.10% | 0.10% | 0.10% | 0.10% | 1.00% |
| Polyoxyl Castor oil | 0.01% | 0.50% | 0.01% | 1.00% | 0.25% | 0.25% | 0.25% | 0.50% |
| Hydroxypropyl-gamma-cyclodextrin | 1.50% | 1.50% | 1.50% | 1.50% | 3.00% | 3.00% | 3.50% | — |
| HPMC | 0.75% | 1.25% | 0.65% | — | 1.35% | — | 1.35% | 0.50% |
| CMC (% HPMC equivalent) | — | — | — | 1.25% | — | 1.25% | — | 0.25% |
| PEG 400 | 0.10% | 0.50% | 0.10% | — | — | — | — | 0.25% |
| Mannitol | 2.50% | 2.50% | 2.50% | 2.50% | 2.50% | 2.50% | 2.50% | 0.10% |
| $MgCl_2$ | 0.10% | 0.10% | 0.10% | 0.10% | 0.10% | 0.10% | 0.10% | 0.30% |
| NaCl | 0.40% | 0.40% | 0.50% | 0.30% | 0.40% | 0.40% | 0.40% | 4.00 |
| Phosphate Buffer (mM) | 3.00 | 3.00 | 3.00 | 3.00 | 3.00 | 3.00 | 3.00 | — |
| pH | 7.00 | 7.00 | 7.00 | 7.00 | 7.00 | 7.00 | 7.00 | 7.00 |
| Menthol (mM) | 0.15 | 0.17 | — | — | — | — | — | 0.06 |
| Sorbate | — | — | — | — | — | — | 0.10% | — |

| (% w/v) | 154 | 155 | 156 | 157 | 158 | 159 | 160 | 161 |
|---|---|---|---|---|---|---|---|---|
| Polysorbate 80 | 1.00% | 1.00% | 1.00% | 1.00% | 1.50% | 1.50% | 1.50% | 1.00% |
| Poloxamer 407 | 0.50% | 0.50% | 0.50% | 0.50% | 0.70% | 0.70% | 0.70% | 1.00% |
| Poloxamer 188 | 1.00% | 1.00% | 1.00% | 1.00% | 1.00% | 1.00% | 1.00% | 0.20% |

TABLE 7-continued

AQus ™ Tears MGD Compositions

| | | | | | | | | |
|---|---|---|---|---|---|---|---|---|
| Polyoxyl Castor oil | 0.50% | 0.50% | 0.50% | 0.50% | 0.01% | 0.01% | 0.01% | 0.15% |
| HPMC | 0.50% | 0.50% | 0.50% | 1.35% | 1.30% | 1.30% | 1.30% | 0.90% |
| PEG 400 | 0.25% | 0.25% | 0.25% | 0.25% | — | — | — | 0.50% |
| Mannitol | 0.25% | 0.25% | 0.25% | 1.75% | 2.50% | 2.50% | 2.50% | 1.00% |
| MgCl$_2$ | 0.10% | 0.10% | 0.10% | 0.05% | 0.10% | 0.10% | 0.10% | 0.10% |
| NaCl* | 0.30% | 0.30% | 0.30% | 0.25% | 0.35% | 0.35% | 0.35% | 0.35% |
| Citrate Buffer (mM) | 4.00 | 4.00 | 4.00 | 4.00 | — | — | — | — |
| Phosphate Buffer (mM) | — | — | — | — | 3.00 | 3.00 | 3.00 | 4.00 |
| pH | 7.00 | 7.00 | 7.00 | 7.00 | 5.5 | 5.5 | 5.5 | 6.5 |
| Menthol (mM) | 0.09 | 0.12 | 0.15 | 0.09 | — | 0.20 | 0.25 | 0.30 |
| Sorbate | — | — | — | 0.10% | 0.10% | 0.10% | 0.10% | 0.11% |

| (% w/v) | 162 | 163 | 164 | 165 | 166 | 167 |
|---|---|---|---|---|---|---|
| Polysorbate 80 | 1.00% | 1.00% | 1.00% | 1.00% | 1.00% | 1.00% |
| Poloxamer 407 | 1.00% | 1.00% | 1.00% | 1.00% | 1.00% | 1.00% |
| Poloxamer 188 | 0.20% | 0.20% | 0.20% | 0.20% | 0.20% | 0.20% |
| Polyoxyl Castor oil | 0.15% | 0.15% | 0.15% | 0.15% | 0.15% | 0.25% |
| HPMC | 0.90% | 0.90% | 1.00% | 1.00% | 1.00% | 1.20% |
| PEG 400 | 0.50% | 0.50% | 0.50% | 0.50% | 0.50% | 0.50% |
| Mannitol | 1.00% | 1.00% | 1.00% | 1.00% | 1.00% | 1.00% |
| MgCl$_2$ | 0.10% | 0.10% | 0.10% | 0.10% | 0.10% | 0.10% |
| NaCl* | 0.35% | 0.35% | 0.35% | 0.35% | 0.35% | 0.35% |
| Citrate Buffer (mM) | — | — | — | — | — | — |
| Phosphate Buffer (mM) | 3.00 | 3.00 | 4.00 | 4.00 | 3.00 | 4.00 |
| pH | 6.0 | 6.5 | 6.0 | 5.7 | 6.5 | 6.2 |
| Menthol (mM) | 0.25 | 0.25 | 0.25 | 0.25 | 0.25 | 0.27 |
| Sorbate | 0.10% | 0.10% | 0.10% | 0.10% | 0.10% | 0.10% |
| d-alpha tocopherol (IU) | — | — | — | — | — | 50 |

*NaCl may be at a concentration from 0.1% to 0.75%, preferably from 0.2% to 0.5%

"% HPMC equivalent" denotes an amount of CMC necessary to result in a final viscosity equivalent to the final viscosity achieved if the given % w/v of HPMC were used.

TABLE 8

Additional AQus ™ Tears Compositions

| (% w/v) | 168 | 169 | 170 | 171 | 172 | 173 | 174 | 175 |
|---|---|---|---|---|---|---|---|---|
| Polysorbate 80 | 1.00% | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.25% | 0.25% | 0.25% |
| Hydroxypropyl-gamma-cyclodextrin | 2.00% | 2.00% | 2.00% | 2.00% | 2.00% | 2.00% | 2.00% | 2.00% |
| CMC | 1.40% | 1.40% | 1.40% | 1.40% | 1.40% | 1.40% | 1.40% | 1.40% |
| PEG 400 | 0.75% | 0.75% | 0.75% | 0.75% | 0.75% | 0.75% | 0.75% | 0.75% |
| Mannitol | 0.75% | 0.75% | 0.75% | 0.75% | 0.75% | 0.75% | 0.75% | 0.75% |
| MgCl$_2$ | 0.10% | 0.10% | 0.10% | 0.10% | 0.10% | 0.10% | 0.10% | 0.10% |
| NaCl | 0.35% | 0.35% | 0.35% | 0.35% | 0.35% | 0.35% | 0.35% | 0.90% |
| Citrate Buffer (mM) | 4.00 | 4.00 | 4.00 | 4.00 | 4.00 | 4.00 | 4.00 | 4.00 |
| pH | 7.0 | 7.0 | 7.0 | 7.0 | 7.0 | 7.0 | 7.0 | 6.0 |
| Menthol (mM) | 0.32 | 0.34 | 0.36 | 0.38 | 0.40 | 0.42 | 0.44 | 0.36 |
| Sorbate | 0.10% | 0.10% | 0.10% | 0.10% | 0.10% | 0.10% | 0.10% | 0.10% |

| (% w/v) | 176 | 177 | 178 | 179 | 180 | 181 | 182 | 183 |
|---|---|---|---|---|---|---|---|---|
| Polysorbate 80 | 1.00% | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.25% | 0.25% | 0.25% |
| Hydroxypropyl-gamma-cyclodextrin | 2.00% | 2.00% | 2.00% | 2.00% | 2.00% | 2.00% | 2.00% | 2.00% |
| CMC | 1.40% | 1.40% | 1.40% | 1.40% | 1.40% | 1.40% | 1.40% | 1.40% |
| PEG 400 | 0.75% | 0.75% | 0.75% | 0.75% | 0.75% | 0.75% | 0.75% | 0.75% |
| Mannitol | 0.75% | 0.75% | 0.75% | 0.75% | 0.75% | 0.75% | 0.75% | 0.75% |
| MgCl$_2$ | 0.10% | 0.10% | 0.10% | 0.10% | 0.10% | 0.10% | 0.10% | 0.10% |
| NaCl | 1.25% | 1.50% | 1.75% | 1.50% | 1.75% | 2.00% | 2.00% | 2.00% |
| Citrate Buffer (mM) | 4.00 | 4.00 | 4.00 | 4.00 | 4.00 | 4.00 | 4.00 | 4.00 |
| pH | 6.0 | 6.0 | 6.0 | 6.0 | 6.0 | 6.0 | 5.5 | 5.5 |
| Menthol (mM) | 0.36 | 0.36 | 0.36 | 0.38 | 0.38 | 0.38 | 0.38 | 0.40 |
| Sorbate | 0.10% | 0.10% | 0.10% | 0.10% | 0.10% | 0.10% | 0.10% | 0.10% |

TABLE 8-continued

Additional AQus ™ Tears Compositions

| (% w/v) | 184 | 185 | 186 | 187 | 188 | 189 | 190 | 191 |
|---|---|---|---|---|---|---|---|---|
| Polysorbate 80 | 1.00% | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.25% | 0.25% | 0.25% |
| Hydroxypropyl-gamma-cyclodextrin | 2.00% | 2.00% | 2.00% | 2.00% | 2.00% | 2.00% | 2.00% | 2.00% |
| CMC | 1.40% | 1.40% | 1.40% | 1.40% | 1.40% | 1.40% | 1.40% | 1.40% |
| PEG 400 | 0.75% | 0.75% | 0.75% | 0.75% | 0.75% | 0.75% | 0.75% | 0.75% |
| Mannitol | 0.75% | 0.75% | 0.75% | 0.75% | 0.75% | 0.75% | 0.75% | 0.75% |
| $MgCl_2$ | 0.10% | 0.10% | 0.10% | 0.10% | 0.10% | 0.10% | 0.10% | 0.10% |
| NaCl | 0.35% | 0.35% | 0.35% | 1.25% | 1.50% | 2.00% | 0.35% | 1.50% |
| Citrate Buffer (mM) | 4.00 | 4.00 | 4.00 | 4.00 | 4.00 | 4.00 | 4.00 | 4.00 |
| pH | 7.0 | 7.0 | 7.0 | 6.0 | 6.0 | 5.5 | 7.0 | 6.0 |
| Menthol (mM) | 0.34 | 0.40 | 0.44 | 0.36 | 0.38 | 0.40 | 0.38 | 0.38 |
| Sorbate | 0.10% | 0.10% | 0.10% | 0.10% | 0.10% | 0.10% | 0.10% | 0.10% |
| Camphor (mM) | 0.1 | 0.1 | 0.1 | 0.1 | 0.1 | 0.1 | — | — |
| Alpha-linolenic acid | — | — | — | — | — | — | 0.1% | 0.1% |

| (% w/v) | 192 | 193 | 194 | 195 | 196 | 197 | 198 | 199 |
|---|---|---|---|---|---|---|---|---|
| Polysorbate 80 | 1.00% | 3.50% | 3.50% | 3.50% | 1.00% | 1.00% | 1.00% | 1.00% |
| Poloxamer 407 | 1.00% | — | — | — | — | 1.00% | 1.00% | 1.00% |
| Poloxamer 188 | 0.20% | — | — | — | — | 0.20% | 0.20% | 0.20% |
| Polyoxyl Castor oil | 0.25% | — | — | — | — | 0.25% | 0.25% | 0.25% |
| Hydroxypropyl-gamma-cyclodextrin | 2.00% | — | — | — | — | 2.00% | 2.00% | 2.00% |
| CMC | 1.40% | 1.40% | 1.40% | 1.40% | 1.40% | 1.40% | 1.40% | 1.40% |
| PEG 400 | 0.75% | 0.75% | 0.75% | 0.75% | 0.75% | 0.75% | 0.75% | 0.75% |
| Mannitol | 0.75% | 0.75% | 0.75% | 0.75% | 0.75% | 0.75% | 0.75% | 0.75% |
| $MgCl_2$ | 0.10% | 0.10% | 0.10% | 0.10% | 0.10% | 0.10% | 0.10% | 0.10% |
| NaCl | 0.90% | 0.90% | 0.90% | 0.90% | 0.90% | 0.90% | 0.90% | 0.90% |
| Citrate Buffer (mM) | 4.0 | 4.0 | 4.0 | 4.0 | 4.0 | 4.0 | 4.0 | 4.0 |
| pH | 6.00 | 6.00 | 6.00 | 6.00 | 6.00 | 6.00 | 6.00 | 6.00 |
| Menthol (mM) | 0.50 | 0.50 | 0.44 | 0.46 | 0.48 | 0.48 | 0.20 | 0.34 |
| Sorbate | 0.1% | 0.1% | 0.1% | 0.1% | 0.1% | 0.1% | 0.1% | 0.1% |

| (% w/v) | 200 | 201 | 202 | 203 | 204 | 205 | 206 | 207 |
|---|---|---|---|---|---|---|---|---|
| Polysorbate 80 | 3.50% | 3.50% | 3.50% | 3.50% | 3.50% | 3.50% | 3.50% | 3.50% |
| CMC | 1.40% | 1.40% | 1.40% | 1.40% | 1.40% | 1.40% | 1.40% | 1.40% |
| PEG 400 | 0.75% | 0.75% | 0.75% | 0.75% | 0.75% | 0.75% | 0.75% | 0.75% |
| Mannitol | 0.75% | 0.75% | 0.75% | 0.75% | 0.75% | 0.75% | 0.75% | 0.75% |
| $MgCl_2$ | 0.10% | 0.10% | 0.10% | 0.10% | 0.10% | 0.10% | 0.10% | 0.10% |
| NaCl | 0.90% | 0.90% | 0.90% | 0.90% | 0.90% | 0.90% | 0.90% | 0.90% |
| Citrate Buffer (mM) | 4.0 | 5.0 | 4.0 | 4.0 | 4.0 | 4.0 | 4.0 | 4.0 |
| pH | 6.0 | 5.0 | 6.0 | 6.0 | 6.0 | 6.0 | 6.0 | 6.0 |
| Menthol (mM) | 0.5 | — | 1.2 | 2.0 | 4.0 | 0.75 | 0.4 | 0.2 |
| Sorbate | 0.1% | 0.1% | 0.1% | 0.1% | 0.1% | 0.1% | 0.1% | 0.1% |

| (% w/v) | 208 | 209 | 210 | 211 | 212 | 213 | 214 | 215 |
|---|---|---|---|---|---|---|---|---|
| Polysorbate 80 | 3.50% | 3.50% | 3.50% | 3.50% | 3.50% | 3.50% | 3.50% | 3.50% |
| CMC | 1.40% | 1.40% | 1.40% | 1.40% | 1.40% | 1.40% | 1.40% | 1.40% |
| PEG 400 | 0.75% | 0.75% | 0.75% | 0.75% | 0.75% | 0.75% | 0.75% | 0.75% |
| Mannitol | 0.75% | 0.75% | 0.75% | 0.75% | 0.75% | 0.75% | 0.75% | 0.75% |
| $MgCl_2$ | 0.10% | 0.10% | 0.10% | 0.10% | 0.10% | 0.10% | 0.10% | 0.10% |
| NaCl | — | 0.90% | 1.75% | 1.25% | 1.50% | 1.75% | 2.00% | 1.75% |
| Citrate Buffer (mM) | 5.0 | 4.0 | 4.0 | 4.0 | 4.0 | 4.0 | 4.0 | 4.0 |
| pH | 5.0 | 6.0 | 6.0 | 6.0 | 6.0 | 6.0 | 6.0 | 6.0 |
| Menthol (mM) | — | 1.0 | 0.75 | 2.0 | 4.0 | 1.75 | 0.4 | 0.2 |
| Sorbate | 0.1% | 0.1% | 0.1% | 0.1% | 0.1% | 0.1% | 0.1% | 0.1% |

| (% w/v) | 216 | 217 | 218 | 219 | 220 | 221 | 222 | 223 |
|---|---|---|---|---|---|---|---|---|
| Polysorbate 80 | — | — | — | — | 4.00% | — | — | — |
| Poloxamer 407 | — | — | — | — | — | 2.00% | — | — |
| Poloxamer 188 | — | — | — | — | — | — | 2.00% | — |
| Polyoxyl Castor oil | — | — | — | — | — | — | — | 2.00% |
| CMC | 1.40% | 1.40% | 1.40% | 1.40% | 1.40% | 1.40% | 1.40% | 1.40% |
| Oleic Acid | — | 0.20% | 0.20% | 0.20% | 0.20% | 0.20% | 0.20% | 0.20% |
| PEG 400 | — | — | 2.00% | — | — | — | — | — |
| PEG 20000 | — | — | — | 2.00% | — | — | — | — |
| Mannitol | — | 2.00% | 2.00% | 2.00% | 2.00% | 2.00% | 2.00% | 2.00% |
| $MgCl_2$ | 0.10% | 0.10% | 0.10% | 0.10% | 0.10% | 0.10% | 0.10% | 0.10% |

TABLE 8-continued

Additional AQus ™ Tears Compositions

| | | | | | | | | |
|---|---|---|---|---|---|---|---|---|
| NaCl | 1.50% | 1.50% | 1.50% | 1.50% | 1.50% | 1.50% | 1.50% | 1.50% |
| Zinc Sulfate | — | 0.10% | 0.15% | 0.20% | 0.25% | 0.25% | 0.25% | 0.25% |
| Citrate Buffer (mM) | 5.0 | 5.0 | 5.0 | 5.0 | 5.0 | 5.0 | 5.0 | 5.0 |
| pH | 5.0 | 5.0 | 5.0 | 5.0 | 5.0 | 5.0 | 5.0 | 5.0 |
| BAK | 0.02% | 0.02% | 0.02% | 0.02% | 0.02% | 0.02% | 0.02% | 0.02% |
| Sorbate | 0.1% | 0.1% | 0.1% | 0.1% | 0.1% | 0.1% | 0.1% | 0.1% |

| (% w/v) | 224 | 225 | 226 | 227 | 228 | 229 | 230 | 231 |
|---|---|---|---|---|---|---|---|---|
| Polysorbate 80 | — | 1.00% | 1.00% | 1.00% | 3.50% | 3.50% | 3.50% | 3.50% |
| Poloxamer 407 | — | 1.00% | 1.00% | 1.00% | — | — | — | — |
| Poloxamer 188 | — | 1.00% | 1.00% | 1.00% | — | — | — | — |
| Polyoxyl Castor oil | — | 1.00% | 1.00% | 1.00% | — | — | — | — |
| Hydroxypropyl-gamma-cyclodextrin | 4.00% | 1.00% | 1.00% | 1.00% | — | — | — | — |
| CMC | 1.40% | 1.40% | 1.40% | 1.40% | 1.40% | 1.40% | 1.40% | 1.40% |
| Oleic Acid | 0.20% | 0.20% | 0.20% | 0.20% | — | — | — | — |
| PEG 400 | — | — | — | 2.00% | 0.75% | 0.75% | 0.75% | 0.75% |
| PEG 20000 | — | — | 2.00% | — | — | — | — | — |
| Mannitol | 2.00% | 2.00% | 2.00% | 2.00% | 0.75% | 0.75% | 0.75% | 0.75% |
| $MgCl_2$ | 0.10% | 0.10% | 0.10% | 0.10% | 0.10% | 0.10% | 0.10% | 0.10% |
| NaCl | 1.50% | 1.50% | 1.50% | 1.50% | 0.90% | 0.90% | 0.90% | 0.90% |
| Menthol (mM) | — | — | — | — | 0.5 | 0.55 | 0.6 | 0.65 |
| Zinc Sulfate | 0.25% | 0.25% | 0.25% | 0.25% | — | — | — | — |
| Citrate Buffer (mM) | 5.0 | 5.0 | 5.0 | 5.0 | 4.0 | 4.0 | 4.0 | 4.0 |
| pH | 5.0 | 5.0 | 5.0 | 5.0 | 6.0 | 6.0 | 6.0 | 6.0 |
| BAK | 0.02% | 0.02% | 0.02% | 0.02% | — | — | — | — |
| Sorbate | 0.1% | 0.1% | 0.1% | 0.1% | 0.1% | 0.1% | 0.1% | 0.1% |

| (% w/v) | 232 | 233 | 234 | 235 | 236 | 237 | 238 | 239 |
|---|---|---|---|---|---|---|---|---|
| Polysorbate 80 | 3.50% | 3.50% | 1.00% | 1.00% | 1.00% | 1.00% | 1.00% | 1.00% |
| Poloxamer 407 | — | — | 1.00% | 1.00% | 1.00% | 1.00% | 1.00% | 1.00% |
| Poloxamer 188 | — | — | 0.20% | 0.20% | 0.20% | 0.20% | 0.20% | 0.20% |
| Polyoxyl Castor oil | — | — | 0.25% | 0.25% | 0.25% | 0.25% | 0.25% | 0.25% |
| CMC | 1.40% | 1.40% | 1.40% | 1.40% | 1.40% | 1.40% | 1.40% | 1.40% |
| PEG 400 | 0.75% | 0.75% | 0.75% | 0.75% | 0.75% | 0.75% | 0.75% | 0.75% |
| Mannitol | 0.75% | 0.75% | 0.75% | 0.75% | 0.75% | 0.75% | 0.75% | 0.75% |
| $MgCl_2$ | 0.10% | 0.10% | 0.10% | 0.10% | 0.10% | 0.10% | 0.10% | 0.10% |
| NaCl | 0.90% | 0.90% | 0.90% | 0.90% | 0.90% | 0.90% | 0.90% | 0.90% |
| Menthol (mM) | 0.7 | 0.75 | 0.5 | 0.6 | 0.65 | 0.7 | 0.85 | 1.0 |
| Citrate Buffer (mM) | 4.0 | 4.0 | 4.0 | 4.0 | 4.0 | 4.0 | 4.0 | 4.0 |
| pH | 6.0 | 6.0 | 6.0 | 6.0 | 6.0 | 6.0 | 6.0 | 6.0 |
| Sorbate | 0.1% | 0.1% | 0.1% | 0.1% | 0.1% | 0.1% | 0.1% | 0.1% |

| (% w/v) | 240 | 241 | 242 | 243 | 244 | 245 | 246 | 247 |
|---|---|---|---|---|---|---|---|---|
| Polysorbate 80 | 3.50% | 3.50% | — | — | — | — | — | — |
| Poloxamer 407 | — | — | 3.00% | 3.00% | 3.00% | 3.00% | 3.00% | 3.00% |
| CMC | 1.40% | 1.40% | 1.40% | 1.40% | 1.40% | 1.40% | 1.40% | 1.45% |
| PEG 400 | 0.75% | 0.75% | 0.75% | 0.75% | 0.75% | 0.75% | 0.75% | 0.75% |
| Mannitol | 0.75% | 0.75% | — | — | — | — | — | 4.00% |
| $MgCl_2$ | 0.10% | 0.10% | 0.10% | 0.10% | 0.10% | 0.10% | 0.10% | 0.10% |
| NaCl | 0.90% | 1.25% | — | — | — | 0.25% | 0.25% | — |
| Citrate Buffer (mM) | 4.0 | 4.0 | 6.0 | 8.0 | 10.0 | 6.0 | 8.0 | 10.0 |
| pH | 6.0 | 6.0 | 5.0 | 5.0 | 5.0 | 5.0 | 5.0 | 5.0 |
| Menthol (mM) | 1.2 | — | — | — | — | — | — | — |
| Sorbate | 0.1% | 0.1% | 0.1% | 0.1% | 0.1% | 0.1% | 0.1% | 0.1% |

| (% w/v) | 248 | 249 | 250 | 251 | 252 | 253 | 254 | 255 |
|---|---|---|---|---|---|---|---|---|
| Poloxamer 407 | 3.00% | 3.00% | 3.00% | 3.00% | 3.00% | 3.00% | 3.00% | 3.00% |
| CMC | 1.45% | 1.45% | 1.40% | 1.45% | 1.45% | 1.45% | — | — |
| Carbopol ® 940 | — | — | — | — | — | — | 0.80% | 1.00% |
| PEG 400 | 0.75% | 0.75% | 0.75% | 0.75% | 0.75% | 0.75% | 0.75% | 0.75% |
| Mannitol | 4.00% | 4.00% | 4.00% | 4.00% | 4.00% | 4.00% | 4.00% | 4.00% |
| $MgCl_2$ | 0.10% | 0.10% | 0.10% | 0.10% | 0.10% | 0.10% | 0.10% | 0.10% |
| NaCl | — | 0.25% | — | 0.25% | — | 0.25% | 1.00% | 1.00% |
| Citrate Buffer (mM) | 8.0 | 8.0 | 8.0 | 8.0 | 8.0 | 8.0 | 8.0 | 8.0 |
| pH | 5.0 | 5.0 | 5.0 | 5.0 | 5.0 | 5.0 | 5.0 | 5.0 |
| Menthol (mM) | 0.4 | 0.4 | 0.4 | 0.4 | 0.8 | 0.8 | 0.8 | 0.4 |
| Sorbate | 0.1% | 0.1% | 0.1% | 0.1% | 0.1% | 0.1% | 0.1% | 0.1% |

| (% w/v) | 256 | 257 | 258 | 259 | 260 | 261 | 262 | 263 |
|---|---|---|---|---|---|---|---|---|
| Polysorbate 80 | — | — | 3.50% | 3.00% | — | 3.00% | — | — |
| Poloxamer 407 | 3.00% | 3.00% | — | — | 3.00% | — | 3.00% | 3.00% |

TABLE 8-continued

Additional AQus ™ Tears Compositions

| | | | | | | | |
|---|---|---|---|---|---|---|---|
| CMC | — | — | — | 1.40% | 1.40% | 1.45% | 1.45% | — |
| Carbopol ® 940 | 1.20% | 0.80% | — | — | — | — | — | 0.01% |
| PEG 400 | 0.75% | 0.75% | 0.75% | 0.75% | 0.75% | 0.75% | — | 0.01% |
| PEG 20000 | — | — | — | — | — | — | 0.75% | — |
| Mannitol | 4.00% | 4.00% | 0.75% | 1.50% | 1.50% | 2.50% | 2.50% | 0.04% |
| MgCl₂ | 0.10% | 0.10% | 0.10% | 0.10% | 0.10% | 0.10% | 0.10% | — |
| NaCl | 1.00% | 1.00% | 1.25% | 0.25% | 0.25% | 0.50% | 0.62% | 0.01% |
| Citrate Buffer (mM) | 8.0 | 8.0 | 4.0 | 7.0 | 7.50 | 5.50 | 5.00 | 5.00 |
| pH | 5.0 | 5.0 | 6.00 | 5.0 | 5.0 | 5.0 | 5.0 | 5.0 |
| Menthol (mM) | 0.8 | 1.5 | — | — | — | 1.2 | 1.5 | 1.0 |
| Sorbate | 0.1% | 0.1% | | 0.10% | 0.10% | 0.10% | 0.10% | 0.10% |

| (% w/v) | 264 | 265 | 266 | 267 | 268 | 269 | 270 | 271 |
|---|---|---|---|---|---|---|---|---|
| Polysorbate 80 | — | — | — | 3.00% | 3.00% | — | — | — |
| Poloxamer 407 | 3.00% | 3.50% | 3.00% | — | — | 3.00% | 3.00% | 3.00% |
| CMC | — | — | 1.40% | 1.40% | 1.45% | 1.45% | — | — |
| Carbopol ® 940 | 0.90% | 1.20% | — | — | — | — | 1.00% | 1.00% |
| PEG 400 | 0.01% | 0.01% | 0.75% | 0.75% | 0.75% | 0.75% | 0.75% | 0.75% |
| Mannitol | 0.03% | 0.02% | 1.50% | 1.50% | 4.00% | 4.00% | 4.00% | 2.50% |
| MgCl₂ | — | — | 0.10% | 0.10% | 0.10% | 0.10% | 0.10% | 0.10% |
| NaCl | 0.01% | 0.01% | — | — | 0.75% | 0.75% | 0.75% | 0.65% |
| Citrate Buffer (mM) | 5.50 | 5.50 | 6.0 | 6.0 | 8.0 | 8.0 | 8.0 | 7.0 |
| pH | 5.0 | 5.0 | 5.0 | 5.0 | 5.0 | 5.0 | 5.0 | 5.0 |
| Menthol (mM) | 1.2 | 1.0 | — | — | — | — | 1.0 | 1.0 |
| Sorbate | 0.1% | 0.1% | 0.1% | 0.1% | 0.1% | 0.1% | 0.1% | 0.1% |

| (% w/v) | 272 | 273 | 274 | 275 | 276 | 277 | 278 | 279 |
|---|---|---|---|---|---|---|---|---|
| Polysorbate 80 | — | 3.00% | — | 3.50% | — | — | — | — |
| Poloxamer 407 | 3.00% | — | 3.00% | — | 3.00% | 3.50% | 3.50% | 3.50% |
| Polyoxyl Castor oil | 0.15% | 0.15% | 0.25% | 0.25% | 0.25% | 0.25% | 0.25% | 0.25% |
| CMC | — | 1.40% | 1.40% | 1.45% | 1.45% | — | — | — |
| Carbopol ® 940 | 1.00% | — | — | — | — | 0.90% | 1.10% | 1.20% |
| PEG 400 | 0.75% | 0.75% | 0.75% | 0.75% | — | 0.75% | 0.75% | — |
| PEG 20000 | — | — | — | — | 0.75% | — | 0.75% | 0.75% |
| Mannitol | 2.00% | 1.50% | 1.50% | 2.50% | 2.50% | 4.00% | 3.00% | 2.00% |
| MgCl₂ | 0.10% | 0.10% | 0.10% | 0.10% | 0.10% | — | — | — |
| NaCl | 0.50% | 0.25% | 0.25% | 0.50% | 0.50% | 0.25% | 0.37% | 0.50% |
| EDTA | 0.1% | 0.1% | 0.1% | 0.1% | 0.1% | 0.1% | 0.1% | 0.1% |
| PVA | — | — | 0.50% | 0.50% | 0.50% | 0.50% | 0.50% | 0.50% |
| Citrate Buffer (mM) | 6.0 | 7.0 | 7.5 | 5.5 | 5.0 | 5.5 | 5.5 | 5.5 |
| pH | 5.0 | 5.0 | 5.0 | 5.0 | 5.0 | 5.0 | 5.0 | 5.0 |
| Menthol (mM) | 1.0 | — | — | 1.2 | 1.5 | 1.0 | 1.5 | 1.75 |
| Sorbate | 0.1% | 0.1% | 0.1% | 0.1% | 0.1% | 0.12% | 0.12% | 0.12% |

| (% w/v) | 280 | 281 | 282 | 283 | 284 | 285 | 286 | 287 |
|---|---|---|---|---|---|---|---|---|
| Polysorbate 80 | — | — | — | — | — | 1.00% | 1.00% | 1.00% |
| Poloxamer 407 | 0.25% | 3.50% | 3.50% | 3.50% | 0.25% | 1.00% | 1.00% | 1.00% |
| Poloxamer 188 | | | | | | 0.20% | 0.20% | 0.20% |
| Polyoxyl Castor oil | 0.25% | 0.25% | 0.25% | 0.25% | 0.25% | 0.25% | 0.25% | 0.25% |
| Sorbitol | 3.00% | — | — | — | 1.75% | — | — | — |
| CMC | — | — | — | — | — | — | — | 0.05% |
| Carbopol ® 940 | 1.20% | 0.90% | 1.00% | 1.20% | 1.20% | — | — | — |
| PEG 400 | — | 0.75% | 0.75% | | | 0.75% | 0.75% | — |
| PEG 60% | — | — | — | — | — | — | — | 0.75% |
| PEG 20000 | 0.75% | — | 0.75% | 0.75% | 0.75% | — | — | — |
| Mannitol | 2.00% | 1.00% | 1.00% | 1.00% | 1.00% | 0.75% | 0.75% | 0.75% |
| MgCl₂ | — | — | — | — | — | 0.10% | 0.10% | 0.10% |
| NaCl | 0.50% | 0.75% | 0.65% | 0.70% | 0.45% | 0.40% | 0.40% | 0.40% |
| EDTA | 0.1% | 0.1% | 0.1% | 0.1% | 0.1% | — | — | — |
| PVA | 0.50% | 0.10% | 0.10% | 0.10% | 0.10% | — | — | — |
| Citrate Buffer (mM) | 5.5 | 4.0 | 4.0 | 4.0 | 4.0 | 2.5 | 2.5 | 2.5 |
| pH | 5.0 | 5.5 | 6.0 | 6.0 | 6.0 | 6.5 | 6.5 | 6.5 |
| Menthol (mM) | 1.75 | 0.40 | 1.00 | 1.25 | 1.75 | — | — | — |
| Sorbate | 0.12% | 0.12% | 0.12% | 0.12% | 0.12% | 0.12% | 0.12% | 0.12% |

| (% w/v) | 288 | 289 | 290 | 291 | 292 | 293 | 294 | 295 |
|---|---|---|---|---|---|---|---|---|
| Polysorbate 80 | 1.00% | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.25% | 0.25% | 0.25% |
| Hydroxypropyl gamma cyclodextrin | — | — | — | 1.00% | 1.25% | 1.50% | 1.75% | 2.00% |
| CMC | 0.05% | 0.05% | 0.10% | 0.50% | 0.75% | 1.00% | 1.10% | 1.20% |

TABLE 8-continued

Additional AQus™ Tears Compositions

| | | | | | | | | |
|---|---|---|---|---|---|---|---|---|
| PEG 400 | — | 0.75% | 0.75% | 0.75% | 0.75% | 0.75% | — | — |
| PEG 6000 | — | — | — | — | — | — | 0.75% | — |
| PEG 20000 | 0.75% | 0.75% | — | — | — | — | — | 0.75% |
| Mannitol | 0.75% | 0.75% | 0.75% | 0.75% | 0.75% | 0.75% | 0.75% | 0.75% |
| MgCl$_2$ | 0.10% | 0.10% | 0.10% | 0.10% | 0.10% | 0.10% | 0.10% | 0.10% |
| NaCl | 0.40% | 0.40% | 0.60% | 0.70% | 0.75% | 0.65% | 0.85% | 0.85% |
| Citrate Buffer (mM) | 2.5 | 2.5 | 3.0 | 3.5 | 4.0 | 4.5 | 5.0 | 5.5 |
| pH | 6.5 | 6.5 | 6.0 | 6.0 | 6.0 | 6.0 | 6.0 | 6.0 |
| Menthol (mM) | — | — | 0.10 | 0.15 | 0.20 | 0.25 | 0.30 | 0.40 |
| Sorbate | 0.12% | 0.12% | 0.12% | 0.12% | 0.12% | 0.12% | 0.12% | 0.12% |

| (% w/v) | 296 | 297 | 298 | 299 | 300 | 301 | 302 | 303 |
|---|---|---|---|---|---|---|---|---|
| Polysorbate 80 | 1.00% | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% | 0.20% |
| Polyoxyl Castor oil | 0.25% | 0.25% | 0.25% | 0.25% | 0.25% | 0.25% | 0.25% | 0.25% |
| Hydroxypropyl gamma cyclodextrin | 0.60% | 0.75% | 0.75% | 0.65% | — | — | — | — |
| CMC | 1.30% | 1.40% | 1.50% | 1.60% | — | 0.1% | 1.2% | 1.2% |
| PEG 400 | 0.75% | 0.75% | 0.75% | 0.75% | — | — | — | — |
| PEG 6000 | — | 0.75% | — | — | — | 0.50% | 0.50% | 0.50% |
| PEG 20000 | 0.75% | 0.75% | 0.75% | 0.75% | 0.75% | — | — | — |
| Mannitol | 0.70% | 0.75% | 0.75% | 0.75% | 0.50% | 0.50% | 0.50% | 0.50% |
| MgCl$_2$ | 0.10% | 0.10% | 0.10% | 0.10% | 0.07% | 0.07% | 0.07% | 0.07% |
| NaCl | 0.60% | 0.85% | 0.85% | 0.85% | — | — | — | — |
| Citrate Buffer (mM) | 6.0 | 6.5 | 7.0 | 7.5 | 2.5 | 3.5 | 4.0 | 3.5 |
| pH | 6.0 | 5.5 | 5.5 | 5.0 | 6.5 | 6.0 | 6.0 | 5.5 |
| Menthol (mM) | 0.45 | 0.75 | 1.00 | 1.50 | — | 0.1 | 0.2 | 0.4 |
| Sorbate | — | — | — | — | — | — | — | — |

| (% w/v) | 304 |
|---|---|
| Polysorbate 80 | 1.00% |
| Poloxamer 407 | 1.00% |
| Poloxamer 188 | 0.20% |
| Polyoxyl Castor oil | 0.25% |
| Hydroxypropyl gamma cyclodextrin | — |
| CMC | 1.30% |
| PEG 400 | — |
| PEG 6000 | 0.50% |
| PEG 20000 | — |
| Mannitol | 0.50% |
| MgCl$_2$ | 0.07% |
| NaCl | — |
| Citrate Buffer (mM) | 4.0 |
| pH | 5.5 |
| Menthol (mM) | 0.6 |
| Sorbate | — |

In a preferred embodiment, artificial tear compositions of the present invention do not contain polyacrylates such as Pemulen® (Pemulen was a registered trademark of B.F. Goodrich Company for polymeric emulsifiers and is now owned by and available from Lubrizol Advanced Materials, Inc.). Pemulen® materials including acrylate/C10-30 alkyl acrylate cross-polymers, or high molecular weight co-polymers of acrylic acid and a long chain alkyl methacrylate cross-linked with allyl ethers of pentaerythritol.

In another embodiment, artificial tear compositions of the present invention do not contain boric acid, chlorobutanol, polyaminopropyl biguanide, or long chain fatty acids such as sesame oil (mixture of linoleic acid, oleic acid, palmitic acid, and stearic acid) or flaxseed oil (mixture of linoleic acid, oleic acid, palmitic acid, stearic acid and alpha-linoleic acid).

Drug Vehicles

In one embodiment, all artificial tear compositions of the present invention are capable of being used as drug vehicle compositions.

The present invention is further directed to a drug vehicle composition comprising:

an active agent, preferably selected from the group consisting of diquafosol, an antibiotic, a steroidal anti-inflammatory, a nonsteroidal anti-inflammatory, a glaucoma drug, a prostaglandin, a muscarinic receptor agonist, a miotic agent, acetylsalicylic acid ("ASA") and a combination thereof, more preferably the active agent is selected from the group consisting of diquafosol, bimatoprost, cyclosporine-A, GLC, prednisolone forte, ketorolac, gentamycin, polytrim, ciprofloxacin, moxifloxacin, gatifloxacin, lifitegrast, besifloxacin, pilocarpine, brimonidine, timolol, dexmedetomidine, timoptic, dorzolamide, latanoprost and a combination thereof;

about 2.0% w/v polysorbate 80;
about 1.0% w/v poloxamer 188;
about 1.0% w/v hydroxypropyl-gamma-cyclodextrin;
about 1.35% w/v HPMC;
about 2.5% w/v mannitol;

about 0.10% w/v magnesium chloride;
about 0.30% w/v sodium chloride; and
about 3 millimolar citrate buffer, and an optional preservative combination of one or more of:
about 0.005% to 0.02% BAK, 0.10% EDTA, and sorbate 0.10%.
wherein the composition has a pH of about 5.0. This latter combination of preservatives and antioxidants has demonstrated enhanced anterior chamber permeation, and duration to achieve greater clinical benefit in some cases.

The present invention is further directed to A drug vehicle gel composition comprising:
an active agent;
one or more nonionic surfactants selected from the group consisting of poloxamers, polysorbates, cyclodextrins, alkylaryl polyethers, polyoxyethyleneglycol alkyl ethers, tyloxapol, and polyoxyls at a total concentration from about 1.5% to about 5.9% w/v; from about 0.5% to about 5% w/v hydroxypropylmethyl cellulose (hypromellose) or an amount of a viscosity agent selected from the group consisting of cellulose derivatives, carbomers, gums, dextrans, polyvinyl alcohol, polyacrylic acids, povidone, polyethylene glycol, propylene glycol, chitosans, and hyaluronates and hyaluronic acids that yields a total viscosity of the composition equal to the total viscosity of the composition provided by from about 0.5% to about 5% w/v hydroxypropylmethyl cellulose;
about 2.5% w/v mannitol;
about 0.10% w/v magnesium chloride;
from about 0.20% to about 0.30% w/v sodium chloride;
about 3 millimolar citrate or phosphate buffer; and
optionally, from about 0.07 millimolar to about 0.2 millimolar menthol,
wherein the composition has a pH of at least 5.0.

The present invention is further directed to a drug vehicle composition comprising:
from about 0.05% to about 2.0% w/v cyclosporine-A, preferably, from about 0.05% to about 0.09% w/v;
from about 1% to about 5% w/v of Captisol®, β-cyclodextrin or a combination of Tween® β-cyclodextrin, preferably from about 3% to about 4% w/v;
optionally, about 0.25% w/v polyoxyl 40 castor oil;
optionally, about 0.1% to about 1% w/v of an alcohol, preferably from about 0.5% to about 1% w/v and preferably, the alcohol is selected from the group consisting of a polyvinyl alcohol, glycofurol, octoxynol 40 and a combination thereof;
optionally, from about 0.5% to about 1.25% hydroxypropylmethyl cellulose or a concentration of carboxymethyl cellulose that yields a total viscosity of the composition equal to the total viscosity of the composition provided by from about 0.5% to about 1.25% w/v hydroxypropylmethyl cellulose;
optionally, from about 0.1% to about 0.9% w/v sodium chloride, preferably, about 0.3% w/v;
optionally, from about 0.5% to about 2.5% w/v mannitol;
optionally, about 0.1% magnesium chloride,
optionally, about 3 millimolar phosphate buffer or about 4 millimolar citrate buffer;
optionally, about 0.1% w/v sorbate; and
optionally, about 0.1 millimolar menthol,
wherein optionally, the composition has a pH of about 7.0.

The present invention is further directed to a drug vehicle composition comprising:
about 0.09% w/v cyclosporine-A;
about 3.0% to about 4.0% w/v poloxamer 407,
about 0.25% w/v sodium chloride;
about 0.2% or about 0.75% w/v hydroxypropylmethyl cellulose;
about 3 millimolar phosphate buffer or about 4 millimolar citrate buffer;
optionally, about 1.0% w/v polysorbate 80;
optionally, about 0.01% w/v polyoxyl castor oil;
optionally, about 0.1% w/v sorbate;
optionally, about 0.1 millimolar menthol,
wherein the composition has a pH of about 7.0.

The present invention is further directed to a drug vehicle composition comprising:
from about 0.01% to about 2.0% w/v cyclosporine-A, preferably from about 0.05% to about 0.09% w/v, more preferably about 0.05%, about 0.075% or about 0.09% w/v;
from about 1.0% to about 5.0% w/v polysorbate 80, preferably from about 1.0% to about 4.0% w/v, more preferably from about 1.0% to about 1.5% w/v;
from about 0.1% to about 2.0% w/v poloxamer 407, preferably from about 0.5% to about 0.7% w/v, more preferably about 0.5% or about 0.7% w/v;
from about 0.1% to about 2.0% w/v poloxamer 188, preferably from about 0.5% to about 1.5% w/v, more preferably about 1.0% w/v;
from about 0.001% to about 1.0% w/v polyoxyl castor oil, preferably from about 0.005% to about 0.01% w/v, even more preferably about 0.01% w/v;
from about 0.5% to about 4.0% w/v mannitol, preferably from about 0.5% to about 3.0% w/v, more preferably from about 0.5% to about 2.5% w/v;
from about 0.05% to about 0.1% w/v magnesium chloride, more preferably about 0.05% w/v;
from about 0.1% to about 2.0% w/v hydroxypropylmethyl cellulose, preferably from about 0.5% to about 1.35% w/v;
from about 0.1% to about 0.5% w/v polyethylene glycol 400 ("PEG-400"), preferably about 0.25% w/v;
from about 0.0% to about 0.9% w/v sodium chloride, preferably from about 0.1% to about 0.40% w/v;
about 3 millimolar phosphate buffer or about 4 millimolar citrate buffer;
from about 0.05% to about 2% w/v sorbate, preferably about 0.10% w/v, optionally, from about 0.07 to about 0.3 millimolar menthol; and
optionally, a preservative combination of one or more of: about 0.005% to 0.02% BAK and 0.10% EDTA
wherein the composition has a pH of about 7.0.

The present invention is further directed to a drug vehicle composition comprising:
optionally, from about 3.0% to about 3.5% w/v diquafosol, preferably about 3.0% or about 3.37% w/v;
from about 2.0% to about 6.0% w/v of one or more nonionic surfactants, preferably the one or more nonionic surfactants is selected from the group consisting of polysorbates, poloxamers, polyoxyl castor oils, and cyclodextrins, more preferably selected from the group consisting of polysorbate 80, poloxamer 407, poloxamer 188, polyoxyl castor oil and hydroxypropyl gamma cyclodextrin;
from about 0.5% to about 0.75% w/v of a polyethylene glycol having a molecular weight from about 400 to about 20,000 Daltons;
from about 0.75% to about 3.0% w/v mannitol;
about 0.1% w/v magnesium chloride;
from about 1.1% to about 1.45% w/v carboxymethyl cellulose;

from about 0.4% to about 1.25% w/v sodium chloride;
about 3 millimolar phosphate buffer or from about 4 to about 5 millimolar citrate buffer; from about 0.1% to about 0.12% w/v sorbate;
optionally, from about 0.1 to about 5.0 millimolar menthol, preferably from about 0.2 to about 2.5 millimolar, more preferably from about 0.2 to about 1.6 millimolar and most preferably from about 0.1 to about 0.45 millimolar; and
optionally, about 2.0% w/v hydroxy-propyl-gamma-cyclodextrin,
wherein the composition has a pH from about 5.5 to about 7.0.

The present invention is further directed to a drug vehicle composition comprising:
about 3.0% w/v diquafosol;
about 3.00% w/v polysorbate 80;
about 0.75% w/v polyethylene glycol 400;
about 1.50% w/v mannitol;
about 0.1% w/v magnesium chloride;
about 1.40% w/v carboxymethyl cellulose;
about 0.90% w/v sodium chloride;
about 0.5 millimolar menthol;
about 4 millimolar citrate buffer;
about 1.0% w/v sorbate; and
about 2.0% w/v hydroxy-propyl-gamma cyclodextrin.

The present invention is further directed to a drug vehicle composition comprising:
optionally, from about 1.0% to about 1.5% w/v trehalose;
from about 2.0% to about 6.0% w/v of one or more nonionic surfactants, preferably the one or more nonionic surfactants is selected from the group consisting of polysorbates, poloxamers, polyoxyl castor oils, and cyclodextrins, more preferably selected from the group consisting of polysorbate 80, poloxamer 407, poloxamer 188, polyoxyl castor oil and hydroxypropyl gamma cyclodextrin, preferably comprising about 1.00% w/v polysorbate 80, about 1.00% w/v poloxamer 407, about 0.20% w/v poloxamer 188 and about 0.25% w/v polyoxyl castor oil;
from about 0.50% to about 1.50% w/v of a polyethylene glycol having a molecular weight of from about 400 to about 20,000 Daltons;
from about 0.50% to about 0.75% w/v mannitol;
from about 0.07% to about 0.10% w/v magnesium chloride;
from about 2.5 to about 6.0 millimolar citrate buffer;
optionally, from about 0.1% to about 1.30% w/v carboxymethyl cellulose;
optionally, from about 0.4% to about 0.65% w/v sodium chloride;
optionally, from about 0.1 to about 0.45 millimolar menthol;
optionally, about 0.12% w/v sorbate,
wherein the composition has a pH from about 5.5 to about 6.5.

TABLE 9

Cyclosporine-A Drug Vehicles

| Formula | #C1 | #C2 | #C3 | #C4 | #C5 | #C6 | #C7 | #C8 | #C9 | #C10 | #C11 | #C12 |
|---|---|---|---|---|---|---|---|---|---|---|---|---|
| Cyclosporine-A | 0.05% | 0.05% | 0.05% | 0.05% | 0.075% | 0.075% | 0.075% | 0.075% | 0.09% | 0.09% | 0.09% | 0.09% |
| Polysorbate 80 | 1.0% | 1.5% | 1.5% | 1.5% | 1.0% | 1.5% | 1.5% | 1.5% | 1.0% | 1.5% | 1.5% | 1.5% |
| Poloxamer 407 | 0.5% | 0.5% | 0.7% | 0.7% | 0.5% | 0.5% | 0.7% | 0.7% | 0.5% | 0.5% | 0.7% | 0.7% |
| Poloxamer 188 | 1% | 1% | 1% | 1% | 1% | 1% | 1% | 1% | 1% | 1% | 1% | 1% |
| Polyoxyl Castor Oil | 0.01% | 0.01% | 0.01% | 0.01% | 0.01% | 0.01% | 0.01% | 0.01% | 0.01% | 0.01% | 0.01% | 0.01% |
| HPMC | 1.35% | 1.35% | 1.35% | 1.35% | 1.35% | 1.35% | 1.35% | 1.35% | 1.35% | 1.35% | 1.35% | 1.35% |
| PEG-400 | 0.25% | 0.25% | 0.25% | 0.25% | 0.25% | 0.25% | 0.25% | 0.25% | 0.25% | 0.25% | 0.25% | 0.25% |
| Mannitol | 1.75% | 1.25% | 2.5% | 0.5% | 1.75% | 1.25% | 1.5% | 0.5% | 1.75% | 1.25% | 1.5% | 0.5% |
| MgCl$_2$ | 0.05% | 0.05% | 0.05% | 0.05% | 0.05% | 0.05% | 0.05% | 0.05% | 0.05% | 0.05% | 0.05% | 0.05% |
| NaCl | 0.25% | 0.35% | 0.25% | 0.1% | 0.25% | 0.35% | 0.4% | 0.1% | 0.25% | 0.35% | 0.4% | 0.1% |
| Citrate Buffer | 4 mM | 4 mM | 4 mM | 4 mM | 4 mM | 4 mM | 4 mM | 4 mM | 4 mM | 4 mM | 4 mM | 4 mM |
| Sorbate | 0.1% | 0.1% | 0.1% | 0.1% | 0.1% | 0.1% | 0.1% | 0.1% | 0.1% | 0.1% | 0.1% | 0.1% |
| pH | 7.0 | 7.0 | 7.0 | 7.0 | 7.0 | 7.0 | 7.0 | 7.0 | 7.0 | 7.0 | 7.0 | 7.0 |

| Formula | #C13 | #C14 | #C15 | #C16 | #C17 | #C18 | #C19 | #C20 | #C21 |
|---|---|---|---|---|---|---|---|---|---|
| Cyclosporine-A | 0.09% | 0.05% | 0.05% | 0.09% | 0.09% | 0.05% | 0.05% | 0.05% | 0.05% |
| Polysorbate 80 | 1.5% | 1.5% | 1.5% | 1.5% | 1.5% | 1.5% | 1.5% | 1.75% | 1.75% |
| Poloxamer 407 | 0.7% | 0.7% | 0.7% | 0.7% | 0.7% | — | — | — | 0.7% |
| Poloxamer 188 | 1% | 1% | 1% | 1% | 1% | — | — | 0.7% | 1.0% |
| Polyoxyl Castor Oil | 0.01% | 0.01% | 0.01% | 0.01% | 0.01% | 0.01% | 1.25% | 1.25% | 1.25% |
| HPMC | 1.35% | 1.35% | 1.35% | 1.35% | 1.35% | 1.3% | 1.3% | 1.3% | 1.3% |
| Mannitol | 2.5% | 2.5% | 2.5% | 1.75% | 1.75% | — | — | — | — |
| MgCl$_2$ | 0.1% | 0.1% | 0.1% | 0.05% | 0.05% | — | — | — | — |
| NaCl | 0.25% | 0.25% | 0.25% | 0.25% | 0.25% | 0.9% | 0.75% | 0.9% | 0.9% |
| Phosphate Buffer | 3 mM | 3 mM | 3 mM | — | — | 3 mM | 3 mM | 3 mM | 3 mM |
| Sorbate | — | — | 0.1% | — | 0.1% | — | — | — | — |
| Glycerin | — | — | — | — | — | 2.0% | 2.0% | 2.0% | 2.0% |
| pH | 7.0 | 7.0 | 7.0 | 7.0 | 7.0 | 6.5 | 6.5 | 6.5 | 6.5 |

TABLE 10

Diquafosol Drug Vehicles

| Formula | D1 | D2 | D3 | D4 | D5 | D6 | D7 | D8 |
|---|---|---|---|---|---|---|---|---|
| Diquafosol | — | 3.00% | — | 3.00% | — | 3.00% | — | — |
| Polysorbate 80 | 1.00% | 1.00% | 1.00% | 1.00% | 1.00% | 1.00% | 3.00% | 3.50% |
| Poloxamer 407 | 1.00% | 1.00% | 1.00% | 1.00% | 1.00% | 1.00% | — | — |
| Poloxamer 188 | 0.20% | 0.20% | 0.20% | 0.20% | 0.20% | 0.20% | — | — |
| Polyoxyl Castor Oil | 0.25% | 0.25% | 0.25% | 0.25% | 0.25% | 0.25% | — | — |
| Hydroxypropyl gamma cyclodextrin | 2.00% | 2.00% | — | — | 1.50% | 1.50% | 2.00% | 2.00% |
| PEG-400 | 0.75% | 0.75% | 0.75% | 0.75% | 0.50% | 0.50% | 0.75% | 0.75% |
| Mannitol | 0.75% | 0.75% | 0.75% | 0.75% | 0.75% | 0.75% | 1.50% | 3.00% |
| $MgCl_2$ | 0.10% | 0.10% | 0.10% | 0.10% | 0.10% | 0.10% | 0.10% | 0.10% |
| CMC | 1.40% | 1.40% | 1.40% | 1.40% | 1.10% | 1.10% | 1.40% | 1.45% |
| NaCl | 0.90% | 0.90% | 0.90% | 0.90% | 0.40% | 0.40% | 0.90% | 1.25% |
| Menthol (mM) | 0.36 | 0.36 | 0.36 | 0.36 | — | — | 0.5 | 1.0 |
| Vehicle | Diquas | Diquas | Diquas | Diquas | Diquas | Diquas | Diquas | Diquas |
| Citrate Buffer (mM) | 4.0 | 4.0 | 4.0 | 4.0 | — | — | 4.0 | 5.0 |
| Phosphate Buffer (mM) | — | — | — | — | 3.0 | 3.0 | — | — |
| Sorbate | 0.1% | 0.1% | 0.1% | 0.1% | 0.1% | 0.1% | 0.1% | 0.1% |
| pH | 6.00 | 6.00 | 6.00 | 6.00 | 7.00 | 7.00 | 5.5 | 5.5 |

| Formula | D9 | D10 | D11 | D12 | D13 | D14 | D15 | D16 |
|---|---|---|---|---|---|---|---|---|
| Diquafosol | 3.00% | 3.00% | — | 3.00% | — | 3.37% | — | 3.37% |
| Polysorbate 80 | 3.00% | 3.50% | 1.00% | 1.00% | — | — | — | — |
| Poloxamer 407 | — | — | 1.00% | 1.00% | 3.50% | 3.50% | 3.50% | 3.50% |
| Poloxamer 188 | — | — | 0.20% | 0.20% | — | — | — | — |
| Polyoxyl Castor Oil | — | — | 0.25% | 0.25% | 0.25% | 0.25% | 0.25% | 0.25% |
| Hydroxypropyl gamma cyclodextrin | 2.00% | 2.00% | — | — | — | — | — | — |
| PEG-400 | 0.75% | 0.75% | 0.50% | 0.50% | — | — | — | — |
| PEG-6000 | — | — | — | — | 0.75% | 0.75% | — | — |
| PEG-20000 | — | — | — | — | — | — | 0.75% | 0.75% |
| Mannitol | 1.50% | 3.00% | 0.75% | 0.75% | 0.75% | 0.75% | 0.75% | 0.75% |
| $MgCl_2$ | 0.10% | 0.10% | 0.10% | 0.10% | 0.10% | 0.10% | 0.10% | 0.10% |
| CMC | 1.40% | 1.45% | 1.10% | 1.10% | 1.25% | 1.25% | 1.40% | 1.40% |
| NaCl | 0.90% | 1.25% | 0.90% | 0.90% | 0.90% | 0.80% | 0.90% | 0.80% |
| Menthol (mM) | 0.5 | 1.0 | 0.60 | 0.60 | — | 0.8 | — | 0.8 |
| Vehicle | Diquas | Diquas | Diquas | Diquas | Diquas | Diquas | Diquas | Diquas |
| Citrate Buffer (mM) | 4.0 | 5.0 | 4.0 | 4.0 | 4.0 | 4.0 | 4.5 | 4.5 |
| Phosphate Buffer (mM) | — | — | — | — | — | — | — | — |
| Sorbate | 0.1% | 0.1% | 0.1% | 0.1% | 0.12% | 0.12% | 0.12% | 0.12% |
| pH | 5.5 | 5.5 | 7.0 | 7.0 | 6.0 | 6.0 | 6.0 | 5.5 |

| Formula | D10 |
|---|---|
| Diquafosol | 3.00% |
| Polysorbate 80 | 3.50% |
| Poloxamer 407 | — |
| Poloxamer 188 | — |
| Polyoxyl Castor Oil | — |
| Hydroxypropyl gamma Cyclodextrin | — |
| PEG-400 | 0.75% |
| PEG-6000 | — |
| PEG-20000 | — |
| Mannitol | 0.75% |
| $MgCl_2$ | 0.10% |
| CMC | 1.40% |
| NaCl | — |
| Menthol (mM) | — |
| Vehicle | Diquas |
| Citrate Buffer (mM) | 5.0 |
| Phosphate Buffer (mM) | — |
| Sorbate | 0.1% |
| pH | 5.0 |

TABLE 11

Trehalose Drug Vehicles

| Formula | T1 | T2 | T3 | T4 | T5 | T6 | T7 | T8 |
|---|---|---|---|---|---|---|---|---|
| Trehalose | 1.50% | 1.50% | 1.50% | 1.00% | — | — | — | — |
| Polysorbate 80 | 1.00% | 1.00% | 1.00% | 1.00% | 1.00% | 1.00% | 1.00% | 1.00% |
| Poloxamer 407 | 1.00% | 1.00% | 1.00% | 1.00% | 1.00% | 1.00% | 1.00% | 1.00% |
| Poloxamer 188 | 0.20% | 0.20% | 0.20% | 0.20% | 0.20% | 0.20% | 0.20% | 0.20% |
| Polyoxyl Castor Oil | 0.25% | 0.25% | 0.25% | 0.25% | 0.25% | 0.25% | 0.25% | 0.25% |
| Hydroxypropyl gamma cyclodextrin | — | — | 1.50% | 0.60% | — | — | — | — |
| PEG-400 | 0.75% | 0.75% | 0.75% | 0.75% | — | — | — | — |
| PEG-6000 | — | — | — | — | 0.75% | 0.50% | — | 0.50% |
| PEG-20000 | — | — | — | 0.75% | 0.75% | — | 0.75% | — |
| Mannitol | 0.75% | 0.75% | 0.75% | 0.70% | 0.50% | 0.50% | 0.50% | 0.50% |
| MgCl$_2$ | 0.10% | 0.10% | 0.10% | 0.10% | 0.07% | 0.07% | 0.07% | 0.07% |
| CMC | — | 0.10% | 1.00% | 1.30% | — | 0.10% | — | 1.20% |
| NaCl | 0.40% | 0.60% | 0.65% | 0.60% | — | — | — | — |
| Menthol (mM) | — | 0.10 | 0.25 | 0.45 | — | 0.10 | — | 0.20 |
| Citrate Buffer (mM) | 2.5 | 3.0 | 4.5 | 6.0 | 2.5 | 3.5 | 2.5 | 4.00 |
| Sorbate | 0.12% | 0.12% | 0.12% | — | — | — | — | — |
| pH | 6.5 | 6.0 | 6.0 | 6.0 | 6.5 | 6.5 | 6.5 | 6.0 |

| Formula | T9 | T10 |
|---|---|---|
| Trehalose | — | — |
| Polysorbate 80 | 1.00% | 1.00% |
| Poloxamer 407 | 1.00% | 1.00% |
| Poloxamer 188 | 0.20% | 0.20% |
| Polyoxyl Castor Oil | 0.25% | 0.25% |
| Hydroxypropyl gamma cyclodextrin | — | — |
| PEG-400 | — | — |
| PEG-6000 | 0.50% | 0.50% |
| PEG-20000 | — | — |
| Mannitol | 0.50% | 0.50% |
| MgCl$_2$ | 0.10% | 0.10% |
| CMC | 1.20% | 1.30% |
| NaCl | — | — |
| Menthol (mM) | 0.4 | 0.6 |
| Citrate Buffer (mM) | 3.5 | 4.0 |
| Sorbate | — | — |
| pH | 5.5 | 5.5 |

The present invention is further directed to a drug vehicle composition comprising:
from about 0.05% to about 0.09% w/v cyclosporine-A, preferably 0.05%, 0.075% or 0.09% w/v;
from about 1.0% to about 3.5% w/v polysorbate 80, preferably 1.5% or 3.5% w/v;
from about 0.5% to about 0.7% w/v poloxamer 407, preferably about 0.7% w/v;
about 1.0% w/v poloxamer 188;
from about 0.01% to about 0.75% polyoxyl castor oil, preferably about 0.01% w/v polyoxyl castor oil;
from about 1.75% to about 2.5% w/v mannitol;
from about 0.05% to about 0.1% w/v magnesium chloride;
from about 0.5% to about 1.35% w/v hydroxypropylmethyl cellulose, preferably from about 1.25% to about 1.35% w/v, more preferably about 0.5%, 0.75%, 0.85%, 1.0%, 1.25% or 1.35% w/v;
about 0.25% w/v sodium chloride;
about 3 millimolar phosphate buffer or about 4 millimolar citrate buffer;
optionally, from about 0.02 to about 0.09 millimolar menthol, preferably about 0.02, 0.04, 0.06 or 0.09; and
optionally, a preservative combination of one or more of: about 0.005% to 0.02% BAK, 0.10% EDTA, and sorbate 0.10%,
wherein the composition has a pH of about 7.0.

The present invention is further directed to a drug vehicle composition comprising:
from about 0.1 to about 1% w/v ketorolac tromethamine, preferably 0.5% w/v;
from about 1.0 to about 3.5% w/v polysorbate 80, preferably 1.5% or 3.5% w/v;
from about 0.5% to about 0.7% w/v poloxamer 407, preferably about 0.7% w/v;
about 1.0% w/v poloxamer 188;
from about 0.01% to about 0.75% polyoxyl castor oil, preferably about 0.01% w/v polyoxyl castor oil;
from about 1.75% to about 2.5% w/v mannitol;
from about 0.05% to about 0.1% w/v magnesium chloride;
from about 0.5% to about 1.35% w/v hydroxypropylmethyl cellulose, preferably from about 1.25% to about 1.35% w/v, more preferably about 0.5%, 0.75%, 0.85%, 1.0%, 1.25% or 1.35% w/v;
about 0.25% w/v sodium chloride;
about 3 millimolar phosphate buffer or about 4 millimolar citrate buffer;
optionally, from about 0.02 to about 0.09 millimolar menthol, preferably about 0.02, 0.04, 0.06 or 0.09; and
optionally, a preservative combination of one or more of: about 0.005% to 0.02% BAK, 0.10% EDTA, and sorbate 0.10%,
wherein the composition has a pH of about 7.0.

The present invention is further directed to a drug vehicle composition comprising:
- about 0.09% w/v cyclosporine-A;
- about 3.5% w/v polysorbate 80;
- about 0.25% w/v sodium chloride;
- optionally, about 0.7% w/v poloxamer 407;
- optionally, about 1.0% w/v poloxamer 188;
- optionally, about 2.5% w/v mannitol;
- optionally, about 0.5% w/v hydroxypropylmethyl cellulose;
- about 3 millimolar phosphate buffer or about 4 millimolar citrate buffer;
- optionally, about 0.07 millimolar menthol; and
- optionally, a preservative combination of one or more of: about 0.005% to 0.02% BAK, 0.10% EDTA, and sorbate 0.10%, wherein the composition has a pH of about 7.0.

In a preferred embodiment, the ratio of cyclosporine A to polyoxyl castor oil is greater than 0.08:1, more preferably from about 10:1 to about 9:1, even more preferably from about 5:1 to about 9:1.

The present invention is further directed to a drug vehicle composition comprising:
- about 0.06% w/v dexmedetomidine;
- about 3.5% w/v polysorbate 80;
- about 0.7% w/v poloxamer 407;
- about 1.0% w/v poloxamer 188;
- about 0.01% w/v polyoxyl castor oil;
- about 2.5% w/v mannitol;
- about 0.1% w/v magnesium chloride;
- about 1.25% w/v hydroxypropylmethyl cellulose;
- about 0.25% w/v sodium chloride; and
- about 3 millimolar phosphate buffer, wherein the composition has a pH of about 7.0.

The present invention is further directed to a drug vehicle composition comprising:
- an effective amount of lifitegrast;
- about 3.5% w/v polysorbate 80;
- about 0.7% w/v poloxamer 407;
- about 1.0% w/v poloxamer 188;
- about 0.01% w/v polyoxyl castor oil;
- from about 0.65% to about 1.25% w/v hydroxypropylmethyl cellulose, preferably 0.65%, 0.85%, 1.0% or 1.25% w/v;
- about 2.5% w/v mannitol;
- about 0.1% w/v magnesium chloride; and
- about 3 mM phosphate buffer;

wherein the composition has a pH of about 7.0.

The present invention is further directed to a drug vehicle composition comprising:
- about 0.09% w/v cyclosporine-A;
- about 4% w/v polysorbate 80; and
- about 0.01% w/v polyoxyl castor oil.

The present invention is further directed to a drug vehicle composition comprising:
- about 0.09% w/v cyclosporine-A;
- about 3.5% w/v polysorbate 80;
- about 4.0% w/v poloxamer 407; and
- about 0.01% w/v polyoxyl castor oil.

The present invention is further directed to a drug vehicle composition comprising:
- about 0.09% w/v cyclosporine-A; and
- about 0.5% glycofurol.

The present invention is further directed to a drug vehicle composition comprising:
- about 1.0% w/v ASA;
- about 3.5% w/v polysorbate 80;
- about 0.7% w/v poloxamer 407;
- about 1.0% w/v poloxamer 188;
- about 0.01% w/v polyoxyl castor oil;
- about 2.5% w/v mannitol;
- about 0.25% w/v sodium chloride;
- about 0.1% w/v magnesium chloride;
- about 1.25% w/v hydroxypropylmethyl cellulose;
- about 3 millimolar phosphate buffer or about 4 millimolar citrate buffer;
- about 1.0% w/v polyethylene glycol 400; and
- about 0.12% w/v sorbate, wherein the composition has a pH of about 7.0 and wherein optionally, the composition is for MGD or allergies.

The present invention is further directed to a drug vehicle composition comprising:
- about 5.0% w/v ASA;
- about 3.5% w/v polysorbate 80;
- about 0.7% w/v poloxamer 407;
- about 1.0% w/v poloxamer 188;
- about 0.01% w/v polyoxyl castor oil;
- about 2.5% w/v mannitol;
- about 0.25% w/v sodium chloride;
- about 0.1% w/v magnesium chloride;
- about 1.25% w/v hydroxypropylmethyl cellulose;
- about 3 millimolar phosphate buffer or about 4 millimolar citrate buffer;
- about 1.0% w/v polyethylene glycol 400; and
- about 0.12% w/v sorbate, wherein the composition has a pH of about 7.0 and wherein optionally, the composition is for acne.

The present invention is further directed to a drug vehicle composition comprising from about 5.0% to about 10% w/v ASA in a composition of the present invention and optionally, from about 1% to about 10% w/v benzoyl peroxide or octynol including octynol 11 or 309.

The present invention is further directed to a drug vehicle gel composition comprising:
- an active agent, preferably selected from the group consisting of diquafosol, an antibiotic, a steroid anti-inflammatory, a nonsteroidal anti-inflammatory, a glaucoma drug, a prostaglandin, a muscarinic receptor agonist, a miotic agent, an antihistamine, acetylsalicylic acid and a combination thereof, more preferably the active agent is selected from the group consisting of diquafosol, KPI-121, lacritin, PRO-87, a C-terminal 25 amino acid fragment of lacritin, tivanisiran, omega 3 fatty acids, bimatoprost, cyclosporine-A, GLC, prednisolone forte, ketorolac, gentamycin, polytrim, ciprofloxacin, moxifloxacin, gatifloxacin, lifitegrast, besifloxacin, pilocarpine, brimonidine, timolol, dexmedetomidine, timoptic, dorzolamide, latanoprost and a combination thereof;
- one or more nonionic surfactants selected from the group consisting of poloxamers, polysorbates, cyclodextrins, alkylaryl polyethers, polyoxyethyleneglycol alkyl ethers, tyloxapol, and polyoxyls at a total concentration from about 1.5% to about 5.9% w/v, preferably about 2.0% w/v polysorbate 80, about 1.0% w/v poloxamer 188 and about 1.0% w/v hydroxypropyl-gamma-cyclodextrin;
- from about 0.5% to about 20% w/v HPMC, preferably from about 0.5% to about 10% w/v and even more preferably from about 0.5% to about 5.0% w/v;
- about 2.5% w/v mannitol;
- about 0.10% w/v magnesium chloride;
- from about 0.2% about 0.30% w/v sodium chloride;
- about 3 or 4 millimolar citrate or phosphate buffer; and optionally one or more excipients selected from about 0.01% to about 0.12% w/v sorbate, from about 0.01% to about 0.12% w/v EDTA, and from about 0.005% to about 0.02% benzalkonium chloride, wherein the composition has a pH of about 5.0.

The present invention is further directed to a drug vehicle gel composition comprising from about 0.0075% to about 0.02% w/v brimonidine, preferably from about 0.015% to about 0.02% w/v and one or more nonionic surfactants selected from the group consisting of poloxamers, polysorbates, cyclodextrins, alkylaryl polyethers, polyoxyethyleneglycol alkyl ethers, tyloxapol, and polyoxyls at a total concentration from about 1.5% to about 5.9% w/v, preferably about 2.0% w/v polysorbate 80, about 1.0% w/v poloxamer 188 and about 1.0% w/v hydroxypropyl-gamma-cyclodextrin.

The present invention is further directed to a composition comprising one or more nonionic surfactants and at least one excipient selected from the group consisting of one or more viscosity enhancers, a polyol and an electrolyte, wherein micelles having an average diameter from about 12 to about 20 nanometers are formed, preferably from about 15 to about 20 nanometers and more preferably about 16 nanometers.

The present invention is further directed to a composition comprising an active agent selected from the group consisting of diquafosol, bimatoprost, cyclosporine-A, GLC, prednisolone forte, ketorolac, gentamycin, polytrim, ciprofloxacin, moxifloxacin, gatifloxacin, lifitegrast, besifloxacin, pilocarpine, brimonidine, timolol, dexmedetomidine, timoptic, dorzolamide, latanoprost, acetylsalicylic acid and a combination thereof, preferably cyclosporine-A, one or more nonionic surfactants and at least one excipient selected from the group consisting of one or more viscosity enhancers, a polyol and an electrolyte, wherein micelles having an average diameter from about 12 to about 20 nanometers are formed, preferably from about 15 to about 20 nanometers and more preferably about 16 nanometers.

In a preferred embodiment, drug vehicle compositions of the present invention do not contain polyacrylates such as Pemulen® materials including acrylate/C10-30 alkyl acrylate cross-polymers, or high molecular weight co-polymers of acrylic acid and a long chain alkyl methacrylate cross-linked with allyl ethers of pentaerythritol.

Lidocaine Gel Compositions

In one embodiment, the present invention is directed to a topical ophthalmological lidocaine gel composition comprising lidocaine or a salt thereof and magnesium chloride.

In a preferred embodiment, lidocaine is lidocaine hydrochloride.

In another preferred embodiment, the lidocaine or salt thereof is at a concentration from about 1% to about 5% w/v.

In another preferred embodiment, the present invention further comprises one or more excipients selected from the group consisting of a nonionic surfactant, a polyethylene glycol, mannitol, carboxymethyl cellulose and sodium chloride.

In another preferred embodiment, magnesium chloride is from about 0.01% to about 0.5% w/v.

In another preferred embodiment, the nonionic surfactant is polysorbate 80.

In another preferred embodiment, polysorbate 80 is at a concentration from about 1.5% to about 5.9% w/v.

In another preferred embodiment, the polyethylene glycol having a molecular weight of from about 400 to about 20,000 Daltons including polyethylene glycol 400 and polyethylene glycol 20000. Preferably, polyethylene glycol is at a concentration from about 0.1% to about 5% w/v.

In another preferred embodiment, mannitol is at a concentration from about 0.1% to about 5% w/v.

In another preferred embodiment, carboxymethyl cellulose is at a concentration from about 1% to about 5% w/v.

In another preferred embodiment, sodium chloride is at a concentration from about 0.1% to about 2% w/v.

In a preferred embodiment, the present invention is directed to a topical ophthalmological lidocaine gel composition comprising lidocaine or a salt thereof, magnesium chloride, a nonionic surfactant, a polyethylene glycol, mannitol, a viscosity enhancer and sodium chloride.

In another preferred embodiment, the present invention is directed to a topical ophthalmological lidocaine gel composition comprising:
- from about 3% to about 4% w/v lidocaine hydrochloride;
- from about 3% to about 4% w/v polysorbate 80;
- from about 0.25% to about 2.5% w/v of a polyethylene glycol having a molecular weight of from about 400 to about 20,000 Daltons;
- from about 0.25% to about 1.5% w/v mannitol; and
- from about 0.05% to about 0.2% w/v magnesium chloride.

In another preferred embodiment, the present invention is directed to a topical ophthalmological lidocaine gel composition comprising:
- about 3.5% w/v lidocaine hydrochloride;
- about 3.5% w/v polysorbate 80;
- from about 0.75% to about 1.50% w/v of a polyethylene glycol having a molecular weight of from about 400 to about 20,000 Daltons;
- about 0.75% w/v mannitol;
- about 0.1% w/v magnesium chloride;
- from about 0.9% to about 1.25% w/v sodium chloride;
- about 3 millimolar citrate buffer;
- from about 1.25% to about 1.50% w/v carboxymethyl cellulose; and
- about 0.1% w/v sorbate.

In another preferred embodiment, the present invention is directed to a topical ophthalmological lidocaine gel composition comprising:
- about 3.5% w/v lidocaine hydrochloride;
- about 3.5% w/v polysorbate 80;
- about 0.75% w/v polyethylene glycol 400;
- about 0.75% w/v mannitol;
- about 0.1% w/v magnesium chloride;
- about 0.9% w/v sodium chloride;
- about 3 millimolar citrate buffer;
- about 1.25% w/v carboxymethyl cellulose; and
- about 0.1% w/v sorbate.

In another preferred embodiment, the present invention is directed to a topical ophthalmological lidocaine gel composition comprising:
- about 3.5% w/v lidocaine hydrochloride;
- about 3.5% w/v polysorbate 80;
- about 0.75% w/v polyethylene glycol 400;
- about 0.75% w/v mannitol;
- about 0.1% w/v magnesium chloride;
- about 1.25% w/v sodium chloride;
- about 3 millimolar citrate buffer;
- about 1.40% w/v carboxymethyl cellulose; and
- about 0.1% w/v sorbate.

In another preferred embodiment, the present invention is directed to a topical ophthalmological lidocaine gel composition comprising:

about 3.5% w/v lidocaine hydrochloride;
about 3.5% w/v polysorbate 80;
about 1.5% w/v polyethylene glycol 20000;
about 0.75% w/v mannitol;
about 0.1% w/v magnesium chloride;
about 1.25% w/v sodium chloride;
about 3 millimolar citrate buffer;
about 1.50% w/v carboxymethyl cellulose; and
about 0.1% w/v sorbate.

In another embodiment, the present invention is directed to a method of inducing local anesthesia in an eye of a patient comprising topically applying compositions of the present invention to the eye of the patient.

Topical Compositions

In one embodiment, the present invention is directed to a topical composition comprising one or more topical active ingredients, one or more nonionic surfactants and one or more viscosity enhancers.

As used herein, topical active ingredients include but are not limited to topical analgesics such as lidocaine, lidocaine hydrochloride, menthol, camphor, methyl salicylate, cajuput oil, dementholised mint oil and clove oil; hemorrhoid treatment compounds such as hydrocortisone, phenylephrine hydrochloride and pramoxine hydrochloride; acne treatment compounds such as benzoyl peroxide, salicylic acid, azelaic acid, dapsone, resorcinol erythromycin and clindamycin; anti-wrinkle compounds such as retinoids including retinol, tretinoin, isotretinoin, alitretinoin, etretinate, acitretin, adapalene and tazarotene, vitamin C and alpha-hydroxy acids including glycolic acid, citric acid and lactic acid, coenzyme Q10 and niacinamide; anti-scar compounds such as *Allium cepa*, collagen and elastin; and mupirocin.

In a preferred embodiment, the present invention is directed to a topical analgesic composition comprising one or more topical analgesics preferably selected from the group consisting of lidocaine, lidocaine hydrochloride, menthol, camphor, methyl salicylate, cajuput oil, dementholised mint oil and clove oil, one or more surfactants and one or more viscosity enhancers.

In another preferred embodiment, the present invention is directed to a composition for the treatment of hemorrhoids comprising one or more hemorrhoid treatment compounds preferably selected from the group consisting of hydrocortisone, phenylephrine hydrochloride and pramoxine hydrochloride, one or more surfactants and one or more viscosity enhancers.

In another preferred embodiment, the present invention is directed to a composition for the treatment of acne comprising one or more acne treatment compounds, preferably selected from the group consisting of benzoyl peroxide, salicylic acid, azelaic acid, dapsone, resorcinol erythromycin and clindamycin, one or more surfactants and one or more viscosity enhancers.

In another preferred embodiment, the present invention is directed to a composition to reduce or eliminate skin wrinkles comprising one or more anti-wrinkle compounds, preferably selected from the group consisting of retinol, tretinoin, isotretinoin, alitretinoin, etretinate, acitretin, adapalene and tazarotene, vitamin C, glycolic acid, citric acid and lactic acid, coenzyme Q10 and niacinamide, one or more surfactants and one or more viscosity enhancers.

In another preferred embodiment, the present invention is directed to a composition to reduce or eliminate scars comprising one or more anti-scar compounds, preferably selected from the group consisting of *Allium cepa*, collagen and elastin, one or more surfactants and one or more viscosity enhancers.

In another preferred embodiment, the one or more topical active ingredients are at a concentration from about 0.001% to about 99% w/v.

Camphor may be present in topical compositions of the present invention at a concentration from about 1% to about 20% w/v, preferably from about 4% to about 15% w/v and more preferably from about 4% to about 11% w/v.

Menthol may be present in topical compositions of the present invention at a concentration from about 1% to about 20% w/v, preferably from about 5% to about 15% w/v and most preferably about 10% w/v.

Methyl salicylate may be present in topical compositions of the present invention at a concentration from about 1% to about 60% w/v, preferably from about 20% to about 40% w/v and more preferably from about 25% to about 35% w/v.

Cajuput oil may be present in topical compositions of the present invention at a concentration from about 1% to about 20% w/v, preferably from about 4% to about 10% w/v and more preferably from about 6% to about 8% w/v.

Dementholised mint oil may be present in topical compositions of the present invention at a concentration from about 1% to about 20% w/v, preferably from about 4% to about 15% w/v and more preferably from about 5% to about 7% w/v.

Clove oil may be present in topical compositions of the present invention at a concentration from about 1% to about 20% w/v, preferably from about 2% to about 10% w/v and more preferably from about 4% to about 6% w/v.

Hydrocortisone may be present in topical compositions of the present invention at a concentration from about 0.1% to about 10% w/v, preferably from about 0.5% to about 5% w/v and more preferably from about 1% to about 2.5% w/v.

Phenylephrine hydrochloride may be present in topical compositions of the present invention at a concentration from about 0.01% to about 1% w/v, preferably from about 0.1% to about 0.5% w/v and more preferably from about 0.2% to about 0.3% w/v.

Pramoxine hydrochloride may be present in topical compositions of the present invention at a concentration from about 0.1% to about 10% w/v, preferably from about 0.5% to about 5% w/v and more preferably from about 1% to about 2.5% w/v.

Benzoyl peroxide may be present in topical compositions of the present invention at a concentration from about 0.1% to about 10% w/v, preferably from about 1% to about 5% w/v and more preferably from about 3% to about 4% w/v.

Salicylic acid may be present in topical compositions of the present invention at a concentration from about 1% to about 20% w/v, preferably from about 5% to about 15% w/v and most preferably about 10% w/v.

Erythromycin may be present in topical compositions of the present invention at a concentration from about 0.1% to about 10% w/v, preferably from about 1% to about 10% w/v and more preferably from about 1% to about 5% w/v.

Clindamycin may be present in topical compositions of the present invention at a concentration from about 0.1% to about 10% w/v, preferably from about 1% to about 10% w/v and more preferably from about 1% to about 5% w/v.

Azelaic acid may be present in topical compositions of the present invention at a concentration from about 1% to about 50% w/v, preferably from about 5% to about 40% w/v and more preferably from about 10% to about 20% w/v.

Dapsone may be present in topical compositions of the present invention at a concentration from about 1% to about 20% w/v, preferably from about 1% to about 10% w/v and more preferably from about 4% to about 6% w/v.

Resorcinol may be present in topical compositions of the present invention at a concentration from about 1% to about 20% w/v, preferably from about 1% to about 10% w/v and more preferably from about 1% to about 5% w/v.

Vitamin C may be present in topical compositions of the present invention at a concentration from about 1% to about 30% w/v, preferably from about 5% to about 20% w/v and more preferably from about 5% to about 15% w/v.

Alpha-hydroxy acids may be present in topical compositions of the present invention at a concentration from about 1% to about 80% w/v, preferably from about 5% to about 70% w/v and more preferably from about 10% to about 70% w/v.

Coenzyme Q10 may be present in topical compositions of the present invention at a concentration from about 0.1% to about 10% w/v, preferably from about 1% to about 5% w/v and more preferably from about 1% to about 3% w/v.

Niacinamide may be present in topical compositions of the present invention at a concentration from about 1% to about 30% w/v, preferably from about 5% to about 20% w/v and more preferably from about 5% to about 15% w/v.

Collagen may be present in topical compositions of the present invention at a concentration from about 1% to about 99% w/v, preferably from about 1% to about 90% w/v.

Elastin may be present in topical compositions of the present invention at a concentration from about 1% to about 99% w/v, preferably from about 1% to about 90% w/v.

Retinoids may be present in topical compositions of the present invention at a concentration from about 0.01% to about 10% w/v, preferably from about 0.1% to about 5% w/v and more preferably from about 0.1% to about 3% w/v.

In a preferred embodiment, the one or more nonionic surfactants of the topical compositions of the present invention are selected from the group consisting of poloxamers, polysorbates, cyclodextrins, alkylaryl polyethers, polyoxyethyleneglycol alkyl ethers, tyloxapol, and polyoxyls, preferably at a total concentration from about 1.0% to about 7.0% w/v.

In another preferred embodiment, the one or more viscosity enhancers of the topical compositions of the present invention are selected from the group consisting of cellulose derivatives, carbomers, gums, dextrans, polyvinyl alcohol, polyacrylic acids, povidone, polyethylene glycol, propylene glycol, chitosans, and hyaluronates and hyaluronic acids, preferably at a total concentration from about 0.05% to about 2.0% w/v.

In another embodiment, the topical compositions of the present invention further comprise one or more excipients selected from the group consisting of one or more polyols, one or more electrolytes, one or more preservatives and one or more antioxidants.

In a preferred embodiment, the one or more polyols of the topical compositions of the present invention are selected from the group consisting of mannitol, glycerol, erythritol, lactitol, xylitol, sorbitol, isosorbide, and maltitol.

In another preferred embodiment, the one or more electrolytes of the topical compositions of the present invention are selected from the group consisting of magnesium ions, sodium chloride and potassium chloride.

In another preferred embodiment, the one or more preservatives of the topical compositions of the present invention are selected from the group consisting of benzalkonium chloride, sorbate, methylparaben, polypropylparaben, chlorobutanol, thimerosal, phenylmercuric acetate, perborate and phenylmercuric nitrate.

In another preferred embodiment, the one or more antioxidants of the topical compositions of the present invention are selected from the group consisting of citrate, EDTA, sodium metabisulfite, sodium thiosulfate, acetylcysteine, butylated hydroxyanisole and butylated hydroxytoluene.

Methods of the Invention

Conditions that may be treated by combining the micellar nonionic surfactant discovered range for Moisture-Lock™ effect evaporative shield (from about 1.5% to about 5.5% w/v) are limited on the upper limit by increased risk of epithelial toxicity. Within this critical range with variations in viscosity, electrolytes, and preferred excipients allows for a wide range of characteristics appropriate for differentiated treatment opportunity. These treatment opportunities range from enhanced moisture and contact lens deposit reduction and protection to more effective potential treatment of severe eye disease. Greater and more prolonged exposure to natural tears that may be locked in by the discoveries herein along with prolonged exposure to excipients found to be protective to the corneal epithelium may enhance the currently inadequate treatments available for surface eye disease, particularly related to corneal irritation and inadequate tear function and or volume.

Autologous serum is often used to treat severe dry eye with greater effectiveness than any other drug to date. Autologous serum consists of spinning down blood and removing serum for topical application. This plasma is believed to contain many growth factors useful in optimizing therapeutic benefit to the ocular surface and corneal epithelium in particular. The sequestration of induced plasma triggered by the discovered formulation properties of the present invention combined with the trigger of the trigeminal nerve via TPV stimulation, of which terpenoids are an example, provides a surrogate autologous serum with great potential therapeutic benefit. The induced plasma may be maintained on the surface longer than autologous serum and is less costly and more practical to apply than autologous serum. Additional benefit derives from the combined discovery of tear sequestration and induction of tearing consisting primarily of plasma is the creation of a surrogate autologous serum effect.

The present invention is further directed to a method of treating eye discomfort comprising administering an artificial tear composition comprising:
1) from 0.2% to 7.0% w/v of at least one nonionic surfactant; and
2) one or more non-Newtonian viscosity enhancing excipients of high molecular weight blend having from about 0.1 centipoise (cps) to about 3,000 cps @ 1% 27 C; to a subject in need thereof.

The artificial tear compositions of the present invention are suitable for administration two, three or four times per day to a subject in need thereof.

TABLE 10

Conditions to be Treated by Commercial Compositions

| ALL PRODUCT LINE | AQus ™ CL-Tears | AQus ™ Tears Plus | AQus ™ Tears Advanced |
|---|---|---|---|
| BASE: | | | |
| combines proprietary NIS blend + V + electrolyte + epithelial protectants | 0.10% | 0.50% | 1.00% |
| DEWS CLASSIFICATION | I, II | II+ | III |
| Visual blur Duration | | | |

TABLE 10-continued

Conditions to be Treated by Commercial Compositions

CONDITION:

| CL | CL insertion coating protection CL pre, during wear enhancement | | |
|---|---|---|---|
| COMPUTER | +, ++ | ++, +++ | +++, ++++ |
| COSMETIC SHIELD | +, ++ | ++, +++ | +++, ++++ |
| ENVIRONMENTAL | +, ++ | ++, +++ | +++, ++++ |
| ALLERGIC | +, ++ | ++, +++ | +++, ++++ |
| PRESERVATIVE SHIELD | +, ++ | ++, +++ | +++, ++++ |
| DRY EYE THERAPY | +, ++ | ++, +++ | +++, ++++ |
| SPK THERAPY | +, ++ | ++, +++ | +++, ++++ |
| MGD THERAPY | +, ++ | ++, +++ | +++, ++++ |
| GLAUCOMA DROP TOLERANCE | +, ++ | ++, +++ | +++, ++++ |
| SURGERY | − | START: | |
| GLAUCOMA SURGERY | − | ++, +++ | +++, ++++ |
| LASIK | − | ++, +++ | +++, ++++ |
| PRK | − | ++, +++ | +++, ++++ |
| CORNEAL TRANSPLANT | − | ++, +++ | +++, ++++ |
| CATARACT SURGERY | − | ++, +++ | +++, ++++ |

| ALL PRODUCT LINE | AQus ™ Tears Advanced Plus | AQus ™ Tears Extreme |
|---|---|---|
| BASE: | | |
| combines proprietary NIS blend + V + electrolyte + epithelial protectants | 1.35% | VISCOSITY TO 350 |
| DEWS CLASSIFICATION | III+, IV | V |
| Visual blur Duration | | |
| CONDITION: | | |
| CL | | |
| COMPUTER | | |
| COSMETIC SHIELD | | |
| ENVIRONMENTAL | | |
| ALLERGIC | ++++, +++++ | |
| PRESERVATIVE SHIELD | ++++, +++++ | |
| DRY EYE THERAPY | ++++, +++++ | +++++! |
| SPK THERAPY | ++++, +++++ | +++++! |
| MGD THERAPY | ++++, +++++ | +++++! |
| GLAUCOMA DROP TOLERANCE | ++++, +++++ | +++++! |
| SURGERY | | |
| GLAUCOMA SURGERY | ++++, +++++ | +++++! |
| LASIK | ++++, +++++ | +++++! |
| PRK | ++++, +++++ | +++++! |
| CORNEAL TRANSPLANT | ++++, +++++ | +++++! |
| CATARACT SURGERY | ++++, +++++ | +++++! |

Each + refers to disease status: early (1), moderate (2), moderate-severe (3), severe (4), extreme (5 or 5!).

As seen in Table 10, varying the concentration of the viscosity enhancer and polyol provides different compositions that may serve different purposes. For example, a viscosity enhancer concentration of 0.10% w/v and polyol concentration of 1.00% w/v may be best suited for use on dry eye diseases classified as either a I or II by the international DEWS classification system. Further, subjects with a disease that has reached a severe state may benefit from a composition of the present invention comprising Captisol® or hydroxypropyl-gamma-cyclodextrin.

AQus™ CL-Tears may be used to treat mild dry eye and/or contact lens dryness. AQus™ CL-Tears is especially useful for the International Dry Eye Workshop ("DEWS") classification I and II dry eye diseases. Further, AQus™ CL-Tears has an osmolarity less than about 320 osmoles and causes no visual blur upon instillation.

AQus™ Tears plus may be used to treat moderate dry eye. AQus™ CL-Tears is especially useful for DEWS classification III dry eye diseases. Further, AQus™ CL-Tears has an osmolarity less than about 340 osmoles and causes about 5 seconds of visual blur upon instillation.

AQus™ Tears Advanced may be used to treat moderate to severe dry eye. AQus™ Tears Advanced is especially useful for DEWS classification IV dry eye diseases. Further, AQus™ Tears Advanced has an osmolarity less than about 360 osmoles and causes about 15-30 seconds of visual blur upon instillation.

AQus™ Tears Advanced Plus and AQus™ Tears Extreme may be used to treat moderate to severe dry eye. AQus™ Tears Advanced Plus and AQus™ Tears Extreme are especially useful for DEWS classification V dry eye diseases. Further, AQus™ Tears Advanced Plus and AQus™ Tears Extreme have an osmolarity greater than about 360 osmoles and causes about 30-60 seconds of visual blur upon instillation.

AQus™ Tears MGD may be used to treat Meibomian Gland Dysfunction ("MGD"). AQus™ Tears MGD is especially useful for DEWS classification I-IV dry eye diseases. Further, AQus™ Tears MGD has an osmolarity from about 300 to about 360 osmoles and causes about 10-15 seconds of visual blur upon instillation. Finally, AQus™ formulations noted to treat DEWS classification III-IV dry eye diseases may also be used to treat MGD.

AQus is a trademark owned by PS Therapies, Ltd.

Topical compositions of the present invention may be used in treating topical conditions.

In a preferred embodiment, the present invention is directed to a method of reducing or eliminating pain comprising applying a composition of the present invention to a subject in need thereof.

In another preferred embodiment, the present invention is directed to a method of treating hemorrhoids comprising applying a composition of the present invention to a subject in need thereof.

In another preferred embodiment, the present invention is directed to a method of reducing or eliminating acne comprising applying a composition of the present invention to a subject in need thereof.

In another preferred embodiment, the present invention is directed to a method of reducing or eliminating wrinkles comprising applying a composition of the present invention to a subject in need thereof.

In another preferred embodiment, the present invention is directed to a method of reducing or eliminating scars comprising applying a composition of the present invention to a subject in need thereof.

EXAMPLES

Example 1—Moisture-Lock' Effect as a Function of Nonionic Surfactant Concentration Moisture-Lock™ is defined by the Moisture-Lock™ Index. The Moisture-Lock™ Index is calculated by multiplying the duration of the wetting effect in minutes by the qualitative wetness felt along the tear menisci of the lower lids, rated from 0 to 4.0, maximum, for a specific duration of time sampled in equal increments. Alternatively, it can be calculated by multiplying the duration of the wetting effect by the tear prism in millimeters, which is coined Moisture-Lock™ Index 2. The value of the qualitative method over the quantitative is the sensation of moisture. Moisture is the exact corollary to dryness from which 10 million U.S. citizens alone are afflicted. In most cases of dry eye syndrome, it is the sensation of dryness and related burning and irritation that are the most common debilitating symptoms. Additional symptoms include reduced contrast acuity, Snellen acuity, increasingly severe discomfort and frank pain. The lower threshold for the Moisture-Lock™ Index that denotes Moisture-Lock™ effect is 10. For example, for a 40-minute duration sampled in 10-minute increments, a Moisture-Lock™ Index from 10 to 20 indicates slight Moisture-Lock™ effect, from 21 to 75 indicates a moderate Moisture-Lock™ effect, from 76 to 100 indicates a high Moisture-Lock™ and greater than 100 indicates a very high Moisture-Lock™ effect. Shown below in Table 11 is Moisture-Lock™ Index for increments of total nonionic surfactant ("NIS") concentration from 0.0% w/v to 7% w/v.

TABLE 11

Moisture-Lock ™ effect as a property of nonionic surfactant concentration

| NIS (% w/v) | Duration (minutes) | Wetness Rating (0 to 4.0; 4.0 maximum) | Moisture-Lock ™ Index | Description |
|---|---|---|---|---|
| 0% | 1 | 1.5 | 1.5 | |
| | 10 | 0.5 | 5 | |
| | 20 | 0 | 0 | |
| | 30 | 0 | 0 | |
| | 40 | 0 | 0 | |
| | Total | | 6.5 | no ML |
| 1% | 1 | 2.0 | 2 | |
| | 10 | 1.5 | 15 | |
| | 20 | 0.5 | 10 | |
| | 30 | 0 | 0 | |
| | 40 | 0 | 0 | |
| | Total | | 27 | mod ML |
| 3% | 1 | 3.25 | 3.25 | |
| | 10 | 2.5 | 25 | |
| | 20 | 1.5 | 30 | |
| | 30 | 0.75 | 22.5 | |
| | 40 | 0.5 | 20 | |
| | Total | | 100.75 | high ML |
| 5% | 1 | 4 | 4 | |
| | 10 | 3.75 | 37.5 | |
| | 20 | 1.5 | 30 | |
| | 30 | 0.75 | 22.5 | |
| | 40 | 0.5 | 20 | |
| | Total | | 114 | very high ML |
| 7% | 1 | 3.5 | 3.5 | |
| | 10 | 3 | 30 | |
| | 20 | 1.25 | 25 | |
| | 30 | 0.5 | 15 | |
| | 40 | 0.25 | 10 | |
| | Total | | 83.5 | high ML |

Figure 2:
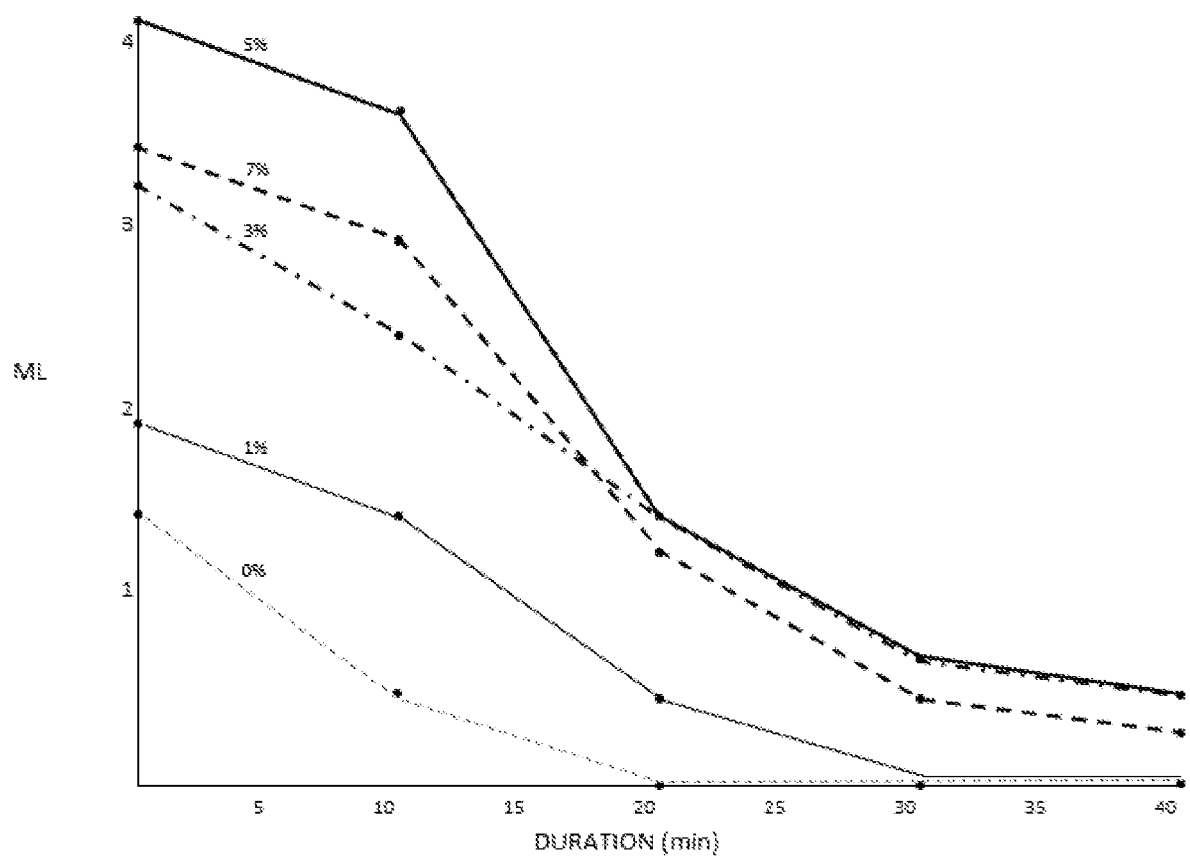
FIG. 2. Graph of Moisture-Lock™ effect values over time for various % w/v nonionic surfactant concentrations.

"no ML" denotes no Moisture-Lock ™ effect
"mod ML" denotes moderate Moisture-Lock ™ effect
"high ML" denotes high Moisture-Lock ™ effect
"very high ML" denotes very high Moisture-Lock ™ effect
"NIS" denotes nonionic surfactant As can be seen in Table 11 and FIG. 1 the Moisture-Lock™ effect peaks around 5.0% w/v total nonionic surfactant concentration with a normal distribution as denoted by the bell-shaped curve in FIG. 1. Further, as can be seen in Table 11 and FIG. 2 use of about 5.0% w/v total nonionic surfactant results in the greatest Moisture-Lock™ effect.

Example 2—Moisture-Lock™ Effect after Induced Tearing

The following experiment was conducted to test the enhanced Moisture-Lock™ effect of compositions of the present invention that induce tearing. The Moisture-Lock effect was measured as duration of sensation of increased moisture and compared to a control artificial tear (Nanotears® XP). 2 drops of a composition of the present invention comprising polysorbate 1.5% w/v, poloxamer 407 0.20% w/v, poloxamer 188 1.0% w/v, hydroxy propyl gamma cyclodextrin 1.0% w/v; mannitol 2.5% w/v; $MgCl_2$ 0.10% w/v; hydroxypropyl methyl cellulose 1.30% w/v, NaCl 0.45% w/v, citrate buffer 3 mM; and menthol 0.07 mM with a pH of 5.5 ("composition S2-2") was instilled in one eye of the first patient. 2 drops of Nanotears® XP were instilled in one eye of a second patient. Moisture was quantified from 1-4 at 5-minute intervals from 5 to 50 minutes. Results can be seen in Table 12 below.

TABLE 12

Sensation of Moisture following instillation of a composition of the present invention

| Time (sec) | Composition S2-2 | Nanotears ® XP |
|---|---|---|
| 5 | 4 | 4 |
| 10 | 4 | 3.5 |
| 15 | 3.5 | 2 |
| 20 | 2.75 | 1 |
| 25 | 2.5 | 0 |
| 30 | 2 | — |
| 35 | 1.5 | — |
| 40 | 1 | — |
| 45 | 0.5 | — |
| 50 | 0 | — |

As demonstrated in Table 12, composition S2-2 maintained moisture for at least twice as long as Nanotears® XP.

Example 3—Enhanced Comfort and Initial Instillation Qualities

Composition X:
3.00% Polysorbate 80
0.10% Poloxamer 188
0.01% Polyoxyl Castor oil
0.50% HPMC
2.50% Mannitol
0.10% $MgCl_2$
0.75% NaCl
3 mM Phosphate buffer
pH 7.00
Method
One drop of Composition X was applied to the right eye and one drop of Refresh Liquigel® applied to the left eye. After 30 minutes, a qualitative tear breakup time was calculated. A qualitative test was considered more meaningful in terms of assessment of clinical benefit because observing and measuring quantity typically require addition of a stain such as fluorescein. Further, the purpose of measuring the tear break up time is to assess when the tear film breaks up and dellen formation (dry spots) begin to form. This test was based on a) onset of stinging and b) onset of reflex tearing vs. time without a blink. Visual blur following instillation was assessed as the time required to read 4-point font at 40 cm that could be maintained for two blink cycles (initially blinking may cause viscous film resurfacing).

Results

Visual blur in the right eye lasted for fifteen seconds compared to ninety seconds for the left eye. This six-times reduction in visual blur was unexpected over the commercially available Refresh Liquigel®. Sting onset was delayed by four seconds over Refresh Liquigel® as Composition X did not induce sting until twelve seconds after instillation as compared to eight seconds for Refresh Liquigel®. Finally, reflex tearing onset was also delayed by four seconds over Refresh Liquigel® as Composition X did not induce reflex tearing until twenty seconds after installation as compared to sixteen seconds for Refresh Liquigel®.

Example 4—(Hypothetical) Lid Wipes

Applications of preferred embodiments were applied to lid wipes, particularly compositions 86, 87, and 88 from Table 4 above. Preferably the user first applied a warm pack or in some manner heated the lid wipe and then vigorously rubs along the lid margins in the region of the meibomian glands. Lid massage in the form of a rolled Q-tip® following the vigorous lid wipe with compositions of the current invention may be beneficial. The result is a greatly reduced incidence, if performed prophylactically, and a substantial therapeutic benefit to patients with Meibomian gland dysfunction (MGD). Dissolution of lipid deposits, with reduction in blocked lacrimal ducts, is augmented by this application of the present invention.

Example 5—Artificial Tear Gels

Artificial tear gels are virtually described for purposes of prolonged surface contact with some added initial blur. These artificial tear gels may be used during a time that initial blur is unproblematic such as insertion before sleep. Such gels may be with or without an active drug for purposes of therapeutic treatment. An example of an artificial tear gel of the present invention is described below with and without an active ingredient.

Artificial Tear Gel
2.0% Polysorbate 80
1.0% Poloxamer 188
1.0% Hydroxypropyl gamma cyclodextrin
1.5% to 20% Hydroxypropyl methyl cellulose (preferably 1.7% to 2.5%)
2.5% Mannitol
0.10% $MgCl_2$
0.75% NaCl
Citrate buffer to pH 5.0
0.10 mM Menthol
Lidocaine Tear Gel
1.0% Lidocaine
2.0% Polysorbate 80
1.0% Poloxamer 188
1.0% Hydroxypropyl gamma cyclodextrin
1.5% to 20% Hydroxypropyl methyl cellulose (preferably 1.7% to 2.5%)
2.5% Mannitol
0.10% $MgCl_2$
0.75% NaCl
3 mM Phosphate buffer
pH 6.0
Cyclosporine-A Tear Gel
Cyclosporine-A 1.0%
2.0% Polysorbate 80
1.0% Poloxamer 188
1.0% Hydroxypropyl gamma cyclodextrin
1.5% to 20% Hydroxypropyl methyl cellulose (preferably 1.7% to 2.5%)
2.5% Mannitol
0.10% $MgCl_2$
0.75% NaCl
Citrate buffer to pH 5.0
0.15 mM Menthol Advantages of these tear gel compositions are prolonged duration and minimized blur. The viscosity at low shear is from about 500 cps to about 10,000 cps. Visual blur is less than 5 minutes. Maximum moisture-lock is precipitated.

Example 6—Night Vision Compositions (Virtual)

Compositions of the present invention may be used as a drug vehicle. An example of use as a drug vehicle is for pilocarpine for use as an inductor of miotic pupils. 0.075% w/v pilocarpine will be suspended in saline (0.9% w/v NaCl) and in a composition of the present invention detailed below. These two pilocarpine compositions will then be instilled in the eye of a subject at separate times with a sufficient wash out period between instillations. Pupil size will be measured 1 hour after instillation.

Pilocarpine Artificial Enhanced Tear
0.075% Pilocarpine
2.0% Polysorbate 80
1.0% Poloxamer 188
1.0% Hydroxypropyl gamma cyclodextrin
1.30% Hydroxypropyl methyl cellulose
2.5% Mannitol
0.10% $MgCl_2$
0.30% NaCl
Phosphate buffer to pH 7.0
Results 1 hour after instillation of pilocarpine in the artificial enhanced tear composition, the pupil size will be reduced by 1.5 mm vs 0.5 mm reduction in pupil size 1 hour after instillation of pilocarpine in the saline composition.

Example 7—(Hypothetical) Cyclosporine-A Drug Vehicle

Cyclosporine-A is added to a composition of the present invention at a concentration from about 0.05% to about 2.0% w/v, more preferably from about 0.075% to about 1.5% w/v, and most preferably from about 0.09% to about 0.125% w/v. wherein the composition comprises one or more nonionic surfactants are at a concentration from about 1.5% to about 4.9% w/v, more preferably from about 2.5% to about 4.0% w/v, a viscosity agent, preferably a cellulose derivative and most preferably HPMC or CMC at low shear interblink viscosities of 50 cps to 500 cps, more preferably 100 cps to 400 cps, optionally from about 0.01 to about 20 mM menthol, preferably from about 0.07 to about 12 mM and optionally a reduced pH, hypoosmolarity and or hyperosmolarity. The drug vehicle when combined with cyclosporine-A results in an enhanced duration and effectiveness of the anti-inflammatory effects of cyclosporine-A upon the secretory mucin cells and other tear secretion glands of the lacrimal and accessory lacrimal apparatus. Further the drug vehicle enhances the general anti-inflammatory effects of such compositions on the eye lid margins.

Example 8—Dexmedetomidine Drug Vehicle 2 drops of a composition comprising dexmedetomidine 0.075% w/v, polysorbate 4.0% w/v, hydroxypropylmethyl cellulose 1.35% w/v, sorbate 0.10% w/v, BAK 0.02% w/v, EDTA 0.10% w/v, and a phosphate or a citrate buffer with a pH of 6.0 ("AQus™ Dex") was in one eye of a first patient and 2 drops of a composition comprising dexmedetomidine 0.07% w/v in saline and phosphate buffer with a pH of 6.0 ("saline Dex") was instilled in one eye of a second patient. Tests were performed to measure the intraocular pressure ("TOP") in both eyes of each patient, where the non-instilled contralateral eye would thereby serve as a measure of systemic absorption. The IOP was measured at baseline (1 pm), and drops were instilled subsequently at 8 am for check at 1 pm (5 hours post instillation).

Results

Baseline TOP for both patients was 18.25 mm Hg. 5 hours after instillation of the saline Dex composition pressure in both eyes dropped to 13.5 mm Hg. In contrast, 5 hours after instillation of the AQus™ Dex composition pressure dropped to 12.0 mm Hg in the treated eye and 16.5 mm Hg in the untreated eye.

These results demonstrate that the compositions of the present invention are effective drug vehicles that reduce systemic absorption of the active ingredient resulting in a more effective application with reduced systemic side effects.

Example 9—Solubilization of Cyclosporine-A

Method 0.09% cyclosporine-A was added to several compositions in an attempt to provide a stable, clear solution. Specifically, these compositions were as follows: 1) 4% Captisol®, 2) 0.5% glycofurol, 3) 0.25% polyoxyl 35 castor oil, 4) 4% γ-cyclodextrin, 5) 4% poloxamer 407, 6) 1% polysorbate 80, 7) 4% Captisol® and 0.5% glycofurol, 8) 4% cyclodextrin, 0.5% glycofurol, and 0.25% polyoxyl 40 castor oil, 9) 4% poloxamer 188, 0.5% glycofurol and 0.02% BAK, 10) 2% polysorbate 80, 11) 3% polysorbate 80, 12) 3.5% polysorbate 80, 13 4% polysorbate 80 and 0.01% polyoxyl castor oil and 14) 3.5% polysorbate 80, 4.0% poloxamer 407 and 0.01% polyoxyl castor oil.

Results

Compositions 1), 4-6), and 12) did not solubilize cyclosporine-A. Compositions 3), 10) and 11) sparingly solubilized cyclosporine-A. Compositions 7-9) resulted precipitate formation. Composition 12) solubilized cyclosporine-A but was not stable or clear. Compositions 2), 13) and 14) solubilized cyclosporine-A and resulted in stable and clear solutions.

Example 10—Increased Tear Volume with Cyclosporine-A Composition

Figure 4:
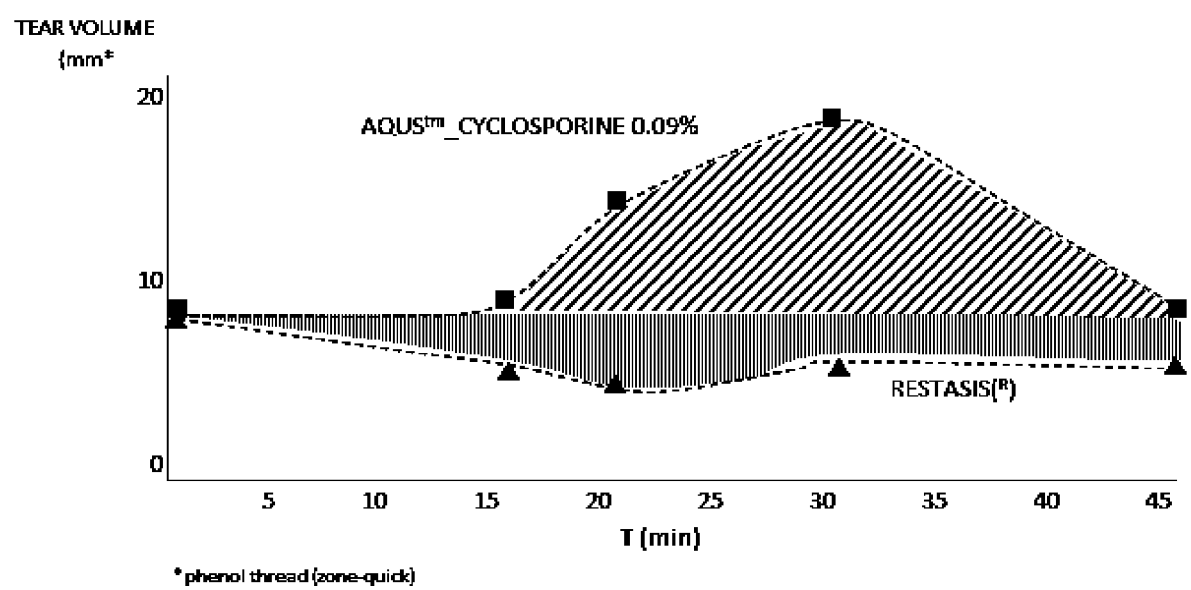
FIG. 4. Schirmer's test of tear volume after installation of Composition #C12 and Restasis®.
Figure 5:
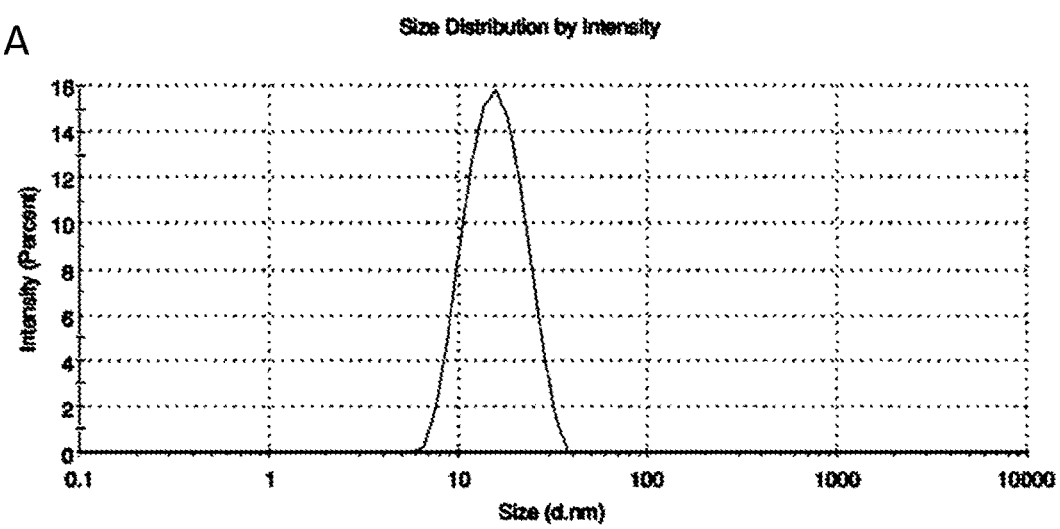
FIG. 5. Average micelle size of Composition #C12, panel A, and Restasis®, panel B.
Figure 5:
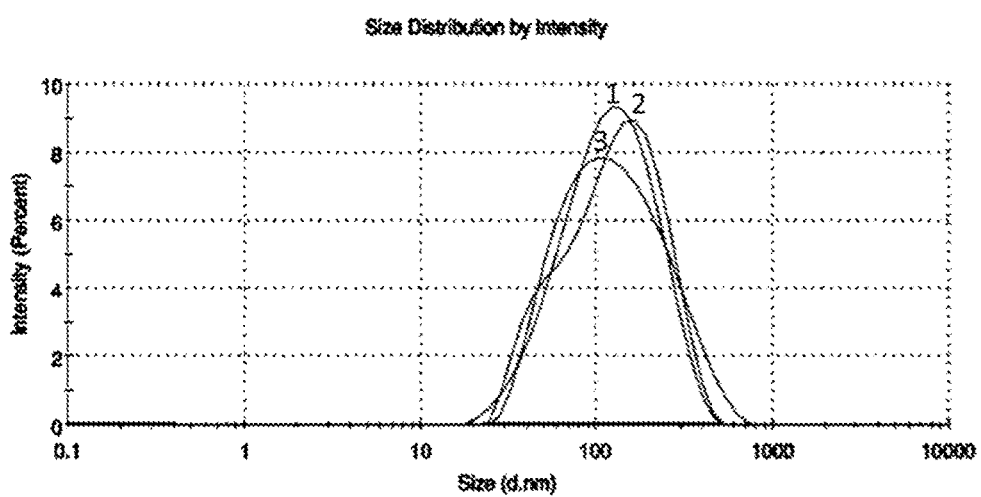

Composition #C12 from Table 10, above, was instilled in each eye of a subject. Tear volume was calculated via the Schirmer's test at 5-minute intervals to 45 minutes using phenol thread. After saline was used to clear the eyes of the subject, Restasis® was instilled in each eye of the same subject. Tear volume was calculated via the Schirmer's test at 5-minute intervals to 45 minutes using phenol thread. Results from this experiment can be seen in FIG. 4. Specifically, Composition #C12 increased tear volume from 8.5 millimeters to about 10 millimeters at 15 minutes after instillation, 15 millimeters at 20 minutes and peaked at 20 millimeters at 30 minutes after instillation. After 30 minutes, the subjects tear volume slowly decreased to 9.0 at 45 minutes. In contrast, installation of Restasis® in the eyes of the subject resulted in a decreased tear volume at all time points including a peak decrease to about 6 millimeters at 15 and 30 minutes. Further, the subject reported that the lid margin felt only marginally wet 5 minutes after instillation of Restasis® and felt dry by 10 minutes after instillation. In contrast, the subject reported a welling of tears along the lid margin at both 5 and 10 minutes after instillation of Composition #C12. The wet feeling continued through 20 minutes to marginally wet at 30 minutes post instillation. The subject further reported minimal stinging with Restasis® and no stinging with Composition #C12. Finally, there subject reported only minimal blur lasting 15 seconds for each of Restasis® and Example 11—Nano-Micelle Size Distribution of Cyclosporine-A Compositions Composition #C12 and Restasis® were each measured for nano-micelle size distribution. See FIG. 5. As shown in FIG. 5, the average diameter of nano-micelles of Composition #C12 of the present invention was 16.3 nanometers with a standard deviation of 5.55 nanometers. Restasis® had an average size of 135.1 nanometers with a standard deviation of 77.81 nanometers.

Example 12—Enhanced Tearing Using an all GRAS Artificial Tears Composition (Virtual)

Method

GRAS Composition—

| | |
|---|---|
| 2.0% w/v | polysorbate 80 |
| 1.45% w/v | carboxymethyl cellulose (high MW 2% = 3,500 cps) |
| 0.34 mM | menthol |
| 0.10% w/v | sorbate |
| Q.S. | sterile saline |
| 7.0 | pH (adjusted) |

A polyphenol thread (Zone Quick®) was used to provide a Schirmer's testing measurement of tear volume. The thread was applied to the lateral canthus prior to administration of the formulation above and again to the lateral canthus at time increments shown below. The formulation was administered into the right eye ("OD") of the subject and the left eyes of the subject ("OS") was used as the control. Results of this experiment can be seen in Table 19 below.

Results

TABLE 13

| Time (min) | OD (mm) | OS (mm) |
|---|---|---|
| −1 | 9.5 | 9 |
| 5 | 30+ | 8.5-9.5 |
| 10 | 22 | 8.5-9.5 |
| 15 | 17 | 8.5-9.5 |
| 30 | 17 | 8.5-9.5 |
| 45 | 12 | 8.5-9.5 |
| 60 | 12 | 8.5-9.5 |
| 75 | 10 | 8.5-9.5 |

The results of Table 13 indicate that the subject suffered from dry eye prior to the instillation of the GRAS composition. Following instillation, the tear volume of the subjects treated eye increased for at least 1 hour.

Example 13—Effect of Sorbate Concentration on Tearing Production (Virtual)

Method

The dry eye subject of Example 12, above, was administered the GRAS composition of Example 12, which includes 0.10% w/v sorbate; and two additional modified versions of the GRAS composition including a no sorbate composition and a 0.12% w/v sorbate composition.

Results

Tearing at 5-15 Minutes:

Subject detected no difference between the 3 compositions in tearing at 5 minutes post administration. However, subject noted enhanced tearing for at least 10-15 minutes following administration with the 0.12% w/v sorbate composition along with a sharper sensation upon instillation.

What is claimed is:

1. A topical skin composition comprising lidocaine or a salt thereof, poloxamer 407, poloxamer 188, polyoxyl castor oil, polyethylene glycol 400, menthol, and carbomer.

2. A topical skin composition comprising:
   about 4% w/w lidocaine or a salt thereof;
   about 1% w/w poloxamer 407;
   about 0.2% w/w poloxamer 188;
   about 0.25% w/w polyoxyl castor oil;
   about 0.5% w/w polyethylene glycol 400;
   about 0.75% w/w menthol; and
   about 1% w/w carbomer,
wherein w/w denotes weight by total weight of the composition.

* * * * *